(12) United States Patent
Adam et al.

(10) Patent No.: US 7,994,394 B2
(45) Date of Patent: Aug. 9, 2011

(54) DISEASE-INDUCIBLE PROMOTERS

(75) Inventors: Luc Adam, Hayward, CA (US); T. Lynne Reuber, San Mateo, CA (US); Karen S. Century, Albany, CA (US)

(73) Assignee: Mendel Biotechnology, Inc., Hayward, CA (US)

( * ) Notice: Subject to any disclaimer, the term of this patent is extended or adjusted under 35 U.S.C. 154(b) by 235 days.

(21) Appl. No.: 12/298,134

(22) PCT Filed: Apr. 23, 2007

(86) PCT No.: PCT/US2007/009890
§ 371 (c)(1),
(2), (4) Date: Oct. 22, 2008

(87) PCT Pub. No.: WO2007/127186
PCT Pub. Date: Nov. 8, 2007

(65) Prior Publication Data
US 2009/0151015 A1  Jun. 11, 2009

Related U.S. Application Data

(60) Provisional application No. 60/794,671, filed on Apr. 24, 2006.

(51) Int. Cl.
*A01H 5/00* (2006.01)
*A01H 5/10* (2006.01)
*C12N 15/09* (2006.01)
*C12N 15/82* (2006.01)

(52) U.S. Cl. ........ 800/279; 800/278; 800/298; 800/295; 435/69.1; 435/320.1; 536/24.1

(58) Field of Classification Search .......................... None
See application file for complete search history.

(56) References Cited

U.S. PATENT DOCUMENTS

| 6,664,446 B2 * | 12/2003 | Heard et al. | .................. 800/301 |
| 7,196,245 B2 | 3/2007 | Jiang et al. | |
| 2004/0205841 A1 * | 10/2004 | Lawrence | ..................... 800/279 |

FOREIGN PATENT DOCUMENTS

| WO | WO 00/60086 | 10/2000 |
| WO | WO 02/50293 A2 | 6/2002 |
| WO | WO 2006/033708 | 3/2006 |

OTHER PUBLICATIONS

Michiels et al. Plant Molecular Biology Reporter (2003) 21:295-302.*
EMBL Jul. 15, 2002, "Sequence 12,from Patent W00250293." XP002578437 retrieved from EBI accession No. ENBL:AX463556 Database accession No. AX463556.
Ecker , Joseph (Jun. 24, 2002) TAIR—Locus: AT1G16420.
AGI-TIGR (Mar. 12, 2001) TAIR Gene Model: AT1G26380.
AGI-TIGR (Mar. 12, 2001) TAIR Gene Model: AT1G26420.
AGI-TIGR (Mar. 12, 2001) TAIR Gene Model: AT1G28190.
AGI-TIGR (Feb. 5, 2001) TAIR Gene Model: AT1G56060.
AGI-TIGR (Feb. 5, 2001) TAIR Gene Model: AT1G61560.
AGI-TIGR (Mar. 6, 2001) TAIR Gene Model: AT1G74360.
AGI-TIGR (Jan. 25, 2001) TAIR Gene Model: AT2G30750.
AGI-TIGR (Jan. 25, 2001) TAIR Gene Model: AT2G32210.
AGI-TIGR (Jan. 25, 2001) TAIR Gene Model: T2G35980.
AGI-TIGR (Sep. 8, 2000) TAIR Gene Model: AT3G09410.
AGI-TIGR (Sep. 8, 2000) TAIR Gene Model: AT3G18250.
AGI-TIGR (Sep. 8, 2000) TAIR Gene Model: AT3G63380.
AGI-TIGR (Jan. 29, 2001) TAIR Gene Model: AT4G01010.
AGI-TIGR (Aug. 14, 2000) TAIR Gene Model: AT4G02330.
AGI-TIGR (Aug. 14, 2000) TAIR Gene Model: AT4G21390.
AGI-TIGR (Aug. 8, 2001) TAIR Gene Model: AT4G35110.
AGI-TIGR (Jan. 30, 2001) TAIR Gene Model: AT5G22530.
AGI-TIGR (Nov. 15, 2001) TAIR Gene Model: AT5G64905.
AGI-TIGR (Feb. 5, 2001) TAIR Gene Model: AT1G02360.
AGI-TIGR (Mar. 12, 2001) TAIR Gene Model: AT1G24140.
AGI-TIGR (May 2, 2003) TAIR Gene Model: AT1G24145.
AGI-TIGR (Feb. 7, 2001) TAIR Gene Model: AT1G35230.
AGI-TIGR (Feb. 7, 2001) TAIR Gene Model: AT1G57630.
AGI-TIGR (Jul. 20, 2001) TAIR Gene Model: AT1G67810.
AGI-TIGR (Jan. 25, 2001) TAIR Gene Model: AT2G22880.
AGI-TIGR (Aug. 14, 2000) TAIR Gene Model: AT4G18250.
AGI-TIGR (Aug. 14, 2000) TAIR Gene Model: AT4G35180.
AGI-TIGR (Aug. 5, 2001) TAIR Gene Model: AT5G18470.
AGI-TIGR (Jan. 30, 2001) TAIR Gene Model: AT5G48540.
AGI-TIGR (Jan. 30, 2001) TAIR Gene Model: AT5G61160.
AGI-TIGR (Jan. 29, 2001) TAIR Gene Model: AT1G30700.
AGI-TIGR (Jan. 25, 2001) TAIR Gene Model: AT2G29460.
AGI-TIGR (Jan. 25, 2001) TAIR Gene Model: AT2G43620.
AGI-TIGR (Sep. 8, 2000) TAIR Gene Model: AT3G02840.
AGI-TIGR (Sep. 8, 2000) TAIR Gene Model: AT3G26830.
AGI-TIGR (Jan. 29, 2001) TAIR Gene Model: AT4G37370.
AGI-TIGR (Jan. 30, 2001) TAIR Gene Model: AT5G12930.
AGI-TIGR (Aug. 5, 2001) TAIR Gene Model: AT5G24110.
International Search Report mailed Apr. 17, 2008, for PCT Application No. PCT/US07/09890 filed Apr. 23, 2007, 4 pages.

* cited by examiner

*Primary Examiner* — Medina A Ibrahim
(74) *Attorney, Agent, or Firm* — Jeffrey M. Libby; Yifan Mao

(57) ABSTRACT

Disease-inducible promoter sequences have been identified that may be used to produce transgenic plants that are both more resistant to disease than control plants, and are wild-type or nearly wild type in appearance. Any of these disease-inducible promoters may be incorporated into expression vectors that each comprise a defense response protein operably linked to the promoter. The expression vectors can be introduced into plants and the defense response protein then ectopically expressed. Transgenic plants transformed with many of these expression vectors have been shown to be more resistant to disease, in some cases, to more than one type of pathogen, and yet are similar to wild type plants in their morphology and development.

15 Claims, 6 Drawing Sheets

SEQUENCE LISTING

<160> NUMBER OF SEQ ID NOS: 98

<210> SEQ ID NO 1
<211> LENGTH: 707
<212> TYPE: DNA
<213> ORGANISM: Arabidopsis thaliana

```
<220> FEATURE:
<223> OTHER INFORMATION: prAT1G16420 disease inducible promoter

<400> SEQUENCE: 1
atattgacta ttggacctta catattccga ttgtgtttgc tatttactac ggactaccgt      60 tttgttttg tctcactttg ataattggtg aattttcat ttttggatca gctaagtgcg      120
acccaaacag aaattcaaaa gtcaagagca taatttagt ttcctaaaat aggaattaat      180
ttatggatct tagattcaca accgcatgtg gaataattag taaagaaaat gccagccttt      240
ttattatttt ttctttgtca acaagctaat gccaactctt ttaaaatgaa tgaaacctac      300
tcatataatt ccttttggc cacccgtaga ctattccaga cgattaactt aatgacactc      360 atgtttttt ccttaataat agaccatagt ccattaacac tttcttttta ttaagagtaa      420
catgagagtt atattaacat ttgataataa aaacgacaat ggaaatagcc gccactcaaa      480
aaagaaagac caaggaaaaa attaaaaatg agacgtaaaa ggccaataac agcaaaccac      540
acaaagtttc tcttaggaga agaggcaaaa taacagtcaa gcatgttggt ccgtcttcag      600
acctttcgtg gtagtttaaa tgctaagtct ttcgtttata aataaagtga aaaataaatg      660
caattcataa agaaaaaaca aaggtataat tcattcattc gtcaatg                    707

<210> SEQ ID NO 2
<211> LENGTH: 1203
<212> TYPE: DNA
<213> ORGANISM: Arabidopsis thaliana
<220> FEATURE:
<223> OTHER INFORMATION: prAT1G26380 disease inducible promoter

<400> SEQUENCE: 2
gtttagtggt aaaggctatt cggagtaacc ttcagcactc aggttcaaat gtcaagaaaa      60
gctaattttt cataatatat atatatat atatatat atatatat atatatat      120 atatttttta ctaaaacaaa tctgaaattt aaattattat cataaagcta cttctttatt      180
ttagttactt gtagtcttaa aatacttagg gacggtttat attaagtcac ataaaaatca      240
tgaatcattc tattatatac taaaagtata aaccagaatt tatcagtagt atcatagttc      300
atcaagaata tcacatttca tatcaaactt tcagtatata tacgaatgtc tgataaataa      360
gttagaaaaa aaaactaaaa taattgtgaa gcataacaat tcacaaatca aaattaactt      420 gaaaacatc taattaaaac aaaacaaaaa aaaagatag ttacatgcgt aaataggttt      480
aagtctacat aaattaatat aacagtagac gcagacacaa tttaatggtg gtctgattta      540
acgatgacgg ataggatcga catttctact ataagaaaag tcaatcgcac ttttaaatta      600
aaagataagt tatgtatcaa aatttctcgg ccatcttaaa ataatgggaa aataataata      660
tagtcattag tattttacaa caacgtagcc ttataaaatt tgaattcaac gagggggac      720 aaagaaaaca aaggattcaa agagaagaga gaggaaaatt cagtgcattc tacaaataca      780
tttggcataa aattcaacaa tacttaatcg caattatttc aattagtaga tagctaggtt      840
tggtcaaaat atgaatgaag tcttacctta ggtttccatt tataaaatct cgtggtcact      900
taaaaaatct ctgtattcaa ctacctaaaa tgatcatttg aaataaagaa gttcagttga      960
tgcgactcac cccctgatct aaattatgaa agtcatttcc cctgtactat acgtattacg     1020
tacgttgtaa tttcataact ttgttcaaaa taaacagcta cttgacgaaa agtcaaacca     1080
aattcaaaag tacaccgata tggaaaaaat ggtcaagatt gtcaagttga aattattgtc     1140
tccatatata ttggtattct ataaattaca agtagaggc ataatgaacc aaacagcaaa     1200
atg                                                                    1203
```

<210> SEQ ID NO 3
<211> LENGTH: 709
<212> TYPE: DNA
<213> ORGANISM: Arabidopsis thaliana
<220> FEATURE:
<223> OTHER INFORMATION: prAT1G26420 disease inducible promoter

<400> SEQUENCE: 3

| | | | | | |
|---|---|---|---|---|---|
| atattcgttt | ttataagaaa | tgaaatgaat | acagataata | tattagtagg tgctacaatc | 60 |
| tccaaagttt | gcaaaaattt | gagtttcttc | tattcggtaa | gaaactctaa tatcaaaaaa | 120 |
| tctaaatcgc | tagaaggagg | gatcgaacct | ccgaccttgt | ggttaacagc cacacgctct | 180 |
| aaccaactga | gctattccag | cttttgttaa | tatgtgttag | ttaactttta tatatcttac | 240 |
| cataacaaaa | aaaaaattca | acaaagatta | atcgtgcacc | ggggtcggg gggatatttt | 300 |
| taagataaca | ttcaacaaag | attaatcgta | ttcaacttta | ttaaattctc tatctgtatt | 360 |
| caactttttt | ccactattga | aatttgcaat | atatatacta | gatagaaact acaataatat | 420 |
| aatcccaaaa | catgcatgtc | aaatagcgaa | gtaattccat | agtcaatccc tgatcccagt | 480 |
| catgactcat | gacaacgact | tctctgtaat | agcgttggaa | atcatttcca ctagcttgtt | 540 |
| caaaccaaac | atctacatgt | tgactaaaga | aatttcaaaa | taaacctgca aaaaccaaat | 600 |
| tcaaagtaaa | cctatatgac | aaaacagaag | tcaattatat | attaatttct ctctattcta | 660 |
| taaactaaaa | tcctaataga | gacgtaagac | aaaattaaat | aaaaatatg | 709 |

<210> SEQ ID NO 4
<211> LENGTH: 1203
<212> TYPE: DNA
<213> ORGANISM: Arabidopsis thaliana
<220> FEATURE:
<223> OTHER INFORMATION: prAT1G28190 disease inducible promoter

<400> SEQUENCE: 4

| | | | | | |
|---|---|---|---|---|---|
| aggcgggagt | ggcaattcaa | aaccaaaata | aagtaatgaa | gaagcgagtc aaagtaaggc | 60 |
| aacataatta | cgtacactat | ttgatgagtc | aaacctacat | cttttctatga ccaaatttga | 120 |
| gaggtggcta | cttctcttag | gctttgcaac | ttgaaaaata | tgttccgcat ctaatctaat | 180 |
| aataggatgt | tgtcatgttc | atatgtttcg | ttgaaaaata | ttaattctaa ttaaaactcg | 240 |
| tgttaacatc | aggattggat | ttttatgttc | atagtgataa | ttaaatatct ccaagattag | 300 |
| tgtaacaaca | acaaaaaaaa | gaataatact | tatatcataa | tctcaggatg atcatgattg | 360 |
| ctcaactaag | tagggattgg | gtcaatcact | ggttaaaaga | gaagaaaaag gtgaaatgat | 420 |
| tattctagag | ttttcattaa | agttgaaata | ccttaaaacc | aagattgaaa tgtctaaaaa | 480 |
| gaacactcga | tacttccttt | taattccacc | ggtctaagtc | ttctttcatt ttatatattt | 540 |
| gtataaccta | tgccgtcac | gcacgttaaa | catagtcaaa | ttctttattc atatattatt | 600 |
| attttaatcg | cttcttaatc | acagttaaca | tacttggacc | aaacctagtc catatatcca | 660 |
| acttttaaag | catggatgtc | cgataacata | gttgaaacat | atacatataa ggtgtgcata | 720 |
| aaaatataaa | taatatgtat | gcatgaaaaa | aagaaaaat | acaaacatt actaaacgaa | 780 |
| tggaataaaa | aaaatctgta | tattaataga | tgagtatact | tattagtaaa aatttatttt | 840 |
| aaagtaaatt | gaaattagcc | aaaaagataa | agtgaaaaag | atgtaaaaaa ttgaattttt | 900 |
| cttgaaagcc | aaaaattatt | tgtttgggcc | cctatttgtt | taccaaataa aatgaaatga | 960 |
| aggagaactc | atatatttga | atatgaaaat | tgaaacaaa | cacatttta aagggagata | 1020 |
| aattctttg | tatgtaaaat | actctcagtg | tatatatata | caaaccaaaa cttcatttca | 1080 |

| | |
|---|---|
| tttgttcaca ctgaaactcc aaaactctat ctctctctct cctccacaca ccaatttctt | 1140 |
| catgaccttc ttcttctagc agagaagatt aaagaaaccc ccaaatccag cttatactaa | 1200 |
| atg | 1203 |

<210> SEQ ID NO 5
<211> LENGTH: 700
<212> TYPE: DNA
<213> ORGANISM: Arabidopsis thaliana
<220> FEATURE:
<223> OTHER INFORMATION: prAT1G56060 disease inducible promoter

<400> SEQUENCE: 5

| | |
|---|---|
| ttgtaattgt cagtcatgca ttaggttcac ttacatggta acggattatt tgtggtgttg | 60 |
| ttgatttagt aaattggaat gttgaagaat gcagccaggt cccttgaata gtgggagctc | 120 |
| cttaaaaaat attccaagtc gatagtgttt agaagatgcg ttcggtggct atttcctaag | 180 |
| gaaacccaca ttgctcattt atcacttagt ttaattatct catctataaa taaaacgtcc | 240 |
| agtttggaca ccaaatcacg aatcacttat taatctttgg tgatcttgtg tattagtttt | 300 |
| aagaggatgt catttagaga gttaataagc tgattcgtga tttaacacca ttggcccaaa | 360 |
| tacatgattg attatgggtc gtacaaggca acaataaggt tggttactta tcaaaacacc | 420 |
| ggtgagaaca cgtccattga ctcgttatga agtgttttga cctggaacct tcagagacga | 480 |
| ccagaatcaa ggacgcctcc tacttttatt tgaaacgcgt tgtgtcgtgt tcggtctggc | 540 |
| tagaaaccgg aagtttctac gaacacacct cctaacaaat tcaatatctt aaaccggaag | 600 |
| ataacgtcag aaaatgtata aatatacact ttgaattgaa gcaattcaca aaaatcattc | 660 |
| atcatctctc ttaactcatc attacacaga catagcaatg | 700 |

<210> SEQ ID NO 6
<211> LENGTH: 1203
<212> TYPE: DNA
<213> ORGANISM: Arabidopsis thaliana
<220> FEATURE:
<223> OTHER INFORMATION: prAT1G61560 disease inducible promoter

<400> SEQUENCE: 6

| | |
|---|---|
| gttcttaaga acacatttga accaatcatc gaaatatatg gtggaaatat atttctacca | 60 |
| aagatttgtt ttttaaccaa ataattgaac acaacgctaa ctgaatattt tataaaactg | 120 |
| atacagattt attaaaaatt ttgctaataa acattataaa attgctttta ccaattatag | 180 |
| gatgtattgt atctcttgga ctttaatatc gttgacgatc ttgacaaata aaaagctggc | 240 |
| gtttcattaa attggtattt acaatgagaa aaatgtgtgg gatccaaaac tggatatagg | 300 |
| attcgcttta ctgtatctgg atccgaaact ctaaaatatg atgtttctta tgatctggat | 360 |
| tttttcaaac tataaatgat ttctgaattt ccgtgtatgt caaccaatat ttaaaaacag | 420 |
| attatatttc ttaaatattt ttcagatttt ttgaaaaata ttctgtaaat tacaaatgca | 480 |
| aataaattat ttaagaccgt taaggatcaa atatgttttt agttattca aatctctcgt | 540 |
| tctctcatat cgctattttg tacttagttt agataaaagt attaagtttg gcttcttaga | 600 |
| atttgatgtt tctttttttc gttttgcta tcgactttg tttttttttt tttactatt | 660 |
| ttggtgttat ttatctattc cttaaatttt ggttttgttt ctgatactta tattttctgt | 720 |
| aatttatgtc gcaacttcaa aaataatata aatactttac attgatatta aaaaaaaaa | 780 |
| attgagctct aatgaccttt ggagctcatg ctcatctatg gaaaaaaaaa tccatgcagg | 840 |
| aagaaccaag aggaaacggt atacaaaata atattaaata aataattatt tgtcaataaa | 900 |

| | |
|---|---|
| ataaataaaa actcaccaaa gtacataaca gttcacacag catgttttta gaaaagatca | 960 |
| tatactattg gtttcaaagt cttttgacttt gaatgtttga acttttcaag gttcgcctac | 1020 |
| tcgccggtcg tctcctttaa ccttcgtctc tgtgtttata taagaacata tacgtatttg | 1080 |
| atgattacaa aaagacaatt ctttatcctt ctttagattt ctgtggaaag ttcactatttt | 1140 |
| attaggagag acaatttcaa aaggaaagc ttttttgcttg aactgttct gtgagttcta | 1200 |
| atg | 1203 |

<210> SEQ ID NO 7
<211> LENGTH: 1219
<212> TYPE: DNA
<213> ORGANISM: Arabidopsis thaliana
<220> FEATURE:
<223> OTHER INFORMATION: prAT5G24090 disease inducible promoter

<400> SEQUENCE: 7

| | |
|---|---|
| aaatggtcca gttttggccc aaatatttaa caacatttgg gttacgagta tttgcccttt | 60 |
| acaaatggat caacaatctc cctggatcaa tatttagtgg ccggtttcat gaatcaacat | 120 |
| attctttttt tttttttgtc taagaatca acatattcta aatcaccaaa acactttggt | 180 |
| caacaatttt cgacaatata tggaaattag gttggattat catgcgactt ttttctgatt | 240 |
| aattttatgt attttaatt tacgatgtaa ttccgactac taatttgtat tatgataact | 300 |
| ttacattttc catactactc aagtccaagt aaaatactat tgtatatata tcttggatt | 360 |
| ttacataaat taatgggggag gcctaataaa atatactcgg agtatatcat ttgactttga | 420 |
| aatttatcga gtcaaatcaa tgattgtatt tttggtaaaa acaattatta tgaagacttt | 480 |
| gaaagttttt aatgatttta atttcaaaaa ttagtaaatg ctggtctggt tatccatcca | 540 |
| ttggaagaga aaataagacc ttttcaaagc tagttgataa aaaaagttct cggtcctatc | 600 |
| cctcatctta taaagaaatt attaatacgt ttagggattc aattcacaga gatttaaaa | 660 |
| acaaatggaa aataggatat taccataata attatggttc aacaacaatt tcgatttcta | 720 |
| atttgaataa tggaaattta gatcaaaaat agttccgact catagataaa ttgaaatgtg | 780 |
| ccaaatgtca cgtaaaccag caagaggaca aagtcaacac cacaagagac gacgacgagc | 840 |
| acagtgtgag gttatgatat ataccctctg cgagactgcg actgctatta ctgatttgat | 900 |
| cccaagtttt ttttttttt ttgaaatta tttttctt atacacaatt acatagtggt | 960 |
| aagagattct agatggcttc ttaatgtttg agatttatat ctagtttaag taggaaagct | 1020 |
| atattatttg aagaaagaaa aaaacaacca atcaaagtca tgcaatgtgt gtgagagaca | 1080 |
| ttataacata catagataag atataaaaat taaagcaaac aaaagtcata ttttacttct | 1140 |
| tttataaaaa aagaagttaa gcaataacaa acaaacacat aaccacaaag aagacaaaac | 1200 |
| atctttaacc aaaaacatg | 1219 |

<210> SEQ ID NO 8
<211> LENGTH: 1206
<212> TYPE: DNA
<213> ORGANISM: Arabidopsis thaliana
<220> FEATURE:
<223> OTHER INFORMATION: prAT5G62150 disease inducible promoter

<400> SEQUENCE: 8

| | |
|---|---|
| ggtatatgca cgacaggaca accgatacaa tgacagttgg ttccaaaaaa aaagtttaat | 60 |
| cctaaatata tgaataatcg aatcgatcaa taacacgttg acaaaaaacg aacaaataat | 120 |
| cacactgatg aaccactta taatgaacag agaattttgt aatctgaaaa ttttgaaagt | 180 |

```
caagaggtta atcaagtaat tatagaaagg tagttgtaac gttggctttt gtggaactaa       240
taacttacgt gtctttaaac ggcggctact ttggaaggct acgtttctta atttgaacct       300
cattttctcc attttccttc gtttatacga tatcttttc  aaaaagtga cccaataacc       360 acacatataa catatttagt ataactttga atataaacga atcaatgata tctgaatttt       420
attttgattt tgatcttgat ttttgttgtt ttttgtcgag gctattgcct tgccactttg       480
gatgaaggaa cccggctaag gtaagacccc ctgcctaata ttagcctccg gcgaattttg       540
cactcagaaa ttacattatg ttatagtttt ggaattttag tttaaatttg taaaagtatt       600
aaaacaattg gtcaactatt atattaatta gctcaagagt gctttcaaaa acatatctta       660
aatttaataa agaaatattc caatatctta accagtacta aaagagaaga tcagaaaatt       720
tcttataaaa ctttaatcta ataaaatcat ctacgactct accattcaat attttttgt       780 tattgtttta tttacatatt tcttttaata tttacatatc tcttttcctt tttgctaaaa       840
aaaagttggc ataaaaatta ctaaatttta agcgtaaaaa aataaaatta attattgtct       900
attgccattt ttggaggatg gatatgattt ggaggaatag ttaaagaaag tgctaaaatc       960
tcctttagtg agtcacaacc gttgaccttc accgcaaggc acaagagacc aagtctctaa      1020
cccaacacaa cacaaaaccc ataaactgaa aagactaacc taccctatct tgccatataa      1080
atccctctcg agcaacgcat gttaaataaa cctaatttat acattcattc tcaaagtcaa      1140
aaggagacag ggagagagag agagagagag agaattcaaa gcgttttttt tttataaatt      1200
aaaggc                                                                 1206

<210> SEQ ID NO 9
<211> LENGTH: 1203
<212> TYPE: DNA
<213> ORGANISM: Arabidopsis thaliana
<220> FEATURE:
<223> OTHER INFORMATION: prAT2G32210 disease inducible promoter

<400> SEQUENCE: 9
tcttttcttt ttttccaatc ctttggaaaa tttaggaca  atttgttatt gtggctcaac        60
gtaaccggga ccgcacgttt gataagttat tgttttttt  tttgttaaat gcagtcttgc       120
gaccatgttg gcctgttgcg tcctcgacgc atgcattttc tgagttcgga ggaagcagtc       180
gattgtttat taaatttgac acttcatgca aatattttc  attgtatttt gcaagtagtt       240
tttgggattc gattagctta taacatttgg acctcctatt tgttgattta attatttatt       300 actactttt  ttattttatt acaacttagt ttgtaatagt aaaatttatt ctactttgtg       360
cccaaaactg tcaattgttg ttcatttaaa tttctggaat tagatttaga tacgctaaat       420
taaatcacat tttgcgttta tattcccacc taatttgaaa ccagcaatta ttcttcttca       480
taagaaaact ttcatgtgct ctctcgaaaa taaagttta  ctctaataac aacacgcact       540
ttggacgaga taaagcgatt caagtaaaat tattatggtt caaactatta tctaagatcc       600
gtttgtgtaa aacataactt ctaataacat atatattctg atctactttt gttagttttt       660
attagttaat ataagcgtta attattgttc tctcttttgc ttaacatgta aatattccca       720
tggagaaaga agtacacttt ttgctttgag aaagaataaa aaaactcttt attattacta       780
aatcaagaaa aatataaaac catgctgcat ttatcatcat tttacatatt ctatatataa       840
ggttctctaa ttcgtatact tttgtaaata gagaacaacg aattaaaaga ccaaatcgat       900
agcatcttac cttttgttg  atatttatta agagaaaaaa tcaacacatt gttattcttc       960
aagagaataa atttctggag acttagcagt taatgcaatc tgacctcacg cgttttttt      1020
```

| | |
|---|---|
| ttttgacctc acgcggtttt actaaaccga ccttcgttta cttcccttac ctctctatat | 1080 |
| atatatctct atcttcattt gcatatttca attcatttca taatcataca cctctctaca | 1140 |
| tttgttacta ctttcttcta acttgttttc aaagagaaat cacaatctat ctgttccaag | 1200 |
| atg | 1203 |

<210> SEQ ID NO 10
<211> LENGTH: 1203
<212> TYPE: DNA
<213> ORGANISM: Arabidopsis thaliana
<220> FEATURE:
<223> OTHER INFORMATION: prAT2G35930 disease inducible promoter

<400> SEQUENCE: 10

| | |
|---|---|
| tgattttgaa aaataaagag aggataatac cattttggca aaattgtata ttgtgatatt | 60 |
| catgaagacc ataaacaaaa ttatcctcga acgagatgcc atatcatcaa agtcgagaaa | 120 |
| cgatgggtta gagatttgta gttttgttga tcgtgtgatg ttgccaaact acgggttcga | 180 |
| aagtcttaaa gacctttata aaggaaatgc gtcgagtatt tgctcgaga gcctcggttg | 240 |
| ggtcagtgtc aacatgttga gtgataagct cgaggacatt agtatctatg aaagtggaaa | 300 |
| tggttatgaa gtacatgtat gagggtattg gttacaggga tatgaaagac ccatgtgcgt | 360 |
| tatatggtta tagtattcat atatcaatag taaagcgaca tcacgtgata ttttttctta | 420 |
| atgtatcaaa attccaccaa tttctatttt cattttgat taataaatac atttcacttt | 480 |
| gatagtattt agtaaatatt gatgaataat caacagaaac aaggccgtac gagaaaagtt | 540 |
| gtatactctc actattatat tttatttac gacacaacaa aatggaaaat cttaagtcaa | 600 |
| aacgggtggc aaaaatgtgt aaaaagagag gaagaatcaa tcaattaaaa gacacaaagc | 660 |
| agacagtaga cactcttgtc ttcaccaccg ccacgatcgc gaccaaatgg ctctctttat | 720 |
| attttatcac aattttctta tccgtttgtt acaatctctc tttgaaaagt caaacctttt | 780 |
| catacgtctc acgtgttctt ttttcttcac ccaactcatc agcgaaaata aaggtcaaa | 840 |
| tctatgttcc tcgttcgttc cttctatgag taaataatac taataaactt tattaaatag | 900 |
| gggcagattt tttctttttt tagcatatag ttataggac agctttacaa agagtgtgta | 960 |
| ataactaata atatttgtat tttccgtgtt ttgactttt taataattgt gaattttga | 1020 |
| catctccttt atatttaaac ccaacctcct ttctctcttc ctcctaactt attcaaacca | 1080 |
| attcacatct tcccaaaccc aactactaca acttgtatta agaaaaagat atattccctt | 1140 |
| agcttctttg atcaatatat tcgtcagggt tctcgtcaaa gtcctcagca tcttcatcat | 1200 |
| atg | 1203 |

<210> SEQ ID NO 11
<211> LENGTH: 1203
<212> TYPE: DNA
<213> ORGANISM: Arabidopsis thaliana
<220> FEATURE:
<223> OTHER INFORMATION: prAT2G35980 disease inducible promoter

<400> SEQUENCE: 11

| | |
|---|---|
| ggacgagcag aatagtgggg ttttcacgtt gactatatgc gttgatggac gcgtgaggtg | 60 |
| gaaggtcggg actcttacta tagggaatta tcatctccat gttcgttgtc aggcgttcat | 120 |
| aaaccaggct gataaagcag ccggagttca tgtcggcgaa acaccgtta agtacacgtt | 180 |
| gatcaataag tgcagtgtca attttagga ggtaaaagga cacaactttg acgccgtcaa | 240 |
| tgtttgcttt tactctttct tcttcttttc attttcttc tactcggata atgttttgc | 300 |

```
ttctatatcg tttaattttc tacctttttc tgctgatcat ataacataca taaaatcaaa    360
aaatttaata tgataaattc atgttaaaag aacttgccaa ataaaaaccg atacagaatt    420
ttcttgtaaa acattcttca atcttttta tttatttttt taactttaaa tttccactta    480
aattaaaata aagaggatta caaggttaaa accccaaca tggccgcagg cctaaaaaag    540
aaagataaat tcttcaaatt tatatttacg taaaccttca aatttaataa atttaaaaa    600 accagacata attatgttga gagcatcagc aacggtaatt tctcaacttc cgtttctcaa    660
tatatgtgta aacataaata aaagtgtgaa cacaaatatt attaatattt aattgaaaag    720
tattttaatt aaaccaatga ttgaatgaca actgtgagaa acgttgtcga taagtttctc    780
ttggtttctc taaagagaaa ctttccctta cctctctcct cctttggaca tttcttttct    840
tattttattg gtgagagatt ttatgagaaa ctcccgttgg agttggtctg acacaggcgg    900
ccctaggttc tagaacggta taacgagaaa ccaacgtacg acgagagacc aaaaagtaat    960
attaacatat acgatcttac aaaaagtact cattattgga agtttggggc aacatcacaa   1020
gcctacaatt gcataatatt ctttggtcaa ttattcaatc aaatcaccgc gtaacgtgac   1080
cttaccttaa tctaataagt tgaccaacgc ataaatgaaa gtgtatataa agatgactta   1140
cataaacctc ttagccatat atccattcat tccaatataa ttctccacaa aattactatc   1200
atg                                                                1203

<210> SEQ ID NO 12
<211> LENGTH: 1203
<212> TYPE: DNA
<213> ORGANISM: Arabidopsis thaliana
<220> FEATURE:
<223> OTHER INFORMATION: prAT3G18250 disease inducible promoter

<400> SEQUENCE: 12
attaaggaac tttaattttt ccaaaaatct gaaacatact atacccaaaa atcgatgctc     60
acacctagct agttcaaact gcgtacgtca aaatatgtgg tatggacgta aagtatttta    120
taagttttgt tagaaagtta gatacttata aaataaaaaa attgatatt tttggtaaa    180 aaatggaagt ttggtatttt ttggcagttg tatacataaa taaaaatata tattacggag    240
ttatatattc ttgtttggtc aaatgtttcg gaagctttta gattacgaaa ttacataatc    300
catgatgaat taaatttggt tagtggtaga agaataagac gccaaaagaa aaagggaag    360 aacattgggt tacgtcgaaa gtcctttgat aagaatttga ttttgcatag tcaaatttgg    420
accaacaaca aaaatggagt ccacgtgaaa tagaagagag agacttaata gcttctcatg    480
cataaagtta tgaacaatca atgataacca atgataaata actaaacagt acaaaatctc    540 tgtatttta ttggatttaa caaaggccat gaacaatcac ttcaatattt taatttttt    600 taaaagacg aggcaattca agctgattta tacattatga ttaatgataa ttatattatg    660
gcatttgact tttctcacgc taatgtaaat ggtcaaaaat ccttatcttc aactaaactt    720
cctcgacaaa accttaacta gaactatgta tgtaatttat caaatattga actttaaatt    780
tctttaaaag cataatataa tcttgaccta taaaattagc ctagcctttc gaattacaag    840
ttttatattt ttaaagaaac ataatcttca actagaaatt attataaacc gggtcctatc    900
ttcatctaat atacgtgatt ccatcaaaat tccgcagtca aatgtgttta gttgagagga    960
ggagaatagt agactaaaat ggatgacttt ctggtaagtc ttgtattgca gtcttttcta   1020 tatttaaca aataagtctt ctttttcttaa aagaaaaat ttaattacaa agaaatctta   1080
ctactgaacg aataatttat caaaagtcag tggccttacg tacgaattta tcggctataa   1140
```

```
gtaggaaagc ttttcacgtt aaacaactta atctcatcca cattaactag agaaagagag    1200
atg                                                                 1203

<210> SEQ ID NO 13
<211> LENGTH: 1203
<212> TYPE: DNA
<213> ORGANISM: Arabidopsis thaliana
<220> FEATURE:
<223> OTHER INFORMATION: prAT3G63380 disease inducible promoter

<400> SEQUENCE: 13
cttaatttgt tgcatgctga gagctttgtt attactagtt accgttatga gtgagcttaa     60
ttagttgtaa tcttcccttc tacttattcc tgaaccattg tttagtttca taagatgatg    120
gttagtctat ttattctcga gcaagccatt gtatttgttg gttgggattt tgttaagctt    180
gctactgctt ttggtgcaaa cactcttgtt tctttcttat ccacatacag taactcgtga    240
tctaatgtat gtcactgagc atctctgtgt atgtatgtat atgatttgag gagtttctcg    300
acattcactt catcgcttgt atcggaattt tatgccaaat ctggtctcac ctcacgtcta    360
gttttagtgg aggtcaactt attttgtttg tttataaaaa taaagtcaac tgcttttatg    420
tcttgctgtc gtcacatgaa caaagaaaga gatgacagcg aaaatggaaa gtgctatgaa    480
gtttcggtga tcaaactcat aatgccttcg tcgtacacgc tgctccattt tattatttct    540
aaacatagat tgtggaaaaa gtagacggat tttgagtttg agtagtataa atttcacttg    600
atagatatta taccaaacca agttggtgtg aagattcaa tctaaatcct tttttttcttc    660 tttcgcttta ctatattcgc catttctttt catttgtccg tgcggactaa gcaagttggt    720
acacgcacgc tattcctcct cattctacaa tgacggcttg tccacaccat tacatcatac    780
ggctgcttta gaaattacta ccaaaatctc agattaactc tctcttttag ggcacagtgg    840
ttccaaaccg aaacacgaga caacagataa gtcaaaacac aagtacaaaa ggatgtgcgg    900
cccatgtcct ttgatcgaca tgacttcgtg tttacaacgt ttctgagtgg ttccaccgcc    960
tgaaaatatt aaactaggac aagttacttt acacgagata tttaatatt taaagcagat   1020 aaatagcaat caaaaggcgg ccaatacgga tttaaatagt accacgaagc ttagggtatt   1080
agagagagag aaatcattct ttgcgagtct taagtgtctt acaagtaaca ccacatttag   1140
ttgagagaga gcgagactct tttccttcta aaaactctct ttctttcaca caaataaagc   1200
atg                                                                 1203

<210> SEQ ID NO 14
<211> LENGTH: 910
<212> TYPE: DNA
<213> ORGANISM: Arabidopsis thaliana
<220> FEATURE:
<223> OTHER INFORMATION: prAT4G01010 disease inducible promoter

<400> SEQUENCE: 14
agcgtcattt atcgttcttt tatctacaaa aaaaaacaag atttcatgag tcagacaaga     60
caaaagccat aaacaacaca aaagtcctgc aagattgctc acttgggcgg ttgggcctat    120
atgaaaattt actatctcaa aatttaacta agagcccata aaaactgtaa gatctttgct    180
ttaaatcaca ttgtcttcat agattttgtg attcatggta gatttgtgaa gatctttggt    240 catcttttg tttacatttg gcttattgag tgtagagtgt gaacaatctg ctatgaagtt    300
ggtaaaattc tttggatcca aacctttaaa tcgtagcata tttactattt cacactgcta    360
ggatctgttt atagctgatg cattactgga atctatgatg tttactgtgt tggtctgata    420
```

```
tataacaagt tctgaatttt aaaatcaaat tcaatatcga attgggcttt taattaaggt    480
taggcccatc aaatgttttt gactctttaa taattccctc tcttttgtct tttattgtaa    540
aatgcacaca atttcgaaga aactgccaat ggagtctcca ttttccagcg ccatgccaag    600
cttgactcta cgatgatagc ttatttgact gcttcaaaaa aaaacttcag agaattaatt    660
tcgagaattt tcccaatttc agatcatcgg aaaattctta ctataatctt tcttatatcg    720
cttctctcag ttacttcaac gttctggtca gtttcggata taaatgtttt aatttcttag    780
tttccgtttc ttcttcttct tctttttttt tttttctgt tactgtaaac ttggggataa    840
cgaattaaag cgatcaaatc gatgttctta tgattcagga tccgttatag caaaaaaagc    900
ttgactcatg                                                           910
```

```
<210> SEQ ID NO 15
<211> LENGTH: 1203
<212> TYPE: DNA
<213> ORGANISM: Arabidopsis thaliana
<220> FEATURE:
<223> OTHER INFORMATION: prAT4G21390 disease inducible promoter

<400> SEQUENCE: 15
attgtatgag tatcaatata tgctttagtg ccacttgcta gtgcaatcca cttgaggttt     60
ggctgcatcg atattagata taaatactta agcgtcatgc aaaaaaaaga ttactaaata    120
attgtagggt tattatggga ttttaggcga gcaaacaaca tttaaacttt gaaggaatac    180
aatttgaaat atcaagatac gtaaaatatg tcacgtgcaa taaataaag agaagaccca     240 tccaaatcaa gtgtgcgata ctttgaccat atgagtcaat gtggcggcca aaggcaacaa    300
gcatatctaa tctaagtatt atataactaa gcaaatattc cactaaacta gtatacaaag    360
ccaactgctc cactaattgc ctgacatact tatttatttt caaatttggt aaccacacct    420
atagcttata cattttcttc gatggcctta tacaatagga atatactatt accttctcat    480
tgttcttatt atcatcaacc atttgataaa tcctcatcac tcttaaacat tgactatgaa    540
ctaaggacgt cagaagtagt ccatacaaga tatgaatggt tggatcgtcc taagtcattg    600
tattaatata cgtttctaat caatggaaac tatataattg taatataatt tttactaaat    660
catgtaactt gaaaacctaa ctttctttct taataaaaat tgaaccgcta aagtatctaa    720
tccatcatgt gtcaactgac accgtccaaa atcctcttag agatgtaaga aaaagtttca    780
aaacaattag gtcagccacc aatcacatat ttctatgcag gttgtataat cttgaaaaag    840
aacaaaaaaa gtagatgaca aaaagaatt aaaagacaat aataataata ccttataaag    900
atgataataa ttcaaacagt ttgacctttt tatttcaatt ctctggtcca actttccaac    960
ctgacgagac aaaaatatag aaacttctca acagcaataa aacagcaacc tttccttttt   1020
gtatcccttc tcctttgtca cctctcctct tactttttta tcaataggaa gtttccgcca   1080
ttgtgacaga cacagttcct ctgtttctct tctttcatct ttaagcaaac ctcaaaaacc   1140
aatcctttat tacgaagatc ctcacttgtg tcttcttctc caacactaaa ccccaagaaa   1200
atg                                                                 1203
```

```
<210> SEQ ID NO 16
<211> LENGTH: 1203
<212> TYPE: DNA
<213> ORGANISM: Arabidopsis thaliana
<220> FEATURE:
<223> OTHER INFORMATION: prAT4G35110 disease inducible promoter

<400> SEQUENCE: 16
```

```
ctaaaaatct cactcgtatt tgtataaccg tcccacgttg ttgtccactt ctggaagata      60
agtgaggtgt gtgattgatt gccgtttcca acctcttttc aattaaatgc ttctctctat     120
cttcaattgg taatattggc tttggtcaat tcatcatcat catcatatta ttattatacc     180
aaagacaatg tcacatgaac cttataatat acacaactgt tataccttat aaacaaaaat     240
aaaaatcaac atttttattca ttttttctccg ctcatcacat ttctctccct cttccgattc   300
```
(Note: some spacing approximated)

```
tcctggtata tctctctctc tctttctctt tatttctctg tttgttgatt gattgcattt     360
ttgtgtgaat taaaagtttg gttctttgat ccacaaatag attcttgatc tcgatcagaa     420
tcgtgggttt gcttttgttt taagaattaa ttcaatgatc gatgatgaaa ctgattgata     480
ctgttttatt gtcatatgct ctgtttcttt gctctgttct aaggaaattt tgtgacaaac     540
gacaatcatg gaaaacgaaa tttcaaccta ttaaaaaaat attatccaca agggtgggcc     600
ttggaagttt ttgtctgttc aagaaaacaa gccggtcaaa ataatctacc ttttaactct     660
ggtctaagtc aataactgag tgcttccacc gttgaaattt agtatctcac tggaaaattg     720
tacttggaaa ttgcatggtc ggtccatgaa agtattaagg agaagaaaca aaccaaaagt     780 cgtcttttg tatctctcta tacctataca ttttatgatt tgattggttt tgtgggggatc     840 aatttcacta ttactcgtaa gaaatttctt tatggatatg ttttggtgaa tctctctctg     900
cttctcacaa tctccctctt tacttttttt ctttcatcat ataaagggtt ggtgaaatat     960
gaatggaatc caatttcgtt gggaggttgt tgtatattat aagttttag tgtctaatct    1020 ttttgaacta tttgttgaaa ttaaggtgta aggtttgac cacttactta cccttaatgt    1080
gatatgttca gtcctttgac accacaaatt tgaagttctt gtgttgttct ttgagtttgt    1140
cttctttgag ctgattagtt atcttgattt tgttgcagtt gttccattca tcaaaaagct    1200
atg                                                                  1203
```

<210> SEQ ID NO 17
<211> LENGTH: 1001
<212> TYPE: DNA
<213> ORGANISM: Arabidopsis thaliana
<220> FEATURE:
<223> OTHER INFORMATION: prAT5G22530 disease inducible promoter

<400> SEQUENCE: 17

```
atttcttaca aacctctaaa cctttatgat gtttctagag gaccgggaaa tatattgcat      60
gcacccgtaa actacctttc aattttctac ataagtcact tcaacacaac atttgatggc     120
caaaatgtaa actgtgatta gcttactcct taaagagtga acaaagttg cagaagtgac      180 tctatttgaa ccttactctt tatctgataa tagagagaca ttaccaaagt ataaaagagt     240
ttagtaatcc taacgtgtct ttgctaggag ttacaaaaaa aggagtcacc tttgatggct     300
tggataatta aagacttta gtagtccttt tggactaat gaaagactaa agaaacgact      360
tttgacccaa aaaaaaaaa aaaaaagac ttaagaaacg actcttggac tacggcctaa     420
aaatttagta cttttagtct ccaccaactc tttcttatta tataataat tttgcctaca     480 caatttaga caaaacttcc taaggtata acataattgc ctagaagatg acataatttt      540
tacacatttt tgttgaatc tgcataatgc gacacagttt aagaagaccg ttaagataa      600 cataacttcc taaacttatg cagtctacaa gatgacataa tttgcacatt ttgaaagcaa     660
aaattggatt tatggcattt tagacaaaac ttcctaaagg taaagttttt acaaagtgag     720
ttgcgtggac ttagtatact tttttagttt tttttttgc cctctcttt tggtaatttc      780 ctgcaagtga gtggtggaag aaaggaagct gcgtggagtc ccaaaaatta aaattgcaga    840
```

```
aaaacaggtc ttataataat cagcttaata gctcaggtct cttttttctca ttctgaagat    900 taaacatctt caaggaacct aatctttgtc tctggtttta ccttcgacaa acaagcacac    960
atattgtttg ttaaaaaatc atctatcccc caagaaaaat g                       1001
```

<210> SEQ ID NO 18
<211> LENGTH: 1203
<212> TYPE: DNA
<213> ORGANISM: Arabidopsis thaliana
<220> FEATURE:
<223> OTHER INFORMATION: prAT5G64905 disease inducible promoter

<400> SEQUENCE: 18

```
taaagttaga tgttataaaa taaaataaac aaaaaccttaa acgcagtga taatcatcct     60 atcacaattc acaacgtgca ttatgaatgg taatattata tacaaagttg acgagtgctc    120
tctatgagta acgcatgatc gctctatgat ttaataaaat atactccacg aggagcagaa    180
gcaacaccaa cttcgaatat aaaacacatt taacaatctt cactgtgact ttagacatca    240
tgattttttt ggtgttcttt ttttaaaaaa ctcataatct ggtgataagt ctcgtagtta    300
cctcatcgta gaaccacaat ttagtatta cacaagaagg tatggtctga ttaaagtttg     360
ggggtctttg taattaggcc tacaataatc attcacaaat ttgaaatatt acaatttatg    420
agggaccaca cacctaaaaa aggcataaat gcattatgcc cagtggcgac gaaaaaagtg    480 cattaaaacca aggaatata tgtttgattt ttatttaat gtgggaatgg gatatgcaat     540
attacaatta tgatattatc tgaaatttta tatctttaca aaatttgatt ttcaaactta    600
aattctatag tatgatctac atgaacactt tatattctta tgcaagaaaa acaagtcctt    660
tgtccaatca ttgacctctt aattgaattt gaaatattta acaaagtacc caatagataa    720
ttcttttgtt cttgttaaat tagattttca aaatactaag ctttagcatt aatttgaata    780
atcaaagatc ttcctttgaa ttacctattc aacatttgtt taataactta attcaaacaa    840
aaaccaaaga agagcgtgaa ttgactttga ccaaaaccaa attctctcaa gagttgctgc    900 catatttga ccgcgcgcca cgtagattag agtcaaaatt gttattttat tcacttcaac    960
ataaaaccaa ataagcatta tcggttttca acataccggc accaactttt ccaaagtctg   1020
tatgtaccta acaaaaccgg tttatcatag aaacggtcaa cacaccaaaa atagttgacc   1080
aacaactacc caagtgatat cccttttaaaa ggagtcgcat atgtgttacc aagttccatc   1140
atcaacctaa taacacacaa cactaaatct ctttcccaaa aaaagattaa gaagtcaacg   1200
atg                                                                 1203
```

<210> SEQ ID NO 19
<211> LENGTH: 1203
<212> TYPE: DNA
<213> ORGANISM: Arabidopsis thaliana
<220> FEATURE:
<223> OTHER INFORMATION: prAT1G02360 disease inducible promoter

<400> SEQUENCE: 19

```
tttagtcacg tatttcataa ttatgtaaac actagtcact aatcgacaga atatgaataa     60
atccacagta ataagaaatt acaatgaatg tcagtttttt agaaggatta caaatatttc    120
tgtttgaatg tcttttgtaa cattatcttc ttcgaaagat gagatttgtt tcatagagat    180
tgtgattttt ttttttttgg taaaaggtta aatttatac taattttctg attttttctg    240
tacattgttg atacaactta ttaaaaaagaa gaatttaaaa agtttcatag agattgtgat    300 ttttttaaaaa agtttaatca tgtatttgga atggacctaa aacacataaa aacggaagac   360
```

```
ttagttgata tgatagtaag gaaccgaaat ttagttttta ttttggatg agaaatcaga        420 aaaagaaacg agtttattgt caaaaaacat ttttgtcaac ttttgcacaa cttaaagtgt        480
tgtaatttgt ttcggctctg aaataggaac atataataaa atgtatatac aactttacca        540
attagttagc cgccgaacga gattttttg tgtagattcc accacattaa taaaaaatac         600
gaatgagtct tccatcaaga taaaataatg agattttcca tagcaagaat gagtcttcaa        660
gcattaaaaa ttgaaatcag tcttttcgg taatactgct acgtcgaccg aataagaata         720
tcgtcatcca ctatcatttt aatcgtaata cacactatct atatcattca atgattatat        780
tgataagttg ttttttatttt gtatgatctc ggtttcatat taagtaatgt cagctaaaaa      840
aaatgtcatt ttagtgaaaa gccgttattt gttttttct ctacaataaa aataattgc         900 ttttgttgtt ttttccccct tcacgtattc gcttttgtt gttgtcttga tatctaatct        960
aattaaggtg taaactatat gaaaaattat accaaaaact atagaaaaag tttcacttaa      1020
cgtgaaagaa gcatcgtttg atgaatgaaa acacatgaga gcatgtataa acgaaccttc     1080
agaccaatga aaaaagtc caccgttaaa gtcaaagtc aacgcgttga tcatttacac        1140
atctatataa caaactcatc ttcttacacc aaaaccatca agatcgatcc ctctctaaaa    1200
atg                                                                    1203
```

<210> SEQ ID NO 20
<211> LENGTH: 942
<212> TYPE: DNA
<213> ORGANISM: Arabidopsis thaliana
<220> FEATURE:
<223> OTHER INFORMATION: prAT1G24140 disease inducible promoter

<400> SEQUENCE: 20

```
tgtaattaaa atctgtaact aaaatgaatt agtcagtcaa aaatatcata actacgaaat         60
aaatgtacac taaacactat caaacgtccc ttagtttaga ttttggttaa taaagctatg        120
cgtttacagg cttctaagtt ttaataatgt tggtgcaaac gtggttgaac taattctgaa        180 aacaatttttt agcctaaatg gatctaacat gaaaatctac attttctgt ttatatgtat        240 cctaattctg tttagaaagg gcttcaaact tttggcccaa aactttatat gcatgtatga        300
tatatcaatt aatttaccg atggagactt gcatgttata cccattacag gaaaaaatta        360
gatagcctaa caaacaagtc atggcgttac tcgtgtaagg tggagatttt acgttgattt        420
tttcaaccaa taacaacaac ctccggaaaa attatcacaa aaagaaaaaa gaccaattca        480
aacattcaac gacccaaaaa aaacaaaaac actttcaacc aatttagttg attctgccgc        540
cttcaaccat ttttgttgca tggttctttt tccaactttg catttaaccg gtccttttacc      600 accggtcaat cacaatttct agtcatccaa gactaaatcg ggcctaatct attgcaccaa       660
gccaccaatc aactttaatt atccataaaa cgacactatc tattggcaga agcttcatta      720
gtctttttct tcgtgagacc ctttgaaacg aggacggagg aagttccctt tgaataatgc      780
agcattttca acatagaaaa ttctccaaac gcaacgcaga aatgacctct gctttctcca     840 acgtcaaaact tgtttagttt tatctatgtc atctctctaa ttctcttgta aatctcaata    900
atacctcttc acttaatctt tttaatattt ctcttttgga tg                         942
```

<210> SEQ ID NO 21
<211> LENGTH: 667
<212> TYPE: DNA
<213> ORGANISM: Arabidopsis thaliana
<220> FEATURE:
<223> OTHER INFORMATION: prAT1G24145 disease inducible promoter

<400> SEQUENCE: 21

```
ggggggtactg tttgctaatt ttggaatatt tttgctaatt tcatgatttt ttttgttaat      60
tatgggactt aataataatt taaaaaaaca tagaaaacgt aaaaatttga gacccaatat     120
aaatgtttca acattatgcg taaaaggaca ggccttccta aaattagaac attttatatg     180
atatcctctt aagtcttaag tactatcgaa gccggagatt tctaagtttt acttttacta     240
attaagctat tgacacttga taaatgccat attttttgcat tccctaaaac ctcaaaactc    300
tctaaacacg ttttttgtgga catattaaaa tagtgtattt tgtagtctct tccaggtttc    360
ttccttcttg tcaacgtcgc acaagtccgt ttacggatat gggtgaataa ttgaatatta    420
tccatgtttc cttattagca gtcgctattg tgggtttctt tttggtagtc taatttatta    480
tttacttctt taaaatgggg aaacagatac aaagttgcat tacatatata acgcaataca    540
attagatccc atttgaccga gtaaacgcta agatccacac aaactcaatc gtcaactcct    600
ctctcttctc tattctatat agttgcgtga atgtaatga aagtgatcat cattcacttc     660
taagatg                                                                667
```

<210> SEQ ID NO 22
<211> LENGTH: 1203
<212> TYPE: DNA
<213> ORGANISM: Arabidopsis thaliana
<220> FEATURE:
<223> OTHER INFORMATION: prAT1G35230 disease inducible promoter

<400> SEQUENCE: 22

```
cttctaagaa tagttgcaag cctttaaata ctccgacaaa tctggcatta gccgaaagat      60
attccaaact caaatcgga tcagatagtg tggtggtcta atttttacctg gatcgggaga    120
tgtccactct gtaccacctt gatgcatttt tactgatact gatcagatca accgatataa    180
tatatatata aaaaagaaa gttcgtccaa aaggaatcat tattttctta accaatagaa     240
tataggaaat aataggataa atctatatta gtggacaggt aatagaatgc tttcattcac    300
attgaaatca tattgtaata agcacacttt tcttatcaaa aaaaaaaagg caaaagaaa     360
tggccacgca ataaaatcat tagggtaagt tgaattttgg tccataatat tataaattaa    420
tttaatctcg aaagcttaat cttatgatct catgtgatct ttattgaatt tacttacttc    480
catagagttt tgtatttttgt ctaaggaaag aaaaaaaaag tctgccagct ttggaacgcc    540
gcccattcct ctagactttc ttggaaacaa cgcgttgttc ttgttggggt cgacgaagac    600
tcactaaatc catccgacga ctcagatttt atcttggctt cttttgatgt gtacacatat    660
ccaccctgat ttgattccca aagccaaaag cctgaacaat gtagtgtaga agaagtgacg    720
ggaaaaaacg gtaatgaatc cacaatggat atttacagaa agaaataaaa ttatatagat    780
tatagagaag caaaattatg caaataatct ttatttaata ctattaaaag agtagctgtt    840
ggaaactata acaggtaatt taaaatattt tacaagttca acatataata attttgaaat    900
tcagtccaac ataactatca gtatggaaat aagccaaaca aattactcaa ataagaaat    960
atgttttcac attattattt aaacattttt agtcatttgt ttggcttatt tccaaaacga   1020
tatttatgtt ggacttgttt tcaaagtat tatgttgaac ttgtaaaaaa aatttatata   1080
gctgttgaaa tttccaagaa aataaggttt tacacctaaa cccttccact atatatataa   1140
accccacttt tgtctctata tctttactaa tttcttaaac cctctcaaca atacgtaaca   1200
atg                                                                  1203
```

<210> SEQ ID NO 23
<211> LENGTH: 1203
<212> TYPE: DNA
<213> ORGANISM: Arabidopsis thaliana
<220> FEATURE:
<223> OTHER INFORMATION: prAT1G57630 disease inducible promoter

<400> SEQUENCE: 23

| aagcagagat | gaggattgtg | agtgaaaaaa | caaactcgag | agtcgcatgg | tacagtataa | 60 |
| tgtcgctggg | gatttgcatt | gtggtctctg | gtttacagat | tttgtacttg | aagcaatact | 120 |
| ttgaaaagaa | gaagcttatt | tagatcatgg | atagtttctt | gttgaagatt | actagaacca | 180 |
| acagtttgct | ctgctttctt | tctcttgatc | ttctctttgg | aactgttagt | gtaaaatttt | 240 |
| gttcactcat | ttaacttgta | atttgtctcc | tattattaca | tataacatat | aactagactc | 300 |
| taattatagg | aattgcaact | aaatttctct | tgataaaaat | aataatgaat | ttctttggca | 360 |
| tgtgttttt | tatattatct | gaactgaacc | aaattgcaga | attgtgactt | gagaaaaaca | 420 |
| gaggactctg | ttgatatgaa | gtctcatagt | ataaacagag | gactctatgt | gaaacagagt | 480 |
| tacgaaaaat | tctaaagtaa | tgaaaaaaac | acattgtggt | tttatctgga | ttagaaaagc | 540 |
| cttcatatat | tttatctgac | aacattaaga | agcttaggag | atttcttggg | atgcaagcat | 600 |
| tttgtaacct | gtttttgct | acataacatg | acattgtgtt | ccagctaggt | caaagagta | 660 |
| ttacagcatt | attcacataa | cacacagagc | acaaagttaa | atctttgtag | agtttctata | 720 |
| agacgacaag | aacatatgtc | cacaatacga | aacataggct | gatgcatgtg | gcggggcaa | 780 |
| ctgtggtgga | gaggttggtc | ataaatttgg | ggcgtacacg | gaaactcaga | cttttcctca | 840 |
| atacaaaaca | tagtctgatg | cattacgtcg | tcggtgcatg | attgtcaagg | tagacgccgc | 900 |
| aaaataagctt | ctcggaaaaa | ctctatacat | gtgaacgtag | actagtctat | ggaatccttt | 960 |
| tttgctatga | ctaagtccaa | acattgaact | tattgcttgg | aaactgcata | tatttgaatt | 1020 |
| tagattttga | tggagacttt | cgttttcttc | gctgaaattg | cttgtgcgtt | tcattgctat | 1080 |
| ttccttctta | gaactagaga | accacaacca | ttttctgagt | tattacttcc | tacatagctc | 1140 |
| tataacctct | attattactt | tattagatct | ctgatcttaa | atcgtctctc | tgtcgtagta | 1200 |
| atg | | | | | | 1203 |

<210> SEQ ID NO 24
<211> LENGTH: 1203
<212> TYPE: DNA
<213> ORGANISM: Arabidopsis thaliana
<220> FEATURE:
<223> OTHER INFORMATION: prAT1G67810 disease inducible promoter

<400> SEQUENCE: 24

| agtgggaagt | atacgaaacg | aattatttaa | gatatttaat | ggaaaaaagt | tttagaaaca | 60 |
| agtaaaaaat | tggttttggt | cagtacactc | aagtgtagcc | gtaagctatg | acgacgaaat | 120 |
| gaaaacaact | ttaattatt | tcccaagcct | ctttccgaca | gtatgggct | ctaaaagtat | 180 |
| atcactaatt | cagtagtcga | atcgaatatg | cctttgttct | ttcccttta | aatccataat | 240 |
| ttatttctaa | aataataaaa | aggagattgt | cactggagaa | gccgcctcaa | atgatgtcca | 300 |
| tatcgcatca | taacatttaa | cgtcacacga | taaaacaaaa | catttcgtat | tttgttttgc | 360 |
| aatctatttta | gtaattgcat | tattagtagt | ggcctatctc | ttttgaagtt | gaagtctct | 420 |
| agttgacttg | gtcgtatttg | tatcattgtc | acatataagt | gaaaattaag | atggacattt | 480 |
| ccgatatat | tagctaaatt | aaatcattct | aattttttt | accagatatt | caaaattcca | 540 |
| actcatttag | agtttcacgt | tggcatccaa | gtacttggat | tagctttcga | ctaaacaaga | 600 |

```
aattttacgt ttttgcatag attataaaat tagtttgaaa atttggttca aaaatttcct    660
gattaaaaga atataacgaa gcattttata atgatgacaa tgattcataa ttttgtaag    720 tgcttcagtt gctacctaac tcaaagtcgc aacttatatt ctaacagttt catcattta    780 attttctaaa aaaaaaaaa aatcaaagac caaaaaattc taaattaaac ctataatagt    840
ttcctttaac caaaaaaaaa aaacctatac tagtttcaag gctcgtagag gaagttagat    900
tacttaccat ttaaaaatct acaatttaaa tatataattt ttttaaagta ttttataaaa    960
taacattaca agatagatct tttttttttt ggtaaaaaat aagatagatt atatatagat   1020
agatcaataa acataaaaat agttttggcg cgttatagaa aggctctatg catctaatca   1080
ctatcctctc tccgtcgcgt agttcaagga gttctccttt gattatcctt aaatatctct   1140
cttctctcgt tttcttctac ctcctcctcc catttctttt cattgccctt gttacggaac   1200
atg                                                                 1203

<210> SEQ ID NO 25
<211> LENGTH: 1203
<212> TYPE: DNA
<213> ORGANISM: Arabidopsis thaliana
<220> FEATURE:
<223> OTHER INFORMATION: prAT4G18250 disease inducible promoter

<400> SEQUENCE: 25
tcaatacaaa cacaaaggac aatttggccg agtggtctaa ggcgccagat ttaggctctg     60
gtccgaaagg gcgtgggttc aaatcccaca gttgtcattt agatttattt tttccagact    120
ttttataaga tttagagact aaaaaacttt ttaaaataag tataacatag attgttgcct    180
aaacgaatat tgttacgtaa ctgtaaggtt taactttgat tttggtccac aacagaagag    240
cttaagcctt ttacccatgt ttgatcagtt ttggatgcta agatatagag agtgtgcata    300
gtcttcactc ttcactcttc aaattgataa tgttatgttt cagtagaacg atcaacgcaa    360
atagtgaaag cctaatgagt ggccaatcat caaaattaga gcgaataaaa aggaacaaaa    420
aaaaagaaga caatgagttt aatactttt agcctcaaca agtttcaatc ttattttttt    480
tgtaagtatc tagctagttc tataaaattt atttaactta gtgattagat aaaagggaac    540
aaaaaaaaaa atgactttgg tgtttgctag cctctacctc aagtcctcaa cccatcattt    600
tatttgtgaa ttaggtagat aaaaatttaa aaacggacac ctaaaaaatc taaattctaa    660
atctgaaatt ttaaactctt ttaatttttt tctagtaaaa tgttacgaaa gtaaatcgtt    720
tgtcccataa ctgttaataa atggtaaaat cattcgataa aacagtcgtt ttttttctct    780
tttttcatga aaaacttat tcccattgcc actaaatgga attatttaga aaaaaataaa    840
atacctcttc tttcttggca agttcccgga aaaaatatg gattgggaaa aggatagtat    900
tgtagttaca tttatttcct ctatctgttt ccttccttct atttattctt gattgactct    960
catcaccaac gaatatgtac tagtaatttc tactaacaag cgaggaagaa gcaagagaaa   1020
ttataacgcg aaattcactt ctttggaacg tatatttttt tttctttcag cagccaatgg   1080
cgaaaaggct gccattgatt ttcctcctta cttcacattt tttagtatcg ggtaggattt   1140
tcttttcttg attgataata acaatggttt tttgttaatt gtttcttatt tctaagctta   1200
atg                                                                 1203

<210> SEQ ID NO 26
<211> LENGTH: 1203
<212> TYPE: DNA
<213> ORGANISM: Arabidopsis thaliana
```

```
<220> FEATURE:
<223> OTHER INFORMATION: prAT4G35180 disease inducible promoter

<400> SEQUENCE: 26
tattttaatg ttttagctgg tcatcatcaa ctcgatttaa gaaaactgaa ttcataaatt      60
tttagttgac tacttgactg gtgttcgttg actagttcac ttatttaagt ttttcttatt     120
accagaccta gaaagaaaaa aatgaaaaaa aaatcaccaa atgtccaaat gagatagcaa     180
tgtagtacta gttaatagat tgtttcttaa gtcttataga tttgtatcaa agggcttctt     240
gactgataca agtttcttcc tttaattcgg tttataatag tattgatcta aaaccaaact     300
acaaatactt acttaccact aaacttactt ttcaaacttt ggcttgaagc taaacttgaa     360
gctaattctc acttaccact agacttgaag ctacttttga aactttggtc tcacataact     420
agagttgtaa aattagatga ctagatgcct actctatata cttttttaatt attttttgctc   480 ataacaaaag tcgagtcaaa aacaactcgc acgtttatca tctttaatta actacttgat    540
taatacttat taatcgtgta tacaaagaga cgatgaagga agatcagctc aaagttgacc     600
cttgcgttga ccaaaacatc cgaagagcaa acaaagtcca attgaacaat gaacacaatc     660
taacacaaac tagtttggtt tactttttag cctggcttga gttttaagct accgaacaaa     720
attagaagac ttcgatttat accgatgggt ctcgctttcg agagtatttg aaagtgacat     780
aaccgattac gtcatctttc tcgtgtcatt aatgcttacg tcatagctaa taatttctac     840
cgttcagaat atattttctt atatggtaat tagagatatg aattgtttag tgttaaagta     900
ttgagattct cttgagcact taaacagaaa aaaacaattc cctaagaaaa ataccttcct     960 ttttttttgtt ttggaaaaag agattcaaag tcaatataca cagccaccga acaaattact   1020
ctatataaat ccaatgaaag cagagtaaac atttatatag ccatacaatt tgtggctcga    1080
cgtaaataac gcgattggag tcgttagagg aaaataaagt ttatttttgta tacaatgtct    1140 atagcattgg gaaacttatt tgatttggaa tcacaagaaa gtggtggttc tcctttattt    1200
atg                                                                  1203

<210> SEQ ID NO 27
<211> LENGTH: 1203
<212> TYPE: DNA
<213> ORGANISM: Arabidopsis thaliana
<220> FEATURE:
<223> OTHER INFORMATION: prAT5G18470 disease inducible promoter

<400> SEQUENCE: 27
aatcagaaat ctttgatccc actgacaacg tgaaaacatt tttactgtat tggttggcta      60
aatgagtttt agttattaca ccaagagatt tgagttcaaa cttcaaaata tactattttt     120
gtttgagttt gttgttcaag tattacatag ctgattacag aaaccaaaga aatataagat     180
ccaatgtact tggacttctt ttctttttttt gtcgtcaatt tcattaaatc cttaaaagga     240
ttacatggtg aaaggaaaac ccacatatac acaaagttaa agcccaatta acccaaatat     300
tgattacgat gaaagaacaa aatgggctaa aaagagacac gtgtgtacac gtggaggcat     360
ggatgaaata taagatccaa tgtacttgga cttctaaaat aacaaataat gtaacactag     420
attttagaaa acaaaaacca tccaactcga tcattcatca atattatata gagaaaacag     480
tcataatgtt agagagagac gtatgaatcg aaattcatat tactgtattt cgattaccta     540
aaaagtttcg aaaagaatt aaaagtttgt gtggaagatt ccaatacacg ttgctatcgg      600
aagaagactt ggaaaattat tcctcaagtc gttaatgctt ggaattagtg actaacaatc     660
atcattattc cattgaaaga gccgcccacg acgcgtttcc attttccaca ccagtcaaag     720
```

```
ttgatgtctc aaattagtaa ctgatttaca attttaaatt acaaaataca aagcccgtac    780
aagctaatgt aaacggaagt aaaaccaaat acattaacaa cttttagttt agctgttcaa    840
aggacagaga tatgacctca accttaaccc aatctttcgt ctgtgtttga aacttctgct    900
cgtaaagaga ctctagtaaa acccttcgga agaaattttt taggtagtcg ccatcatata    960
atttaaagct tatgagactt gttatgttac aagcagagac caaagactat tcataatcac   1020
ttatcagagt ataaaatact cttttttttgt caatcgagta taaaatactc tgatatcact   1080
tatacaaagt tctacgaaac tcattaaaga tttgagagtg tacaagggac aaaaggtgct   1140
ataaatatct cttaaaagag agctaaaagt taaggaaaca cttaaccaag caaacaacaa   1200
atg                                                                  1203
```

<210> SEQ ID NO 28
<211> LENGTH: 1203
<212> TYPE: DNA
<213> ORGANISM: Arabidopsis thaliana
<220> FEATURE:
<223> OTHER INFORMATION: prAT5G48540 disease inducible promoter

<400> SEQUENCE: 28

```
aaaatataat tattcttttta taacgatggt attattttttt gcaaaaatag aatcatataa     60
agatgagagg tgaactataa taattaataa aaaattaata tgataattta gataatgtat    120
tttgttttaa ttaaatttaa ttaattaaat tagtatttga cttttttaatt tttaaagaga    180 tgaattaatt tactctttaa attttatttc taatggcata cctatgtaat tacttacaaa    240
aaataagatt atatttaaaa tgtacttccc aaataatata gcaggaagtt ttcattttta    300
attatatatg tgccttttca tttaacaaat tttccaacat gaaaagaaga tatgttggta    360
aatggtaatc tacaaaccca aataaaaaag aatataaaaa aattttagt taaagataaa    420 tataaattct ttatcaatac tatttccata ccaacttgta aatcttcaaa ttattttgat    480
tagtatctat ctacaccaag taccggaaca agttttttgtg caatacggaa tcttcacctc    540
aaaccaagcc taacataggc attcatcaag gctgaaattg tgcacaataa cacgtacaaa    600
aaatcatcgt aaaataaata cgaacatctc tcgaaacaga gaagtggtca atggtggtta    660
tattttttct ttttttgtgg tggtgatatt atgtaatatg attagtcatt gaagaccttt    720
tgtagagaga agtggtcgat gttgcgccac tttagcgtta acgttgacgt ttggaaataa    780
gaagcaataa ataaatcgac ggtcaataat tcctgctcca tatatgttga cctcacacgtg    840 atgccatttt ggaatcttcc aacgaaaatt atttagtttt aattcaattc aatatatatt    900 ccatttttgtc tttctacaat acacaaatga aaaaaacaaa gtaaaattga ccaactaata    960 tttattttact gatttgattg gtcacaaact cacaagattt tggccacaat atagacttct   1020
cggtcaacaa aaatttgtat ttgatcataa ataaataaac aattatttcc cacttgttgt   1080
tatgcgtttt gaccgacttc taaaaaaatc aacgttctag aatagataac gttttggtat   1140
aaaatcagtc tcttcttcta gtgactcaaa acaaactgta aagtttatta agaaataata   1200
atg                                                                  1203
```

<210> SEQ ID NO 29
<211> LENGTH: 1203
<212> TYPE: DNA
<213> ORGANISM: Arabidopsis thaliana
<220> FEATURE:
<223> OTHER INFORMATION: prAT1G30700 disease inducible promoter

<400> SEQUENCE: 29

```
caatatgaaa gtcaaaccag ccgctcaaat gtatccttca tgagttcatg ttatatttca      60
gtcaatactt ttcatattta aacacttatt ataattacgt aatattttt tgcccaaaaa      120 aaaaaattac gtaatattca acatctctac cttgtagagt tccaaaacat tgtcacaaaa     180
tatttataaa gaatttattt taactaatta ggtcgttaat tgtccaaggg ttttcatag       240 ttgatatagt tctgttcaaa tatagccatc cttaatcgat tcatgggatc gtaaattact     300
acttcgagtg ttgtaaaaaa aaatgaaact tctacattac aaactcgaat ttaatgcatc     360
tggagtgata ctataaaagt agggatgctc tcaggtcgca tttgagagac acagaaatga     420
ttttaatgga attaatatat tttcagtttt tcacaaaaaa aaattgtgtt tataacaact     480
gcagattcaa tgctgatttt atgagtctca cctatagaat ttatatttct atattcatag     540
aggcagtata ggtgttgacc caacatcgaa agaaacattc gtaaaaaatt ctttggaaca     600
aggctgaaaa tttactccca aatttagcta tccgatgaag ataaatcatt taccgtttat     660
taaagaatta tcgagatttt agtccaaacc aaaagagatt atgagcctaa gattttgaat    720
ttgtattggt aaaagaaatt gaacgaaaat ttcagaaaaa aatattaata aattgaacga     780
tagagttcac ttactacata gtcaactagt gcctagctat aatagtttca aaagacaaaa    840
aaaaacaaaa tcggttaact acttccgtga cataattctc attttgattt ttgaatccag    900
tctaatttga aaagtatatt caaaatcttt aaatccatta atgataactt ttataatacg     960
ttgacacacg caattgtata tacaatattc ttgaatttta aatgtaaatt ctagaatata    1020
ttgcgatcac cacactaatc aaaatctttg ggacaacttg aacccacatt tgacttttct    1080
tggtcaaata ttttggcatc atgcatgatc ttctctataa aaaccaaaag gcctcaacga    1140
cattcataaa ctcagtcatt atatttattt ttgttgtatt tcaacgttca atctctgaaa    1200
atg                                                                  1203

<210> SEQ ID NO 30
<211> LENGTH: 878
<212> TYPE: DNA
<213> ORGANISM: Arabidopsis thaliana
<220> FEATURE:
<223> OTHER INFORMATION: prAT2G29460 disease inducible promoter

<400> SEQUENCE: 30
tctcataaca tattttgtt ctgtaattta gatgataaat tgataaccaa tttgtattat      60
tacgaagaaa aagaaaacag tttgaactat tcattaaaaa aagttattgt ttaaaaggta     120
ttttattaga ttaaatatt aaattaattg taattcactt ttggaccacg catttagcat      180
cacacgtata actttaacaa atcaggtaaa accaaatttc tttaattagg taaagaaaca    240
gaagactgaa agaaaaacta gtttggaaac aaaaaatggt atttgcagga attgtaagga    300
atttgggata ctagaaatgt atggatctaa gttagaaaaa atcaacaaaa atttgttgaa    360
tattatttat aaagttggta tgtttgagga aattgaaaaa gataaaatat atttgaatat    420
atggagagat gatataatgt gttcacggtt cattggatat ttagcagtga atgaatcaag    480
agaaagcaaa atagttattt tcttctttcc cgtcgtttta gtactttt caagcacgag      540 aacggaatca caaaaactag tcaaaaaagg cgttaaatcc tatagaacaa aaacatataa    600
gctatggttt cgaacgggaa ccaaaccata atatgcgatg cacttctaat agcaatcaaa    660
aatttgttaa tatgtacata tatattttg ttttattaaa accgtatcat actttatctg     720
cagttaaacc gcacatcttt attcggagcc tatatatcta cactgcctat atatcaaccg    780
accaaacatt cacgaaaaca aaccacataa actagtcaaa gaagaataga tgagttacat    840
```

```
tataaaaaag ttcaagtgag agaaagagag gtccaatg                                 878
```

<210> SEQ ID NO 31
<211> LENGTH: 655
<212> TYPE: DNA
<213> ORGANISM: Arabidopsis thaliana
<220> FEATURE:
<223> OTHER INFORMATION: prAT2G43620 disease inducible promoter

<400> SEQUENCE: 31

```
accagggttg gtaagactaa accgcttttt attgatatgc tggtttaatt ttgacgcatg         60
actatttgga aattgcaata attgagttgg attttttctaa ttttggttga ttttgattta      120
taaatagaaa cattttggct tcactagtca tttttctcac aattccatac aattttgtt       180
aaaaatcaaa gtaagacttt aaagaacgt tctaaatgct atattagttg accaaaaaaa       240
atgctatatt agctaacaat atcgtttgag ctaattaaca aaacttgga actattcaat        300
agaaaaatct caaacgtttg aactaatcta aacttgatta tctcaatcaa gttttttatga     360
gaatgatttt catccaagta acttggctct ttaaaatttt gattacatat tcgttttttga    420
tctgatctat gaccgacatg gaatttctca taacgacaag agaaaaaact gtgtcattga      480
cttttgttaa gtggtacaaa gtggcattga ctttgactca gaaaaagcca atcaataatc      540
gtgaaagatg tctaacactg atcaatattt caatttgaat agaccaaatt tacactataa     600
atacatcaac acaccttctt catttcttca cacaacaccc tccatacaca aaatg           655
```

<210> SEQ ID NO 32
<211> LENGTH: 1203
<212> TYPE: DNA
<213> ORGANISM: Arabidopsis thaliana
<220> FEATURE:
<223> OTHER INFORMATION: prAT3G02840 disease inducible promoter

<400> SEQUENCE: 32

```
ctacgatgat tgaaccaact ggcttatgtt ttacctatct gcgttaaatt tcgtggtaaa         60
ctgaaccggg atgtaatgaa tccggttttg gtttgatttt ttttaaatga aaataacttt      120
ctgtggatct tttaatcgaa aataatattg aacgttacat aattgggtga aaattcgtat       180
ttatcagata tttggttttg atcgaatctt cgtgtggttt atcttagata ctcgaacttt      240
taaagcagtg tatgaatcta cgcgtaaaat atttaatgta ttgaagtaat attggaaaaa     300
caatgacgcg gggaaaagta aacaaacacg gacccgacga cggataagcg accaagcccg      360
agtcgcatcg tcttggtctt aagtctttcc ctactcgttt tatcattttc ttaaactaaa       420
aactaattta atcactctta attatttact ttttctttt aattcaacta tgactaattc       480
ttattcacag aatgagtctc acatgcctac tcgtcgtact cgactccagt ccaaatgttc      540
ccatacttgt aatctatact acatatatta tacgtcatcg tcatgtatat acaagactca       600
atatataacg tccaaattaa tcaaagattt aacatgatcg ggaaccaata tctaatcatc     660
gattagatat atttaagtct agtaactaat tagtatattt tctacaaatt gtttaattaa       720
acatatagta tacagttggt aaagggggaaa cacgcgtaat ctatatgtat atattaataa      780
tatatagttc ttggtatgat cttcttagtt atttatttac taagctttct agactttaac      840
aatatttgaa tgaaaaaaaa atttaattaa ccgtcgaaaa aaagtcata aatctggacg        900
cagaatacta atccacagat ttcaacggtc aacattccaa ttcagttcac aaacctaaat      960
caaacgttcc atttcatacc ttttttctct ttcaagctta tacaaccttt gaccatgtct     1020
cactttatta ataagtacaa aaccacctta cattacatgc atatatataa ataaaacacg     1080
```

```
ttaaggaaca tatatttata caaatcccat aaaccccatt tcattcttca tcgaatagtc    1140
gaaaaatatt tgaactttct taggaaacca aaccaacaaa acaaaaagga aaacgagata    1200
atg                                                                  1203

<210> SEQ ID NO 33
<211> LENGTH: 1203
<212> TYPE: DNA
<213> ORGANISM: Arabidopsis thaliana
<220> FEATURE:
<223> OTHER INFORMATION: prAT3G26830 disease inducible promoter

<400> SEQUENCE: 33
accacaaaag gtgtgtttta taccctatca tgttttactc ttgagatatg ttctttgaca      60
ccacccacaa aatatctcta cgaaatacga agccactata tgtctcttta atttcacttt    120
ttatagtttt tttcaccgct aaaattgttg actaaaaaat atattgcata aaaataattg    180
ataatatatt tataagaaaa actatgataa gaaaaaatat aatcggttga aatgagtcat    240
gactaacaat aattaaaggt taggaaatta aagaaaata  aattctgaaa taactaaaaa    300
aaaaaaaata gaagatgatg atatatggat ccctatacta atattttgga agtacattga    360
aaaactaact ttcaaagacc caattaatta agctcattaa ggataaacat gttaaatact    420
aacttatgga cattaattaa attaaaaatt ataaaacgaa aataaattga tgacaaaaaa    480
aaaactatga attttcttat taggatttgt aatctacttt cttgaaaaaa attgaagttt    540
actgacggct tcctttttt  ggaaactcca aaataacaaa acatatgaag aagttttgga    600
atagcctttg actcaacaac tttaacaata gaaagaaaac atgtttaatt aatgttcatg    660
cacttcgtct cggctgcccc ttgtggcctg tggggttgcc gggttggctt agcttgagac    720
gacccaatac tgaatttgtt agctcggtca gtgaagtcta catgcatgat acaaaaagat    780
tgactagtgt ttaagttttt tttttttttt tttttttttt tcataaatgg tagtgtctca    840
tattagaaat ggtagtttga aaagtattca gtttgtttgt tcactttgga ttatttgatt    900
ttggttttgt taattgaatc agtttgtttt gaaaagtatt cacttttgaa aagtgttcac    960 tttaaaagt tttgttgaa aagtgttcac tttgaaaagt attctttgag aagtgctcag    1020
ttttggtttg tccacttacg attattattc acaagctaca gcggatagta gtgactagtg    1080
acttatgact ttgaataaag aatttccctc taaaggaatg aatacattat aaatagatta    1140
ttaacctaag cttgatagag aagacagaac aaaaaaaaac acaagaacag ggcaaggaaa    1200
atg                                                                  1203

<210> SEQ ID NO 34
<211> LENGTH: 1203
<212> TYPE: DNA
<213> ORGANISM: Arabidopsis thaliana
<220> FEATURE:
<223> OTHER INFORMATION: prAT5G12930 disease inducible promoter

<400> SEQUENCE: 34
tgattattca aaagacaact catgtgcccg cgcatgtgct tgacgttcgt ttgccgtgta      60
ttagaacttt aaaaactgat tcatataaat catcggtcga ttgaaatata ttaacatgga    120
ttatgatgac aacaatcatt atacaattaa gtttatgaa atgatcatcc acaaaacata    180
acttttgtcg gctattttt tgttgacgtg acaaactaaa ttagtaaact gtgttttgag    240
tgcaaaaaga tgaaaatttt gtgggattga ttgcatagaa taacacttac aaaaatgtag    300
gtagtatgca ggggagtcaa caacagacga cttttcataa ttcagaaaac gaagaaaaac    360
```

-continued

```
aaaaagaaag gtcgatttcc caaggactag ggcatagcac gtgtctatat cactggagga    420
tatatcactt agaccgttag acgtcacgtg taatcgtgta ttaatgcttg caaaatgtgg    480
ttcaatcaaa tacccaatta agggttatga gaactaatac aaaaatgtgg ttcccgtaaa    540
taatgcatga gcaagcacat gactgacatg agagatagac cagcgaataa aggttaagta    600
ttgacgcacc atgcaaagcg taacggtgaa ctggagctct actggctgag ataattcaca    660
aggtgaaggt gagatatatt ttaggagagc cagaaaggta gaacccaaga caaataaaga    720
gagagaccaa gtgagttttg gactaatgtt tttcaaagaa tgtgtctata actatttatt    780
aagttccaaa aaaagacaaa taaaagtatg attttttctat ataggactac tcgattaatc    840
ttaacaaaaa gacgaataag cagaaaacat atatgtttgt tttttcaaaa caataacctt    900
ggaaatcaaa acaccagaaa aatgtggctg tgaagaaaag tacaagagag acagtaaaaa    960
gaaaatgaac caaaaaggca aaaaaatgaa tacgtggctt caatgtagac ccagacgatg   1020
aacgtcgcat caccttcctt acgggggaaa tctcacattt tgaaattaca gaaaactcca   1080
aagaacccaa aattgaatat tgaatattga aaattgaaaa aatctctctt tgaagaattg   1140
aaatctctct tgaagacga acgaacctcg ttgattcctc cattcctctt cggctcgtcc   1200
atg                                                                 1203
```

<210> SEQ ID NO 35
<211> LENGTH: 1203
<212> TYPE: DNA
<213> ORGANISM: Arabidopsis thaliana
<220> FEATURE:
<223> OTHER INFORMATION: prAT5G24110 disease inducible promoter

<400> SEQUENCE: 35

```
taacagacat caccgaaaaa gtcgccgaaa aattgaccgg aaccacatat gtaaaaatga     60
gttccaacaa gaggcagtac aaaagaatag gcataaccgt accgcataag tgttcaagcc    120
caaggcaaag ccatatctaa aaatattttc atacaaaaag gtgtatacct aaaattttct    180
tttgaagtaa gaacaaaaaa aaagttaaaa tttatttttca tatgttctcg aaaagtatat    240
ttattctaat atgaaatggc aaataatttt gccccgctgg aatttctatg tagtttgcgt    300
ttattagagt ttgcgtttgt atttagcatt attattattt gcattgtcgt tagcttttac    360
atctgcattt agtgttatgt ttctagcttt tgctttggca tttctatttt tttttttgtta    420
gagtttgatt tgaatctat tttaagattt atatatgacg aatttattta ttatatatat    480
tatgaaattt catatgttat actatatttt tctaatgtat attgtttagt ctcataaact    540
ttttaaacgc ctagattgtc taaacgtcga ttatgggtta tatattgatt attgacacta    600
ggtgatcaat tgtcactcct tattgtctac agttatctta aacactttta tagaaactct    660
agaaatgcta tcttgtattg aatttggttc cataaatgga tcgataatta aacttgatcc    720
aaaacaaaat gaatattcca acataatgac catatttgtc tcttggaatt tctaaactca    780
atattagaat tttatagcaa aattaaaatt tacaatagaa aatcatatcc taataagaat    840
gaatagttat taacaaatta atattcgaa tgtaagttaa atgattgtga ccctaatatt    900
aaacaaaac cagatcatgt aattcaaaat ccaataaatc aaaaataaaa aggatcgaga    960
agcagagaac tggtcagcat gttggacttt ccaaattcat tgaccaaaga ctggtctcac   1020
ttctcacaaa ccacatcagc tttcttcgtt cttcagtcaa aaagtcaaac tatctctctc   1080
acacatcctc tttaaattct cctctttctc agtttccaga agccatgcaa aaataaacat   1140
agtaacaata cttaaaacta tttacaccac tttaatctta ttctccactc tttgaacgta   1200
``` atg                                                                      1203

<210> SEQ ID NO 36
<211> LENGTH: 1205
<212> TYPE: DNA
<213> ORGANISM: Arabidopsis thaliana
<220> FEATURE:
<223> OTHER INFORMATION: prAT2G18690 disease inducible promoter

<400> SEQUENCE: 36
ttgaacatgt tcgggtttga aaaccggttt atgtaactat caagaaataa tcaaaacaaa    60
aaatccaaaa ataaacttca atgtgaattt tgatttgggc tatatatttc aaatttcagt   120
ctaaaattta ttggcaacaa tattattaaa aaaaaaaacc tacattgtta ttacaatggg   180
gaaacttatt tattaagcgg tataaaaggt tttatacata agtaacgaaa aagtagtaag   240
taaacgacca tgagttggta attaatttgc aaaaatgatg gatgatacgt aaaagtttaa   300
ttatattatg ttaaaaattt tacttacctt aaaaacaaaa gagatcagat ttaaagaaaa   360
gagaggttag attaaaggag gaagttctac aagaaggaga actatggata tgttttggtc   420
atggaagaaa tagtttgcta gatttgtaag tgctctgttt ttcttttttt caatcatatt   480
tggattagaa gttataatca tttagcaatt tgcaacgtcc tcaaagaatg tttgaagctc   540
taattcttct atgttcggtt aaatataaat atataatgac ggtttggtat agcatatagt   600
ttgaccctac tgtttatgac tcattcatga tgacttgttc gcttgaggaa acaaattttt   660
tttttagata gatgtttcat tatccttacac ggtttcttga cattttcaac acgaatagag   720
gaagtgaatg ttgatcacgt acatttgatg aagaagtcaa cttgcaatgt taaacatgtt   780
cctcttattt tctttatata acatcttcat ttatgacgcg gtcaggaagt catcattttt   840
agacttttca tcgatgcatt atgcttcggg ttctttgttc ttggatttgt ctaagtcttg   900
gtttcttcct ttgattttgg atataatatg tagtaataat aatatattga gggttccgtg   960
tacttggact caatcaaatg gatgacaaga atctccgtaa gcgaagctac cccgaaatac  1020
aagccaaaga cttctttttc catagaaaaa tagctggtca taatctaaag gtatagtagt  1080
ttttgaatgt ttggttagta gtatataagc cctagacaga taggtttgat cttataaacc  1140
ctcgccacca ttaccaaaaa ccaataagcc aagagctttt ctcattttc ttcttgaaac  1200
ccatg                                                                1205

<210> SEQ ID NO 37
<211> LENGTH: 1205
<212> TYPE: DNA
<213> ORGANISM: Arabidopsis thaliana
<220> FEATURE:
<223> OTHER INFORMATION: prAT3G22060 disease inducible promoter

<400> SEQUENCE: 37
gatcaataca aaaacattaa tttctagaat atttttgtca ataaagtacc ataaatgtaa    60
accaagctaa atgggttggt ccacttgcag ttagatgatt cttgcttatt tacataaata   120
tcgtcaaaaa atttagttgt acgcttattg tttgattatt tagatatttt gagataatgt   180
aataagggac gtatctacta tctacgcaga aaaaaacagc attgcagctg cccatatgcg   240
tgaaatgagg ctggccattg caatgcatta cttaggttga tagtaaattt agaatgagtg   300
atgaaacatt tcaacttatt acactaaaaa ctggaaaaat gccaaaagct ccatatgcgg   360
gaaatgaggc catcatcacc attggcttgt accatgactc caaaacgcga ggacttaaag   420
cttcgatatc tatctaaact atttatgaat ggttcacaga attcataacc cgcatttggt   480

```
ctggaagatt agtgattcat aatcctgatt attataaaag aaatttcaat taatatctta    540
agatagtttg atatccggcc tatatatttt tcaaaaatgt tatattattc attgaatatt    600
taagagtgga tattttattt tggggctctg gaggattcgt tccaattaac tcgaagattt    660
tagtgtctag ctagctagtt aggcctattg aaagctacgt gtatagaaaa ctcacattct    720
tagacttttc aaagcatagg tttagagaga tattcatgaa cggtgattta atgtataaca    780
ttccaaaact atgatgatat gacgcgatga ctttgtttca ttcattgact tgaatccctc    840
cattccttct ataaattagt gcaaaatgct acgattttag tatataaagt tgcaagctta    900
acattaatca tgaagatgtg taatggatcc agtttcttag cctcattacc actgttattg    960
cttcttctca gcttcatatt ggcttccttc ttcgacacgg caggttcaat cttctttaa    1020 cctattgatt ataccacatt ggtctctttc tgattcgttt tcagaatttt attcttttca    1080
ctaatgattc ttcttttgaa ttttaagttg gacaaatcgg agtgtgctac gggagaaatg    1140
gaaacaacct gcgacccgcg tccgaagtcg tggcgcttta ccaacaacgg aacatccggc    1200
ggatg                                                                1205
```

<210> SEQ ID NO 38
<211> LENGTH: 1205
<212> TYPE: DNA
<213> ORGANISM: Arabidopsis thaliana
<220> FEATURE:
<223> OTHER INFORMATION: prAT3G57240 disease inducible promoter

<400> SEQUENCE: 38

```
gatcaataca aaacattaa tttctagaat attttttgtca ataaagtacc ataaatgtaa     60
accaagctaa atgggttggt ccacttgcag ttagatgatt cttgcttatt tacataaata   120
tcgtcaaaaa atttagttgt acgcttattg tttgattatt tagatatttt gagataatgt   180
aataagggac gtatctacta tctacgcaga aaaaaacagc attgcagctg cccatatgcg   240
tgaaatgagg ctggccattg caatgcatta cttaggttga tagtaaattt agaatgagtg   300
atgaaacatt tcaacttatt acactaaaaa ctggaaaaat gccaaaagct ccatatgcgg   360
gaaatgaggc catcatcacc attggcttgt accatgactc caaaacgcga ggacttaaag   420
cttcgatatc tatctaaact atttatgaat ggttcacaga attcataacc cgcatttggt   480
ctggaagatt agtgattcat aatcctgatt attataaaag aaatttcaat taatatctta   540
agatagtttg atatccggcc tatatatttt tcaaaaatgt tatattattc attgaatatt   600
taagagtgga tattttattt tggggctctg gaggattcgt tccaattaac tcgaagattt   660
tagtgtctag ctagctagtt aggcctattg aaagctacgt gtatagaaaa ctcacattct   720
tagacttttc aaagcatagg tttagagaga tattcatgaa cggtgattta atgtataaca   780
ttccaaaact atgatgatat gacgcgatga ctttgtttca ttcattgact tgaatccctc   840
cattccttct ataaattagt gcaaaatgct acgattttag tatataaagt tgcaagctta   900
acattaatca tgaagatgtg taatggatcc agtttcttag cctcattacc actgttattg   960
cttcttctca gcttcatatt ggcttccttc ttcgacacgg caggttcaat cttctttaa   1020 cctattgatt ataccacatt ggtctctttc tgattcgttt tcagaatttt attcttttca  1080
ctaatgattc ttcttttgaa ttttaagttg gacaaatcgg agtgtgctac gggagaaatg  1140
gaaacaacct gcgacccgcg tccgaagtcg tggcgcttta ccaacaacgg aacatccggc  1200
ggatg                                                               1205
```

```
<210> SEQ ID NO 39
<211> LENGTH: 1205
<212> TYPE: DNA
<213> ORGANISM: Arabidopsis thaliana
<220> FEATURE:
<223> OTHER INFORMATION: prAT2G18660 disease inducible promoter

<400> SEQUENCE: 39 ttttttctt aacaatatac gttttgtaaa tttaaacttg gacgatgata taacaacaca      60
aatgacatat gcttaaaagt taaaatctca tttttatat tttgaatctt tgattgatga    120
attatagcga caagccgaca aaggcaactt cctcggtaag ggcaatcgtt atcttaagtt    180
taatttgatc aaatctcttt ctcagcgata gaaagtttaa ttggtatata gagatttggg    240
cctttacata aaatgatatt tgaaggccca ctaagcccaa ttattttcca gaatgttgaa    300
ttcataaacg cagatttact tgacatgata acaaagagaa atttgtcttg attcaaaaaa    360
ataaaataaa gaagagacat tgtctttct cttgtaaaag aggtcaataa agcaaatttg    420
tttttcatac ttcatcattt gactaatttt attggtgtta tgtaacaaac cgaatattgg    480
agatatctta gggagcaagt acgtgaagtc cgaagaatat tctagatttc actattacct    540
tttgttcaag ttatttttt atatgtttag aaaagttgaa gaacaatctg actcggatac    600
catgatagat ttgggctttt aatatgagat ttcaactaaa aatcaattgg taataggtgg    660 agtgaccta acactttata tactatttga taattttaa ttttaatgt gggactttct       720 tcattaacac attttgtttt agtagatggt cctaacgtta gaacctaaca ctcatcagaa    780
ggtttaaaag acggttatac ttttcccgat ggttttggat ttgggtaagg ttgagaattt    840
tctcaaggta ggattcgaag tgatgttgag ataccctcc ttagtttctt cgaaatttcc     900
ttcgcagctt tgtgaaaata atatccacaa agaaaaaaaa aatgaacttt aaatttcaaa    960
ccctcgtgga attttccttc acacatcatc atatattcat attcattcaa ttcaccaaga   1020
aaatttaggt ggagtaagga ataacaaatt gtcctgtatg aaatcaatac aataagtaat   1080
ggaagacttg acgtagacca aagacttttc cttttactta cagtctttga gtccaattat   1140
atataaatac tcgcttccct ttgcttcgtt atttcacaaa caagttaaag aaaatgataa   1200
aaatg                                                              1205

<210> SEQ ID NO 40
<211> LENGTH: 704
<212> TYPE: DNA
<213> ORGANISM: Artificial sequence
<220> FEATURE:
<223> OTHER INFORMATION: Artificial sequence
<220> FEATURE:
<223> OTHER INFORMATION: P26448 (prAT1G16420::G1795(-UTR))

<400> SEQUENCE: 40
atattgacta ttggacctta catattccga ttgtgtttgc tatttactac ggactaccgt     60 tttgttttg tctcactttg ataattggtg aattttcat ttttggatca gctaagtgcg    120
acccaaacag aaattcaaaa gtcaagagca taatttagt ttcctaaaat aggaattaat    180
ttatggatct tagattcaca accgcatgtg gaataattag taaagaaaat gccagccttt    240
ttattatttt ttctttgtca acaagctaat gccaactctt ttaaaatgaa tgaaacctac    300
tcatataatt ccttttggc cacccgtaga ctattccaga cgattaactt aatgacactc    360 atgtttttt ccttaataat agaccatagt ccattaacac tttctttta ttaagagtaa    420 catgagagtt atattaacat ttgataataa aaacgacaat ggaaatagcc gccactcaaa    480
aaagaaagac caaggaaaaa attaaaaatg agacgtaaaa ggccaataac agcaaaccac    540
```

```
acaaagtttc tcttaggaga agaggcaaaa taacagtcaa gcatgttggt ccgtcttcag      600
acctttcgtg gtagtttaaa tgctaagtct ttcgtttata aataaagtga aaaataaatg      660
caattcataa agaaaaaaca aaggtataat tcattcattc gtca                       704

<210> SEQ ID NO 41
<211> LENGTH: 1062
<212> TYPE: DNA
<213> ORGANISM: Artificial sequence
<220> FEATURE:
<223> OTHER INFORMATION: Artificial sequence
<220> FEATURE:
<223> OTHER INFORMATION: P26463 (prAT1G26380::G1795(-UTR))

<400> SEQUENCE: 41
aatctgaaat ttaaattatt atcataaagc tacttcttta ttttagttac ttgtagtctt       60
aaaatactta gggacggttt atattaagtc acataaaaat catgaatcat tctattatat      120
actaaaagta taaccagaa tttatcagta gtatcatagt tcatcaagaa tatcacattt       180
catatcaaac tttcagtata tatacgaatg tctgataaat aagttagaaa aaaaaactaa      240
aataattgtg aagcataaca attcacaaat caaaattaac ttgaaaaaca tctaattaaa      300
acaaaacaaa aaaaaagat agttacatgc gtaaataggt ttaagtctac ataaattaat       360
ataacagtag acgcagacac aatttaatgg tggtctgatt taacgatgac ggataggatc     420
gacatttcta ctataagaaa agtcaatcgc acttttaaat taaagataa gttatgtatc       480 aaaatttctc ggccatctta aaataatggg aaaataataa tatagtcatt agtattttac     540
aacaacgtag ccttataaaa tttgaattca acgaggggg acaaagaaaa caaaggattc       600
aaagagaaga gagaggaaaa ttcagtgcat tctacaaata catttggcat aaaattcaac      660
aatacttaat cgcaattatt tcaattagta gatagctagg tttggtcaaa atatgaatga      720
agtcttacct taggttttcca tttataaaat ctcgtggtca cttaaaaaat ctctgtattc     780
aactacctaa aatgatcatt tgaaataaag aagttcagtt gatgcgactc acccctgat      840 ctaaattatg aaagtcattt cccctgtact atacgtatta cgtacgttgt aatttcataa     900
ctttgttcaa aataaacagc tacttgacga aaagtcaaac caaattcaaa agtacaccga    960
tatggaaaaa atggtcaaga ttgtcaagtt gaaattattg tctccatata tattggtatt    1020
ctataaatta caaagtagag gcataatgaa ccaaacagca aa                       1062

<210> SEQ ID NO 42
<211> LENGTH: 706
<212> TYPE: DNA
<213> ORGANISM: Artificial sequence
<220> FEATURE:
<223> OTHER INFORMATION: Artificial sequence
<220> FEATURE:
<223> OTHER INFORMATION: P26462 (prAT1G26420::G1795(-UTR))

<400> SEQUENCE: 42
atattcgttt ttataagaaa tgaaatgaat acagataata tattagtagg tgctacaatc      60
tccaaagttt gcaaaaattt gagtttcttc tattcggtaa gaaactctaa tatcaaaaaa      120
tctaaatcgc tagaaggagg gatcgaacct ccgaccttgt ggttaacagc cacacgctct      180
aaccaactga gctattccag cttttgttaa tatgtgttag ttaacttta tatatcttac       240 cataacaaaa aaaaaattca acaaagatta atcgtgcacc gggggtcggg gggatatttt      300
taagataaca ttcaacaaag attaatcgta ttcaacttta ttaaattctc tatctgtatt     360 caacttttttt ccactattga aatttgcaat atatatacta gatagaaact acaataatat    420
```

```
aatcccaaaa catgcatgtc aaatagcgaa gtaattccat agtcaatccc tgatcccagt    480
catgactcat gacaacgact tctctgtaat agcgttggaa atcatttcca ctagcttgtt    540
caaaccaaac atctcatgt tgactaaaga aatttcaaaa taaacctgca aaaccaaat     600 tcaaagtaaa cctatatgac aaaacagaag tcaattatat attaatttct ctctattcta    660
taaactaaaa tcctaataga gacgtaagac aaaattaaat aaaaat                   706
```

<210> SEQ ID NO 43
<211> LENGTH: 1185
<212> TYPE: DNA
<213> ORGANISM: Artificial sequence
<220> FEATURE:
<223> OTHER INFORMATION: Artificial sequence
<220> FEATURE:
<223> OTHER INFORMATION: P26465 (prAT1G28190::G1795(-UTR))

<400> SEQUENCE: 43

```
ttcaaaacca aataaagta atgaagaagc gagtcaaagt aaggcaacat aattacgtac     60
actatttgat gagtcaaacc tacatctttc tatgaccaaa tttgagaggt ggctacttct    120
cttaggcttt gcaacttgaa aaatatgttc cgcatctaat ctaataatag gatgttgtca    180
tgttcatatg tttcgttgaa aaatattaat tctaattaaa actcgtgtta acatcaggat    240 tggatttta tgttcatagt gataattaaa tatctccaag attagtgtaa caacaacaaa    300 aaaagaata atacttatat cataatctca ggatgatcat gattgctcaa ctaagtaggg    360
attgggtcaa tcactggtta aagagaaga aaaaggtgta atgattattc tagagtttc    420 attaaagttg aaataccta aaccaagat tgaaatgtct aaaaagaaca ctcgatactt     480 cctttaatt ccaccggtct aagtcttctt tcatttata tatttgtata acctaatgcc    540
gtcacgcacg ttaaacatag tcaaattctt tattcatata ttattatttt aatcgcttct    600
taatcacagt taacatactt ggaccaaacc tagtccatat atccaacttt taaagcatgg    660
atgtccgata acatagttga acatataca tataaggtgt gcataaaaat ataaataata    720
tgtatgcatg aaaaaaaaga aaaatacaaa acattactaa acgaatggaa taaaaaaaat    780
ctgtatatta atagatgagt atacttatta gtaaaaattt atttttaaagt aaattgaaat    840 tagccaaaaa gataaagtga aaagatgta aaaaattgaa tttttcttga aagccaaaaa    900
ttatttgttt gggccccctat ttgtttacca aataaaatga atgaaggag aactcatata    960 tttgaatatg aaaattgaaa acaaacacat ttttaagggg agataaattc ttttgtatgt   1020
aaaatactct cagtgtatat atatacaaac caaaacttca tttcatttgt tcacactgaa   1080
actccaaaac tctatctctc tctctcctcc acacaccaat ttcttcatga ccttcttctt   1140
ctagcagaga agattaaaga aaccccccaaa tccagcttat actaa                 1185
```

<210> SEQ ID NO 44
<211> LENGTH: 696
<212> TYPE: DNA
<213> ORGANISM: Artificial sequence
<220> FEATURE:
<223> OTHER INFORMATION: Artificial sequence
<220> FEATURE:
<223> OTHER INFORMATION: P26468 (prAT1G56060::G1795(-UTR))

<400> SEQUENCE: 44

```
tttaattgtc agtcatgcat taggttcact tacatggtaa cggattattt gtggtgttgt     60
tgatttagta aattggaatg ttgaagaatg cagccaggtc ccttgaatag tgggagctcc    120
ttaaaaaata ttccaagtcg atagtgttta gaagatgcgt tcggtggcta tttcctaagg    180
```

```
aaacccacat tgctcattta tcacttagtt taattatctc atctataaat aaaacgtcca      240
gtttggacac caaatcacga atcacttatt aatctttggt gatcttgtgt attagtttta      300
agaggatgtc atttagagag ttaataagct gattcgtgat ttaacaccat tggcccaaat      360
acatgattga ttatgggtcg tacaaggcaa caataaggtt ggttacttat caaaacaccg      420
gtgagaacac gtccattgac tcgttatgaa gtgttttgac ctggaacctt cagagacgac      480
cagaatcaag gacgcctcct acttttattt gaaacgcgtt gtgtcgtgtt cggtctggct      540
agaaaccgga agtttctacg aacacacctc ctaacaaatt caatatctta aaccggaaga      600
taacgtcaga aaatgtataa atatacactt tgaattgaag caattcacaa aaatcattca      660
tcatctctct taactcatca ttacacagac atagca                               696
```

<210> SEQ ID NO 45
<211> LENGTH: 1194
<212> TYPE: DNA
<213> ORGANISM: Artificial sequence
<220> FEATURE:
<223> OTHER INFORMATION: Artificial sequence
<220> FEATURE:
<223> OTHER INFORMATION: P26470 (prAT1G61560::G1795(-UTR))

<400> SEQUENCE: 45

```
aagaacacat ttgaaccaat catcgaaata tatggtggaa atatatttct accaaagatt       60 tgtttttttaa ccaaataatt gaacacaacg ctaactgaat attttataaa actgatacag      120
atttattaaa aattttgcta ataaacatta taaaattgct tttaccaatt ataggatgta      180
ttgtatctct tggactttaa tatcgttgac gatcttgaca ataaaaagc tggcgtttca       240 ttaaattggt atttacaatg agaaaaatgt gtgggatcca aaactggata taggattcgc      300
tttactgtat ctggatccga aactctaaaa tatgatgttt cttatgatct ggattttttc      360
aaactataaa tgatttctga atttccgtgt atgtcaacca atatttaaaa acagattata      420
tttcttaaat attttttcaga ttttttgaaa atatattctgt aaattacaaa tgcaaataaa      480
ttatttaaga ccgttaagga tcaaatatgt ttttagttta ttcaaatctc tcgttctctc      540
atatcgctat tttgtactta gtttagataa aagtattaag tttggcttct tagaatttga      600
tgtttctttt tttcgttttt gctatcgact tttgttttt tttttttttac tattttgttg      660 ttatttatct attccttaga ttttggtttt gtttctgata cttatatttt ctgtaattta      720
tgtcgcaact tcaaaaataa tataaatact ttacattgat attaaaaaaa aaaaattgag      780
ctctaatgac ctttggagct catgctcatc tatggaaaaa aaaatccatg caggaagaac      840
caagaggaaa cggtatacaa aataatatta ataaataat tatttgtcaa taaaataaat      900
aaaaactcac caaagtacat aacagttcac acagcatgtt tttagaaaag atcatatact      960
attggtttca aagtctttga ctttgaatgt ttgaactttt caaggttcgc ctactcgccg     1020
gtcgtctcct ttaaccttcg tctctgtgtt tatataagaa catatacgta tttgatgatt     1080
acaaaaagac aattctttat ccttctttag atttctgtgg aaagttcact atttattagg     1140
agagacaatt tcaaaaagga aagctttttg cttggaactg ttctgtgagt tcta           1194
```

<210> SEQ ID NO 46
<211> LENGTH: 1166
<212> TYPE: DNA
<213> ORGANISM: Artificial sequence
<220> FEATURE:
<223> OTHER INFORMATION: Artificial sequence
<220> FEATURE:
<223> OTHER INFORMATION: P26479 (prAT2G32210::G1795(-UTR))

```
<400> SEQUENCE: 46
aggacaattt gttattgtgg ctcaacgtaa ccgggaccgc acgtttgata agttattgtt      60 ttttttttg ttaaatgcag tcttgcgacc atgttggcct gttgcgtcct cgacgcatgc     120
attttctgag ttcggaggaa gcagtcgatt gtttattaaa tttgacactt catgcaaata    180 ttttcattg tattttgcaa gtagtttttg ggattcgatt agcttataac atttggacct    240
cctatttgtt gatttaatta tttattacta ctttttttat tttattacaa cttagtttgt     300
aatagtaaaa tttattctac tttgtgccca aaactgtcaa ttgttgttca tttaaatttc     360
tggaattaga tttagatacg ctaaattaaa tcacattttg cgtttatatt cccacctaat     420
ttgaaaccag caattattct tcttcataag aaaactttca tgtgctctct cgaaaataaa     480
gttttactct aataacaaca cgcactttgg acgagataaa gcgattcaag taaaattatt     540
atggttcaaa ctattatcta agatccgttt gtgtaaaaca taacttctaa taacatatat     600
attctgatct acttttgtta gttttattta gttaatataa gcgttaatta ttgttctctc     660
ttttgcttaa catgtaaata ttcccatgga gaaagaagta cacttttgc tttgagaaag     720 aataaaaaaa ctcttttatta ttactaaatc aagaaaaata taaaaccatg ctgcattat    780 catcatttta catattctat atataaggtt ctctaattcg tatacttttg taaatagaga    840
acaacgaatt aaaagaccaa atcgatagca tcttacctt ttgttgatat ttattaagag    900 aaaaatcaa cacattgtta ttcttcaaga gaataaattt ctggagactt agcagttaat    960
gcaatctgac ctcacgcgtt ttttttttt gacctcacgc ggttttacta aaccgacctt   1020
cgtttacttc ccttacctct ctatatatat atctctatct tcatttgcat atttcaattc   1080
atttcataat catacacctc tctacatttg ttactacttt cttctaactt gttttcaaag   1140
agaaatcaca atctatctgt tccaag                                          1166

<210> SEQ ID NO 47
<211> LENGTH: 1165
<212> TYPE: DNA
<213> ORGANISM: Artificial sequence
<220> FEATURE:
<223> OTHER INFORMATION: Artificial sequence
<220> FEATURE:
<223> OTHER INFORMATION: P26480 (prAT2G35930::G1795(-UTR))

<400> SEQUENCE: 47
tggcaaaatt gtatattgtg atattcatga agaccataaa caaaattatc ctcgaacgag      60
atgccatatc atcaaagtcg agaaacgatg ggttagagat ttgtagtttt gttgatcgtg     120
tgatgttgcc aaactacggg ttcgaaagtc ttaaagacct ttataaagga aatgcgtcga     180
gtattttgct cgagagcctc ggttgggtca gtgtcaacat gttgagtgat aagctcgagg     240
acattagtat ctatgaaagt ggaaatggtt atgaagtaca tgtatgaggg tattggttac     300
agggatatga aagacccatg tgcgttatat ggttatagta ttcatatatc aatagtaaag     360
cgacatcacg tgatattttt tcttaatgta tcaaaattcc accaatttct atttcatttt     420
ttgattaata aatacatttc actttgatag tatttagtaa atattgatga ataatcaaca     480
gaaacaaggc cgtacgagaa aagttgtata ctctcactat tatatttat tttacgacac     540 aacaaaatgg aaaatcttaa gtcaaaacgg gtggcaaaaa tgtgtaaaaa gagaggaaga     600
atcaatcaat taaagacac aaagcagaca gtagacactc ttgtcttcac caccgccacg     660
atcgcgacca aatggctctc tttatatttt atcacaattt tcttatccgt tgttacaat     720 ctctctttga aaagtcaaac cttttcatac gtctcacgtg ttcttttttc ttcacccaac     780
```

```
tcatcagcga aaataaaagg tcaaatctat gttcctcgtt cgttccttct atgagtaaat      840
aatactaata aactttatta aatagggggca gatttttttct ttttttagca tatagttata     900
gggacagctt tacaaagagt gtgtaataac taataatatt tgtatttttcc gtgttttgac     960 tttttttaata attgtgaatt tttgacatct cctttatatt taaacccaac ctcctttctc   1020
tcttcctcct aacttattca aaccaattca catcttccca aacccaacta ctacaacttg    1080
tattaagaaa aagatatatt cccttagctt ctttgatcaa tatattcgtc agggttctcg   1140
tcaaagtcct cagcatcttc atcat                                          1165
```

<210> SEQ ID NO 48
<211> LENGTH: 1195
<212> TYPE: DNA
<213> ORGANISM: Artificial sequence
<220> FEATURE:
<223> OTHER INFORMATION: Artificial sequence
<220> FEATURE:
<223> OTHER INFORMATION: P26481 (prAT2G35980::G1795(-UTR))

<400> SEQUENCE: 48

```
agcagaatag tggggttttc acgttgacta tatgcgttga tggacgcgtg aggtggaagg      60
tcgggactct tactataggg aattatcatc tccatgttcg ttgtcaggcg ttcataaacc    120
aggctgataa agcagccgga gttcatgtcg gcgaaaacac cgttaagtac acgttgatca    180
ataagtgcag tgtcaatttt taggaggtaa aaggacacaa ctttgacgcc gtcaatgttt    240
gcttttactc tttcttcttc ttttcatttt tcttctactc ggataatgtt tttgcttcta    300
tatcgtttaa ttttctacct ttttctgctg atcatataac atacataaaa tcaaaaaatt    360
taatatgata aattcatgtt aaaagaactt gccaaataaa aaccgataca gaattttctt    420
gtaaaacatt cttcaatctt tttatttat tttttttaact ttaaatttcc acttaaatta     480
aaataaagag gattacaagg ttaaaaaccc caacatggcc gcaggcctaa aaagaaaga    540 taaattcttc aaatttatat ttacgtaaac cttcaaattt aataaatttt aaaaaaccag    600
acataattat gttgagagca tcagcaacgg taatttctca acttccgttt ctcaatatat    660
gtgtaaacat aaataaaagt gtgaacacaa atattattaa tatttaattg aaaagtattt    720
taattaaacc aatgattgaa tgacaactgt gagaaacgtt gtcgataagt ttctcttggt    780
ttctctaaag agaaactttc ccttacctct ctcctccttt ggacatttct tttcttattt    840
tattggtgag agatttttatg agaaactccc gttggagttg gtctgacaca ggcggcccta    900
ggttctagaa cggtataacg agaaaccaac gtacgacgag agaccaaaaa gtaatattaa    960
catatacgat cttacaaaaa gtactcatta ttggaagttt ggggcaacat cacaagccta   1020
caattgcata atattctttg gtcaattatt caatcaaatc accgcgtaac gtgaccttac   1080
cttaatctaa taagttgacc aacgcataaa tgaaagtgta tataaagatg acttacataa    1140
acctcttagc catatatcca ttcattccaa tataattctc cacaaaatta ctatc         1195
```

<210> SEQ ID NO 49
<211> LENGTH: 1174
<212> TYPE: DNA
<213> ORGANISM: Artificial sequence
<220> FEATURE:
<223> OTHER INFORMATION: Artificial sequence
<220> FEATURE:
<223> OTHER INFORMATION: P26445 (prAT3G18250::G1795(-UTR))

<400> SEQUENCE: 49

```
atctgaaaca tactataccc aaaaatcgat gctcacacct agctagttca aactgcgtac      60
```

```
gtcaaaatat gtggtatgga cgtaaagtat tttataagtt ttgttagaaa gttagatact     120
tataaaataa aaaaattgat atttttttgg taaaaaatgg aagtttggta ttttttggca     180
gttgtataca taaataaaaa tatatattac ggagttatat attcttgttt ggtcaaatgt     240
ttcggaagct tttagattac gaaattacat aatccatgat gaattaaatt tggttagtgg     300
tagaagaata agacgccaaa agaaaaaagg gaagaacatt gggttacgtc gaaagtcctt     360
tgataagaat ttgattttgc atagtcaaat ttggaccaac aacaaaaatg gagtccacgt     420
gaaatagaag agagagactt aatagcttct catgcataaa gttatgaaca atcaatgata     480
accaatgata aataactaaa cagtacaaaa tctctgtatt tttattggat ttaacaaagg     540
ccatgaacaa tcacttcaat atttataatt tttttaaaaa gacgaggcaa ttcaagctga     600
tttatacatt atgattaatg ataattatat tatggcattt gacttttctc acgctaatgt     660
aaatggtcaa aaatccttat cttcaactaa acttcctcga caaaaccttta actgaaacta     720 tgtatgtaat ttatcaaata ttgaacttta aatttcttta aaagcataat ataatcttga     780
cctataaaat tagcctagcc tttcgaatta caagttttat attttttaaag aaacataatc     840 ttcaactaga aattattata aaccgggtcc tatcttcatc taatatacgt gattccatca     900
aaattccgca gtcaaatgtg tttagttgag aggaggagaa tagtagacta aaatggatga     960 cttttctggta agtcttgtat tgcagtcttt tctatatttt aacaaataag tcttcttttc    1020 ttaaaagaa aaatttaatt acaaagaaat cttactactg aacgaataat ttatcaaaag    1080
tcagtggcct tacgtacgaa tttatcggct ataagtagga aagcttttca cgttaaacaa    1140
cttaatctca tccacattaa ctagagaaag agag                                1174

<210> SEQ ID NO 50
<211> LENGTH: 1199
<212> TYPE: DNA
<213> ORGANISM: Artificial sequence
<220> FEATURE:
<223> OTHER INFORMATION: Artificial sequence
<220> FEATURE:
<223> OTHER INFORMATION: P26449 (prAT3G63380::G1795(-UTR))

<400> SEQUENCE: 50
ttaatttgtt gcatgctgag agctttgtta ttactagtta ccgttatgag tgagcttaat      60
tagttgtaat cttcccttct acttattcct gaaccattgt ttagtttcat aagatgatgg     120
ttagtctatt tattctcgag caagccattg tatttgttgg ttgggatttt gttaagcttg     180
ctactgcttt tggtgcaaac actcttgttt cttcttatc cacatacagt aactcgtgat      240
ctaatgtatg tcactgagca tctctgtgta tgtatgtata tgatttgagg agtttctcga     300
cattcacttc atcgcttgta tcggaatttt atgccaaatc tggtctcacc tcacgtctag     360
ttttagtgga ggtcaactta tttttgtttgt ttataaaaat aaagtcaact gcttttatgt     420
cttgctgtcg tcacatgaac aaagaaagag atgacagcga aaatggaaag tgctatgaag     480
tttcggtgat caaactcata atgccttcgt cgtacgcgct gctccatttt attatttcta     540
aacatagatt tgtggaaaag tagacggatt ttgagtttga gtagtataaa tttcacttga     600
tagatattat accaaaccaa gttggtgtgg aagattcaat ctaaatcctt ttttctttct     660
ttcgctttac tatattcgcc attcttttc atttgtccgt gcggactaag caagttggta      720
cacgcacgct attcctcctc attctacaat gacggcttgt ccacaccatt acatcatacg     780
gctgctttag aaattactac caaatctca gattaactct ctcttttagg gcacagtggt      840
tccaaaccga aacacgagac aacagataag tcaaaacaca agtacaaaag gatgtgcggc     900
```

```
ccatgtcctt tgatcgacat gacttcgtgt ttacaacgtt tctgagtggt tccaccgcct      960
gaaaatatta aactaggaca agttacttta cacgagatat ttaatatttt aaagcagata     1020
aatagcaatc aaaaggcggc caatacggat ttaaatagta ccacgaagct tagggtatta     1080
gagagagaga aatcattctt tgcgagtctt aagtgtctta caagtaacac cacatttagt     1140
tgagagagag cgagactctt ttccttctaa aaactctctt tctttcacac aaataaagc      1199

<210> SEQ ID NO 51
<211> LENGTH: 874
<212> TYPE: DNA
<213> ORGANISM: Artificial sequence
<220> FEATURE:
<223> OTHER INFORMATION: Artificial sequence
<220> FEATURE:
<223> OTHER INFORMATION: P26450 (prAT4G01010::G1795(-UTR))

<400> SEQUENCE: 51
aaacaagatt tcatgagtca gacaagacaa agccataaa caacacaaaa gtcctgcaag       60
attgctcact tgggcggttg ggcctatatg aaaatttact atctcaaaat ttaactaaga     120
gcccataaaa actgtaagat ctttgcttta aatcacattg tcttcataga ctttgtgatt     180
catggtagat ttgtgaagat ctttggtcat ctttttgttt acatttggct tattgagtgt     240
agagtgtgaa caatctgcta tgaagttggt aaaattcttt ggatccaaac ctttaaatcg     300
tagcatattt actatttcac actgctagga tctgtttata gctgatgcat tactggaatc     360
tatgatgttt actgtgttgg tctgatatat aacaagttct gaattttaaa atcaaattca     420
atatcgaatt gggcttttaa ttaaggttag gcccatcaaa tgttttgac tctttaataa     480 ttccctctct tttgtctttt attgtaaaat gcacacaatt tcgaagaaac tgccaatgga     540
gtctccattt tccagcgcca tgccaagctt gactctacga tgatagctta tttgactgct     600
tcaaaaaaaa acttcagaga attaatttcg agaattttcc caatttcaga tcatcggaaa     660
attcttacta taatctttct tatatcgctt ctctcagtta cttcaacgtt ctggtcagtt     720
tcggatataa atgttttaat ttcttagttt ccgtttcttc ttcttcttct tttttttttt     780
tttctgttac tgtaaacttg gggataacga attaaagcga tcaaatcgat gttcttatga     840
ttcaggatcc gttatagcaa aaaaagcttg actc                                874

<210> SEQ ID NO 52
<211> LENGTH: 1194
<212> TYPE: DNA
<213> ORGANISM: Artificial sequence
<220> FEATURE:
<223> OTHER INFORMATION: Artificial sequence
<220> FEATURE:
<223> OTHER INFORMATION: P26453 (prAT4G21390::G1795(-UTR))

<400> SEQUENCE: 52
tgagtatcaa tatatgcttt agtgccactt gctagtgcaa tccacttgag gtttggctgc       60
atcgatatta gatataaata cttaagcgtc atgcaaaaaa aagattacta ataattgta      120 gggttattat gggattttag gcgagcaaac aacatttaaa ctttgaagga atacaatttg     180
aaatatcaag atacgtaaaa tatgtcacgt gcaataaaat aaagagaaga cccatccaaa     240
tcaagtgtgc gatactttga ccatatgagt caatgtggcg gccaaaggca acaagcatat     300
ctaatctaag tattatataa ctaagcaaat attccactaa actagtatac aaagccaact     360
gctccactaa ttgcctgaca tacttattta ttttcaaatt tggtaaccac acctatagct     420
tatacatttt cttcgatggc cttatacaat aggaatatac tattaccttc tcattgttct     480
```

```
tattatcatc aaccatttga taaatcctca tcactcttaa acattgacta tgaactaagg      540
acgtcagaag tagtccatac aagatatgaa tggttggatc gtcctaagtc attgtattaa      600
tatacgtttc taatcaatgg aaactatata attgtaatat aatttttact aaatcatgta      660
acttgaaaac ctaactttct ttcttaataa aaattgaacc gctaaagtat ctaatccatc      720
atgtgtcaac tgacaccgtc caaaatcctc ttagagatgt aagaaaaagt ttcaaaacaa      780
ttaggtcagc caccaatcac atatttctat gcaggttgta taatcttgaa aaagaacaaa      840
aaaagtagat gacaaaaaag aattaaaaga caataataat aataccttat aaagatgata      900
ataattcaaa cagtttgacc tttttatttc aattctctgg tccaactttc caacctgacg      960
agacaaaaat atagaaactt ctcaacagca ataaaacagc aacctttcct ttttgtatcc     1020
cttctccttt gtcacctctc ctcttacttt tttatcaata ggaagtttcc gccattgtga     1080
cagacacagt tcctctgttt ctcttctttc atctttaagc aaacctcaaa aaccaatcct     1140
ttattacgaa gatcctcact tgtgtcttct tctccaacac taaaccccaa gaaa          1194
```

<210> SEQ ID NO 53
<211> LENGTH: 1193
<212> TYPE: DNA
<213> ORGANISM: Artificial sequence
<220> FEATURE:
<223> OTHER INFORMATION: Artificial sequence
<220> FEATURE:
<223> OTHER INFORMATION: P26454 (prAT4G35110::G1795(-UTR))

<400> SEQUENCE: 53

```
tctcactcgt atttgtataa ccgtcccacg ttgttgtcca cttctggaag ataagtgagg       60
tgtgtgattg attgccgttt ccaacctctt ttcaattaaa tgcttctctc tatcttcaat      120
tggtaatatt ggctttggtc aattcatcat catcatcata ttattattat accaaagaca      180
atgtcacatg aaccttataa tatacacaac tgttatacct tataaacaaa aataaaaatc      240
aacattttat tcatttttct ccgctcatca catttctctc cctcttccga ttctcctggt      300
atatctctct ctctcttttct ctttatttct ctgtttgttg attgattgca ttttgtgtg     360 aattaaaagt ttggttcttt gatccacaaa tagattcttg atctcgatca gaatcgtggg      420
tttgcttttg ttttaagaat taattcaatg atcgatgatg aaactgattg atactgtttt      480
attgtcatat gctctgtttc tttgctctgt tctaaggaaa ttttgtgaca aacgacaatc      540
atggaaaacg aaatttcaac ctattaaaaa aatattatcc acaagggtgg gccttggaag      600
tttttgtctg ttcaagaaaa caagccggtc aaaataatct accttttaac tctggtctaa      660
gtcaataact gagtgcttcc accgttgaaa tttagtatct cactggaaaa ttgtacttgg      720
aaattgcatg gtcggtccat gaaagtatta aggagaagaa acaaaccaaa agtcgtcttt      780
ttgtatctct ctatacctat acattttatg atttgattgg ttttgtgggg atcaatttca      840
ctattactcg taagaaattt ctttatggat atgttttggt gaatctctct ctgcttctca      900
caatctccct ctttactttt tttctttcat catataaagg gttggtgaaa tatgaatgga      960
atccaatttc gttgggaggt tgatgtatat tataagtttt tagtgtctaa tctttttgaa     1020
ctatttgttg aaattaaggt gtaaaggttt gaccacttac ttacccttaa tgtgatatgt     1080
tcagtccttt gacaccacaa atttgaagtt cttgtgttgt tctttgagtt tgtcttcttt     1140
gagctgatta gttatcttga ttttgttgca gttgttccat tcatcaaaaa gct           1193
```

<210> SEQ ID NO 54
<211> LENGTH: 998

```
<212> TYPE: DNA
<213> ORGANISM: Artificial sequence
<220> FEATURE:
<223> OTHER INFORMATION: Artificial sequence
<220> FEATURE:
<223> OTHER INFORMATION: P26458 (prAT5G22530::G1795(-UTR))

<400> SEQUENCE: 54
atttcttaca aacctctaaa cctttatgat gtttctagag gaccgggaaa tatattgcat     60
gcacccgtaa actacctttc aattttctac ataagtcact tcaacacaac atttgatggc    120
caaaatgtaa actgtgatta gcttactcct taaagagtga acaaaagttg cagaagtgac    180
tctatttgaa ccttactctt tatctgataa tagagagaca ttaccaaagt ataaaagagt    240
ttagtaatcc taacgtgtct ttgctaggag ttacaaaaaa aggagtcacc tttgatggct    300
tggataatta aagacttta gtagtccttt ttggactaat gaaagactaa agaaacgact    360
tttgacccaa aaaaaaaaaa aaaaaagac ttaagaaacg actcttggac tacggcctaa    420
aaatttagta ctttagtct ccaccaactc tttcttatta tataataat tttgcctaca    480 caattttaga caaaacttcc taaggtata acataattgc ctagaagatg acataatttt    540 tacacattt ttgttgaatc tgcataatgc gacacagttt aagaagaccg ttaagataa    600 cataacttcc taaacttatg cagtctacaa gatgacataa tttgcacatt ttgaaagcaa    660
aaattggatt tatggcattt tagacaaaac ttcctaaagg taaagttt acaaagtgag    720 ttgcgtggac ttagtatact tttttagttt ttttttttgc cctctctttt tggtaatttc    780
ctgcaagtga gtggtggaag aaaggaagct gcgtggagtc ccaaaaatta aaattgcaga    840
aaaacaggtc ttataataat cagcttaata gctcaggtct ctttttctca ttctgaagat    900
taaacatctt caaggaacct aatctttgtc tctggtttta ccttcgacaa acaagcacac    960
atattgtttg ttaaaaaatc atctatcccc caagaaaa                            998

<210> SEQ ID NO 55
<211> LENGTH: 1171
<212> TYPE: DNA
<213> ORGANISM: Artificial sequence
<220> FEATURE:
<223> OTHER INFORMATION: Artificial sequence
<220> FEATURE:
<223> OTHER INFORMATION: P26476 (prAT5G64905::G1795(-UTR))

<400> SEQUENCE: 55
caaaaacctt aaacgcagtg ataatcatcc tatcacaatt cacaacgtgc attatgaatg     60
gtaatattat atacaaagtt gacgagtgct ctctatgagt aacgcatgat cgctctatga    120
tttaataaaa tatactccac gaggagcaga agcaacacca acttcgaata taaaacacat    180
ttaacaatct tcactgtgac tttagacatc atgatttttt tggtgttctt ttttaaaaa    240 actcataatc tggtgataag tctcgtagtt acctcatcgt agaaccacaa tttagtattt    300
acacaagaag gtatggtctg attaaagttt gggggtcttt gtaattaggc ctacaataat    360
cattcacaaa tttgaaatat tacaatttat gagggaccac aacacctaaa aaggcataaa    420
tgcattatgc ccagtggcga cgaaaaaagt gcattaaacc aaaggaatat atgtttgatt    480 tttatttaa tgtgggaatg ggatatgcaa tattacaatt atgatattat ctgaaatttt    540
atatctttac aaaatttgat tttcaaactt aaattctata gtatgatcta catgaacact    600
ttatattctt atgcaagaaa aacaagtcct ttgtccaatc attgacctct taattgaatt    660
tgaaatattt aacaaagtac ccaatagata attcttttgt tcttgttaaa ttagatttc    720 aaaatactaa gctttagcat taatttgaat aatcaaagat cttcctttga attacctatt    780
```

```
caacatttgt ttaataactt aattcaaaca aaaaccaaag aagagcgtga attgactttg      840
accaaaacca aattctctca agagttgctg ccatattttg accgcgcgcc acgtagatta      900
gagtcaaaat tgttatttta ttcacttcaa cataaaacca aataagcatt atcggttttc      960
aacataccgg caccaacttt tccaaagtct gtatgtacct aacaaaaccg gtttatcata     1020
gaaacggtca acacaccaaa aatagttgac caacaactac ccaagtgata tcccttt aaa    1080 aggagtcgca tatgtgttac caagttccat catcaaccta ataacacaca acactaaatc    1140
tctttaccaa aaaagatta agaagtcaac g                                    1171
```

<210> SEQ ID NO 56
<211> LENGTH: 665
<212> TYPE: DNA
<213> ORGANISM: Artificial sequence
<220> FEATURE:
<223> OTHER INFORMATION: Artificial sequence
<220> FEATURE:
<223> OTHER INFORMATION: P26447 (prAT1G02360::G1795(-UTR))

<400> SEQUENCE: 56

```
taccaattag ttagccgccg aacgagaatt ttttgtgtag attccaccac attaataaaa       60
aatacgaatg agtcttccat caagataaaa taatgagatt ttccatagca agaatgagtc      120
ttcaagcatt aaaaattgaa atcagtcttt ttcggtaata ctgctacgtc gaccgaataa      180
gaatatcgtc atccactatc attttaatcg taatacacac tatctatatc attcaatgat      240
tatattgata agttgttttt attttgtatg atctcggttt catattaagt aatgtcagct      300
aaaaaaaatg tcatttttagt gaaaagccgt tatttgtttt tttctctaca ataaaaaata      360
attgcttttg ttgttttttt ccccttcacg tattcgcttt tgttgttgt cttgatatct      420 aatctaatta aggtgtaaac tatatgaaaa attataccaa aaactataga aaaagtttca      480
cttaacgtga agaagcatc gtttgatgaa tgaaaacaca tgagagcatg tataaacgaa      540
ccttcagacc aatgaaaaaa aagtccaccg ttaaagtcaa aagtcaacgc gttgatcatt      600
tacacatcta taacaaac tcatcttctt acaccaaaac catcaagatc gatccctctc      660
taaaa                                                                 665
```

<210> SEQ ID NO 57
<211> LENGTH: 939
<212> TYPE: DNA
<213> ORGANISM: Artificial sequence
<220> FEATURE:
<223> OTHER INFORMATION: Artificial sequence
<220> FEATURE:
<223> OTHER INFORMATION: P26460 (prAT1G24140::G1795(-UTR))

<400> SEQUENCE: 57

```
tgtaattaaa atctgtaact aaaatgaatt agtcagtcaa aaatatcata actacgaaat       60
aaatgtacac taaacactat caaacgtccc ttagtttaga ttttggttaa taaagctatg      120
cgtttacagg cttctaagtt ttaataatgt tggtgcaaac gtggttgaac taattctgaa      180
aacaattttt agcctaaatg gatctaacat gaaaatctac attttt ctgt ttatatgtat      240 cctaattctg tttagaaagg gctttcaaact tttggcccaa aactttatat gcatgtatga      300
tatatcaatt aattttaccg atggagactt gcatgttata cccattacag gaaaaaatta      360
gatagcctaa caaacaagtc atggcgttac tcgtgtaagg tggagatttt acgttgattt      420
tttcaaccaa taacaacaac ctccggaaaa attatcacaa aaagaaaaaa gaccaattca      480
aacattcaac gacccaaaaa aaacaaaaac actttcaacc aatttagttg attctgccgc      540
```

```
cttcaaccat ttttgttgca tggttctttt tccaactttg catttaaccg gtcctttacc    600
accggtcaat cacaatttct agtcatccaa gactaaatcg ggcctaatct attgcaccaa    660
gccaccaatc aactttaatt atccataaaa cgacactatc tattggcaga agcttcatta    720
gtctttttct tcgtgagacc ctttgaaacg aggacggagg aagtttcctt tgaataatgc    780
agcattttca acatagaaaa ttctccaaac gcaacgcaga aatgacctct gctttctcca    840
acgtcaaact tgtttagttt tatctatgtc atctctctaa ttctcttgta aatctcaata    900
atacctcttc acttaatctt tttaatattt ctcttttgg                          939
```

```
<210> SEQ ID NO 58
<211> LENGTH: 664
<212> TYPE: DNA
<213> ORGANISM: Artificial sequence
<220> FEATURE:
<223> OTHER INFORMATION: Artificial sequence
<220> FEATURE:
<223> OTHER INFORMATION: P26472 (prAT1G24145::G1795(-UTR))

<400> SEQUENCE: 58 ggggtactg tttgctaatt ttggaatatt tttgctaatt tcatgatttt ttttgttaat     60
tatgggactt aataataatt taaaaaaaca tagaaaacgt aaaaatttga gacccaatat    120
aaatgtttca acattatgcg taaaaggaca ggccttccta aaattagaac attttatatg    180
atatcctctt aagtcttaag tactatcgaa gccggagatt tctaagtttt actttacta    240 attaagctat tgacacttga taaatgccat atttttgcat tccctaaaac ctcaaaactc    300
tctaaacacg ttttgtgga catattaaaa tagtgtattt tgtagtctct tccaggtttc    360
ttccttcttg tcaacgtcgc acaagtccgt ttacggatat gggtgaataa ttgaatatta    420
tccatgtttc cttattagca gtcgctattg tgggtttctt tttggtagtc taatttatta    480
tttacttctt taaaatgggg aaacagatac aaagttgcat tacatatata acgcaataca    540
attagatccc atttgaccga gtaaacgcta agatccacac aaactcaatc gtcaactcct    600
ctctcttctc tattctatat agttgcgtga aatgtaatga aagtgatcat cattcacttc    660
taag                                                                664
```

```
<210> SEQ ID NO 59
<211> LENGTH: 1199
<212> TYPE: DNA
<213> ORGANISM: Artificial sequence
<220> FEATURE:
<223> OTHER INFORMATION: Artificial sequence
<220> FEATURE:
<223> OTHER INFORMATION: P26467 (prAT1G35230::G1795(-UTR))

<400> SEQUENCE: 59
cttctaagaa tagttgcaag cctttaaata ctccgacaaa tctggcatta gccgaaagat     60
attccaaact caaaatcgga tcagatagtg tggtggtcta attttacctg gatcgggaga    120
tgtccactct gtaccacctt gatgcatttt tactgatact gatcagatca accgatataa    180
tatatatata aaaaaagaaa gttcgtccaa aaggaatcat tattttctta accaatagaa    240
tataggaaat aataggataa atctatatta gtggacaggt aatagaatgc tttcattcac    300
attgaaatca tattgtaata agcacacttt tcttatcaaa aaaaaaaggc aaaaagaaat    360
ggccacgcaa taaatcatt agggtaagtt gaatttggt ccataatatt ataaattaat     420
ttaatctcga aagcttaatc ttatgatctc atgtgatctt tattgaattt acttacttcc    480
atagagtttt gtattttgtc taaggaaaga aaaaaaaagt ctgccagctt tggaacgccg    540
```

```
cccattcctc tagactttct tggaaacaac gcgttgttct tgttggggtc gacgaagact      600
cactaaatcc atccgacgac tcagatttta tcttggcttc ttttgatgtg tacacatatc      660
caccctgatt tgattcccaa agccaaaagc ctgaacaatg tagtgtagaa gaagtgacgg      720
gaaaaaacgg taatgaatcc acaatggata tttacagaaa gaaataaaat tatatagatt      780
atagagaagc aaaattatgc aaataatctt tatttaatac tattaaaaga gtagctgttg      840
gaaactataa caggtaattt aaaatatttt acaagttcaa catataataa ttttgaaatt      900
cagtccaaca taactatcag tatggaaata agccaaacaa attactcaaa ataagaaata      960
tgttttcaca ttattattta aacattttta gtcatttgtt tggcttattt ccaaaacgat     1020
atttatgttg gacttgtttt caaaagtatt atgttgaact tgtaaaaaaa atttatatag     1080
ctgttgaaat ttccaagaaa ataaggtttt acacctaaac ccttccacta tatatataaa     1140
ccccactttt gtctctatat ctttactaat ttcttaaacc ctctcaacaa tacgtaaca     1199
```

<210> SEQ ID NO 60
<211> LENGTH: 1165
<212> TYPE: DNA
<213> ORGANISM: Artificial sequence
<220> FEATURE:
<223> OTHER INFORMATION: Artificial sequence
<220> FEATURE:
<223> OTHER INFORMATION: P26469 (prAT1G57630::G1795(-UTR))

<400> SEQUENCE: 60

```
tcgagagtcg catggtacag tataatgtcg ctggggattt gcattgtggt ctctggttta       60
cagattttgt acttgaagca atactttgaa aagaagaagc ttatttagat catggatagt      120
ttcttgttga agattactag aaccaacagt ttgctctgct ttctttctct tgatcttctc      180
tttggaactg ttagtgtaaa attttgttca ctcatttaac ttgtaatttg tctcctatta      240
ttacatataa catataacta gactctaatt ataggaattg caactaaatt tctcttgata      300
aaaataataa tgaatttctt tggcatgtgt ttttttatat tatctgaact gaaccaaatt      360
gcagaattgt gacttgagaa aaacagagga ctctgttgat atgaagtctc atagtataaa      420
cagaggactc tatgtgaaac agagttacga aaaattctaa agtaatgaaa aaaacacatt      480
gtggttttat ctggattaga aaagccttca tatattttat ctgacaacat taagaagctt      540
aggagatttc ttgggatgca agcattttgt aacctgtttt ttgctacata acatgacatt      600
gtgttccagc taggtcaaaa gagtattaca gcattattca cataacacac agagcacaaa      660
gttaaatctt tgtagagttt ctataagacg acaagaacat atgtccacaa tacgaaacat      720
aggctgatgc atgtggcggg ggcaactgtg gtggagaggt tggtcataaa tttgggcgt       780 acacggaaac tcagactttt cctcaataca aaacatagtc tgatgcatta cgtcgtcggt      840
gcatgattgt caaggtagac gccgcaaata agcttctcgg aaaaactcta tacatgtgaa      900
cgtagactag tctatggaat cctttttgc tatgactaag tccaaacatt gaacttattg      960
cttggaaact gcatatattt gaatttagat tttgatggag actttcgttt tcttcgctga     1020
aattgcttgt gcgtttcatt gctatttcct tcttagaact agagaaccac aaccattttc     1080
tgagttatta cttcctacat agctctataa cctctattat tactttatta gatctctgat     1140
cttaaatcgt ctctctgtcg tagta                                          1165
```

<210> SEQ ID NO 61
<211> LENGTH: 1125
<212> TYPE: DNA
<213> ORGANISM: Artificial sequence
<220> FEATURE:
<223> OTHER INFORMATION: Artificial sequence
<220> FEATURE:
<223> OTHER INFORMATION: P26471 (prAT1G67810::G1795(-UTR))

<400> SEQUENCE: 61

| | | | | | |
|---|---|---|---|---|---|
| ttggtcagta | cactcaagtg | tagccgtaag | ctatgacgac | gaaatgaaaa | caactttaaa | 60 |
| ttatttccca | agcctctttc | cgacagtatg | gggctctaaa | agtatatcac | taattcagta | 120 |
| gtcgaatcga | atatgccttt | gttctttccc | ttttaaatcc | ataatttatt | tctaaaataa | 180 |
| taaaaaggag | attgtcactg | gagaagccgc | ctcaaatgat | gtccatatcg | catcataaca | 240 |
| tttaacgtca | cacgataaaa | caaaacattt | cgtattttgt | tttgcaatct | atttagtaat | 300 |
| tgcattatta | gtagtggcct | atctcttttg | aagttgaaag | tctctagttg | acttggtcgt | 360 |
| atttgtatca | ttgtcacata | taagtgaaaa | ttaagatgga | catttccgat | attattagct | 420 |
| aaattaaatc | attctaattt | tttttaccag | atattcaaaa | ttccaactca | tttagagttt | 480 |
| cacgttggca | tccaagtact | tggattagct | ttcgactaaa | caagaaattt | tacgttttg | 540 |
| catagattat | aaaattagtt | tgaaaatttg | gttcaaaaat | ttcctgatta | aaagaatata | 600 |
| acgaagcatt | ttataatgat | gacaatgatt | cataattttt | gtaagtgctt | cagttgctac | 660 |
| ctaactcaaa | gtcgcaactt | atattctaac | agtttcatca | ttttaatttt | ctaaaaaaaa | 720 |
| aaaaaaatca | aagaccaaaa | aattctaaat | taaacctata | atagtttcct | ttaaccaaaa | 780 |
| aaaaaaaacc | tatactagtt | tcaaggctcg | tagaggaagt | tagattactt | accatttaaa | 840 |
| aatctacaat | ttaaatatat | aatttttta | aagtatttta | taaaataaca | ttacaagata | 900 |
| gatctttttt | ttttggtaa | aaaataagat | agattatata | tagatagatc | aataaacata | 960 |
| aaaatagttt | tggcgcgtta | tagaaaggct | ctatgcatct | aatcactatc | ctctctccgt | 1020 |
| cgcgtagttc | aaggagttct | cctttgatta | tccttaaata | tctctcttct | ctcgttttct | 1080 |
| tctacctcct | cctcccattt | cttttcattg | cccttgttac | ggaac | | 1125 |

<210> SEQ ID NO 62
<211> LENGTH: 1200
<212> TYPE: DNA
<213> ORGANISM: Artificial sequence
<220> FEATURE:
<223> OTHER INFORMATION: Artificial sequence
<220> FEATURE:
<223> OTHER INFORMATION: P26452 (prAT4G18250::G1795(-UTR))

<400> SEQUENCE: 62

| | | | | | |
|---|---|---|---|---|---|
| tcaatacaaa | cacaaaggac | aatttggccg | agtggtctaa | ggcgccagat | ttaggctctg | 60 |
| gtccgaaagg | gcgtgggttc | aaatcccaca | gttgtcattt | agatttattt | tttccagact | 120 |
| ttttataaga | tttagagact | aaaaaacttt | ttaaaataag | tataacatag | attgttgcct | 180 |
| aaacgaatat | tgttacgtaa | ctgtaaggtt | taactttgat | tttggtccac | aacagaagag | 240 |
| cttaagcctt | ttacccatgt | ttgatcagtt | ttggatgcta | agatatagag | agtgtgcata | 300 |
| gtcttcactc | ttcactcttc | aaattgataa | tgttatgttt | cagtagaacg | atcaacgcaa | 360 |
| atagtgaaag | cctaatgagt | ggccaatcat | caaaattaga | gcgaataaaa | aggaacaaaa | 420 |
| aaaaagaaga | caatgagttt | aatactttt | agcctcaaca | agtttcaatc | ttatttttt | 480 |
| tgtaagtatc | tagctagttc | tataaaattt | atttaactta | gtgattagat | aaaagggaac | 540 |
| aaaaaaaaaa | atgactttgg | tgtttgctag | cctctacctc | aagtcctcaa | cccatcattt | 600 |
| tatttgtgaa | ttaggtagat | aaaaatttaa | aaacggacac | ctaaaaaatc | taaattctaa | 660 |
| atctgaaatt | ttaaactctt | ttaatttttt | tctagtaaaa | tgttacgaaa | gtaaatcgtt | 720 |

-continued

| tgtcccataa ctgttaataa atggtaaaat cattcgataa aacagtcgtt ttttttctct | 780 |
| tttttcatga aaaacttat tcccattgcc actaaatgga attatttaga aaaaaataaa | 840 |
| atacctcttc tttcttggca agttcccgga aaaaaatatg gattgggaaa aggatagtat | 900 |
| tgtagttaca tttatttcct ctatctgttt ccttccttct atttattctt gattgactct | 960 |
| catcaccaac gaatatgtac tagtaatttc tactaacaag cgaggaagaa gcaagagaaa | 1020 |
| ttataacgcg aaattcactt ctttggaacg tatattttt tttctttcag cagccaatgg | 1080 |
| cgaaaaggct gccattgatt ttcctcctta cttcacattt tttagtatcg ggtaggattt | 1140 |
| tcttttcttg attgataata acaatggttt tttgttaatt gtttcttatt tctaagctta | 1200 |

<210> SEQ ID NO 63
<211> LENGTH: 1193
<212> TYPE: DNA
<213> ORGANISM: Artificial sequence
<220> FEATURE:
<223> OTHER INFORMATION: Artificial sequence
<220> FEATURE:
<223> OTHER INFORMATION: P26474 (prAT4G35180::G1795(-UTR))

<400> SEQUENCE: 63

| atgttttagc tggtcatcat caactcgatt taagaaaact gaattcataa attttttagtt | 60 |
| gactacttga ctggtgttcg ttgactagtt cacttattta agttttttctt attaccagac | 120 |
| ctagaaagaa aaaatgaaa aaaaaatcac caaatgtcca aatgagatag caatgtagta | 180 |
| ctagttaata gattgtttct taagtcttat agatttgtat caaagggctt cttgactgat | 240 |
| acaagtttct tcctttaatt cggtttataa tagtattgat ctaaaaccaa actacaaata | 300 |
| cttacttacc actaaactta cttttcaaac tttggcttga agctaaactt gaagctaatt | 360 |
| ctcacttacc actagacttg aagctacttt tgaaactttg gtctcacata actagagttg | 420 |
| taaaattaga tgactagatg cctactctat atactttta attatttttg ctcataacaa | 480 |
| aagtcgagtc aaaaacaact cgcacgttta tcatctttaa ttaactactt gattaatact | 540 |
| tattaatcgt gtatacaaag agacgatgaa ggaagatcag ctcaaagttg acccttgcgt | 600 |
| tgaccaaaac atccgaagag caaacaaagt ccaattgaac aatgaacaca atctaacaca | 660 |
| aactagtttg gttactttt tagcctggct tgagttttaa gctaccgaac aaaattagaa | 720 |
| gacttcgatt tataccgatg ggtctcgctt tcgagagtat ttgaaagtga cataaccgat | 780 |
| tacgtcatct ttctcgtgtc attaatgctt acgtcatagc taataatttc taccgttcag | 840 |
| aatatatttt cttatatggt aattagagat atgaattgtt tagtgttaaa gtattgagat | 900 |
| tctcttgagc acttaaacag aaaaaaacaa ttccctaaga aaaataccct ccttttttt | 960 |
| gttttggaaa aagagattca aagtcaatat acacagccac cgaacaaatt actctatata | 1020 |
| aatccaatga aagcagagta acatttata tagccataca atttgtggct cgacgtaaat | 1080 |
| aacgcgattg gagtcgttag aggaaaataa agtttatttt gtatacaatg tctatagcat | 1140 |
| tgggaaactt atttgatttg gaatcacaag aaagtggtgg ttctcctttta ttt | 1193 |

<210> SEQ ID NO 64
<211> LENGTH: 694
<212> TYPE: DNA
<213> ORGANISM: Artificial sequence
<220> FEATURE:
<223> OTHER INFORMATION: Artificial sequence
<220> FEATURE:
<223> OTHER INFORMATION: P26457 (prAT5G18470::G1795(-UTR))

<400> SEQUENCE: 64

```
atcgaaattc atattactgt atttcgatta cctaaaaagt ttcgaaaaag aattaaaagt      60
ttgtgtggaa gattccaata cacgttgcta tcggaagaag acttggaaaa ttattcctca     120
agtcgttaat gcttggaatt agtgactaac aatcatcatt attccattga aagagccgcc     180
cacgacgcgt ttccattttc cacaccagtc aaagttgatg tctcaaatta gtaactgatt     240
tacaatttta aattacaaaa tacaaagccc gtacaagcta atgtaaacgg aagtaaaacc     300
aaatacatta acaacttttta gtttagctgt tcaaaggaca gagatatgac ctcaaccttta   360 acccaatctt tcgtctgtgt ttgaaacttc tgctcgtaaa gagactctag taaaacccttt   420 cggaagaaat ttttttaggta gtcgccatca tataatttaa agcttatgag acttgttatg   480
ttacaagcag agaccaaaga ctattcataa tcacttatca gagtataaaa tactcttttt    540
ttgtcaatcg agtataaaat actctgatat cacttataca aagttctacg aaactcatta    600
aagatttgag agtgtacaag ggacaaaagg tgctataaat atctcttaaa agagagctaa    660
aagttaagga aacacttaac caagcaaaca acaa                                694

<210> SEQ ID NO 65
<211> LENGTH: 1008
<212> TYPE: DNA
<213> ORGANISM: Artificial sequence
<220> FEATURE:
<223> OTHER INFORMATION: Artificial sequence
<220> FEATURE:
<223> OTHER INFORMATION: P26461 (prAT5G48540::G1795(-UTR))

<400> SEQUENCE: 65
ctctttaaat tttatttcta atggcatacc tatgtaatta cttacaaaaa ataagattat     60
atttaaaatg tacttcccaa ataatatagc aggaagtttt cattttttaat tatatatgtg   120 ccttttcatt taacaaattt tccaacatga aagaagata tgttggtaaa tggtaatcta    180
caaacccaaa taaaaaagaa tataaaaaaa attttagtta aagataaata taaattcttt   240
atcaatacta tttccatacc aacttgtaaa tcttcaaatt attttgatta gtatctatct   300
acaccaagta ccggaacaag tttttgtgca atacggaatc ttcacctcaa accaagccta   360
acataggcat tcatcaaggc tgaaattgtg cacaataaca cgtacaaaaa atcatcgtaa    420
aataaatacg aacatctctc gaaacagaga agtggtcaat ggtggttata ttttttcttt   480
ttttgtggtg gtgatattat gtaatatgat tagtcattga agacctttttg tagagagaag  540 tggtcgatgt tgcgccactt tagcgttaac gttgacgttt ggaaataaga agcaataaat   600
aaatcgacgg tcaataattc ctgctccata tatgttgacc tacacgtgat gccatttttgg  660 aatcttccaa cgaaaattat ttagttttaa ttcaattcaa tatattatcc attttgtctt   720
tctacaatac acaaatgaaa aaaacaaagt aaaattgacc aactaatatt tatttactga   780
tttgattggt cacaaactca caagattttg gccacaatat agacttctcg gtcaacaaaa   840
atttgtattt gatcataaat aaataaacaa ttatttccca cttgttgtta tgcgttttga   900
ccgacttcta aaaaaatcaa cgttctagaa tagataacgt tttggtataa aatcagtctc    960
ttcttctagt gactcaaaac aaactgtaaa gtttattaag aaataata                1008

<210> SEQ ID NO 66
<211> LENGTH: 1200
<212> TYPE: DNA
<213> ORGANISM: Artificial sequence
<220> FEATURE:
<223> OTHER INFORMATION: Artificial sequence
<220> FEATURE:
<223> OTHER INFORMATION: P26466 (prAT1G30700::G1795(-UTR))
```

<400> SEQUENCE: 66

```
caatatgaaa gtcaaaccag ccgctcaaat gtatccttca tgagttcatg ttatatttca      60
gtcaatactt ttcatattta aacacttatt ataattacgt aatatttttt tgcccaaaaa     120
aaaaaattac gtaatattca acatctctac cttgtagagt tccaaaacat tgtcacaaaa     180
tatctataaa gaatttattt taactaatta ggtcgttaat tgtccaaggg ttttcatag      240
ttgatatagt tctgttcaaa tatagccatc cttaatcgat tcatgggatc gtaaattact     300
acttcgagtg ttgtaaaaaa aaatgaaact tctacattac aaactcgaat ttaatgcatc     360
tggagtgata ctataaaagt agggatgctc tcaggtcgca tttgagagac acagaaatga     420
ttttaatgga attaatatat tttcagtttt tcacaaaaaa aaattgtgtt tataacaact     480
gcagattcaa tgctgatttt atgagtctca cctatagaat ttatatttct atattcatag     540
aggcagtata ggtgttgacc caacatcgaa agaacacttc gtaaaaaatt ctttggaaca     600
aggctgaaaa tttactccca aatttagcta tccgatgaag ataaatcatt taccgtttat     660
taaagaatta tcgagatttt agtccaaacc aaaagagatt atgagcctaa gattttgaat     720
ttgtattggt aaaagaaatt gaacgaaaat ttcagaaaaa aatattaata aattgaacga     780
tagagttcac ttactacata gtcaactagt gcctagctat aatagtttca aaagacaaaa     840
agaaacaaaa tcggttaact acttccgtga cataattctc attttgattt ttgaatccag     900
tctaatttga aaagtatatt caaaatcttt aaatccatta atgataactt ttataatacg     960
ttgacacacg caattgtata tacaatattc ttgaatttta aatgtaaatt ctagaatata    1020
ttgcgatcac cacactaatc aaaatctttg ggacaacttg aacccacatt tgacttttct    1080
tggtcaaata ttttggcatc atgcatgatc ttctctataa aaaccaaaag gcctcaacga    1140
cattcataaa ctcagtcatt atatttattt ttgttgtatt tcaacgttca atctctgaaa    1200
```

<210> SEQ ID NO 67
<211> LENGTH: 875
<212> TYPE: DNA
<213> ORGANISM: Artificial sequence
<220> FEATURE:
<223> OTHER INFORMATION: Artificial sequence
<220> FEATURE:
<223> OTHER INFORMATION: P26477 (prAT2G29460::G1795(-UTR))

<400> SEQUENCE: 67

```
tctcataaca tattttgtt ctgtaattta gatgataaat tgataaccaa tttgtattat      60
tacgaagaaa aagaaaacag tttgaactat tcattaaaaa aagttattgt ttaaaaggta     120
ttttattaga ttaaaatatt aaattaattg taattcactt ttggaccacg catttagcat     180
cacacgtata actttaacaa atcaggtaaa accaaatttc tttaattagg taagaaaaca     240
gaagactgaa agaaaaacta gtttggaaac aaaaaatggt atttgcagga attgtaagga     300
atttgggata ctagaaatgt atggatctaa gttagaaaaa atcaacaaaa atttgttgaa     360
tattattttat aaagttggta tgtttgagga aattgaaaaa gataaaatat atttgaatat    420
atggagagat gatataatgt gttcacggtt cattggatat ttagcagtga atgaatcaag     480
agaaagcaaa atagttattt tcttctttcc cgtcgtttta gtatacttt caagcacgag      540
aacggaatca caaaaactag tcaaaaaagg cgttaaatcc tatagaacaa aaacatataa     600
gctatggttt cgaacgggaa ccaaaccata atatgcgatg cacttctaat agcaatcaaa     660
aatttgttaa tatgtacata tatattttg ttttattaaa accgtatcat actttatctg      720
cagttaaaacc gcacatcttt attcggagcc tatatatcta cactgcctat atatcaaccg    780
```

```
accaaacatt cacgaaaaca aaccacataa actagtcaaa gaagaataga tgagttacat    840
tataaaaaag ttcaagtgag agaaagagag gtcca                              875
```

<210> SEQ ID NO 68
<211> LENGTH: 652
<212> TYPE: DNA
<213> ORGANISM: Artificial sequence
<220> FEATURE:
<223> OTHER INFORMATION: Artificial sequence
<220> FEATURE:
<223> OTHER INFORMATION: P26442 (prAT2G43620::G1795(-UTR))

<400> SEQUENCE: 68

```
accagggttg gtaagactaa accgcttttt attgatatgc tggtttaatt ttgacgcatg     60
actatttgga aattgcaata attgagttgg attttttctaa ttttggttga ttttgattta   120
taaatagaaa cattttggct tcactagtca tttttctcac aattccatac aattttttgtt  180 aaaaatcaaa gtaagacttt aaagaacgt tctaaatgct atattagttg accaaaaaaa    240
atgctatatt agctaacaat atcgtttgag ctaattaaca aaaacttgga actattcaat   300
agaaaaatct caaacgtttg aactaatcta aacttgatta tctcaatcaa gttttttatga  360 gaatgatttt catccaagta acttggctct ttaaaatttt gattacatat tcgttttttga 420 tctgatctat gaccgacatg gaatttctca taacgacaag agaaaaaact gtgtcattga   480
cttttgttaa gtggtacaaa gtggcattga ctttgactca gaaaaagcca atcaataatc   540
gtgaaagatg tctaacactg atcaatattt caatttgaat agaccaaatt tacactataa   600
atacatcaac acaccttctt catttcttca cacaacaccc tccatacaca aa           652
```

<210> SEQ ID NO 69
<211> LENGTH: 1200
<212> TYPE: DNA
<213> ORGANISM: Artificial sequence
<220> FEATURE:
<223> OTHER INFORMATION: Artificial sequence
<220> FEATURE:
<223> OTHER INFORMATION: P26443 (prAT3G02840::G1795(-UTR))

<400> SEQUENCE: 69

```
ctacgatgat tgaaccaact ggcttatgtt ttacctatct gcgttaaatt tcgtggtaaa     60
ctgaaccggg atgtaatgaa tccggttttg gtttgatttt ttttaaatga aaataacttt    120
ctgtggatct tttaatcgaa aataatattg aacgttacat aattgggtga aaattcgtat    180
ttatcagata tttggttttg atcgaatctt cgtgtggttt atcttagata ctcgaacttt    240
taaagcagtg tatgaatcta cgcgtaaaat atttaatgta ttgaagtaat attggaaaaa    300
caatgacgcg gggaaaagta aacaaacacg gacccgacga cggataagcg accaagcccg    360
agtcgcatcg tcttggtctt aagtctttcc ctactcgttt tatcattttc ttaaactaaa    420
aactaattta atcactctta attatttact tttttctttt aattcaacta tgactaattc    480
ttattcacag aatgagtctc acatgcctac tcgtcgtact cgactccagt ccaaatgttc    540
ccatacttgt aatctatact acatatatta tacgtcatcg tcatgtatat acaagactca   600
atatataacg tccaaattaa tcaaagattt aacatgatcg ggaaccaata tctaatcatc    660
gattagatat atttaagtct agtaactaat tagtatattt tctacaaatt gtttaattaa    720
acatatagta tacagttggt aaaggggaaa cacgcgtaat ctatatgtat atattaataa    780
tatatagttc ttggtatgat cttcttagtt attttatttac taagctttct agactttaac   840
aatatttgaa tgaaaaaaaa atttaattaa ccgtcgaaaa aaaagtcata aatctggacg    900
```

```
cagaatacta atccacagat ttcaacggtc aacattccaa ttcagttcac aaacctaaat    960
caaacgttcc atttcatacc tttttttctct ttcaagctta tacaaccttt gaccatgtct  1020
cactttatta ataagtacaa aaccaccttaa cattacatgc atatatataa ataaaacacg  1080
ttaaggaaca tatatttata caaatcccat aaacccccatt tcattcttca tcgaatagtc  1140
gaaaaatatt tgaactttct taggaaacca aaccaacaaa acaaaaagga aaacgagata  1200
```

<210> SEQ ID NO 70
<211> LENGTH: 1267
<212> TYPE: DNA
<213> ORGANISM: Artificial sequence
<220> FEATURE:
<223> OTHER INFORMATION: Artificial sequence
<220> FEATURE:
<223> OTHER INFORMATION: P26446 (prAT3G26830::G1795(-UTR))

<400> SEQUENCE: 70

```
ttatatgcaa agtacatgtc aaaacgttat cttatttaca tccatttact aatcaaatat     60 ctatttacc acaaaaggtg tgttttatac cctatcatgt tttactcttg agatatgttc    120
tttgacacca cccacaaaat atctctacga aatacgaagc cactatatgt ctctttaatt    180 tcactttta tagttttttt caccgctaaa attgttgact aaaaaatata ttgcataaaa    240
ataattgata atatatttat aagaaaaact atgataagaa aaaatataat cggttgaaat    300
gagtcatgac taacaataat taaaggttag gaaattaaaa gaaaataaat tctgaaataa    360
ctaaaaaaaa aaaatagaa gatgatgata tatggatccc tatactaata ttttggaagt    420
acattgaaaa actaactttc aaagacccaa ttaattaagc tcattaagga taaacatgtt    480
aaatactaac ttatggacat taattaaatt aaaaattata aaacgaaaat aaattgatga    540
caaaaaaaaa actatgaatt ttcttattag gatttgtaat ctactttctt gaaaaaaatt    600
gaagtttact gacggcttcc tttttttgga aactccaaaa taacaaaaca tatgaagaag    660
ttttggaata gcctttgact caacaacttt aacaatagaa agaaaacatg tttaattaat    720
gttcatgcac ttcgtctcgg ctgcccttg tggcctgtgg ggttgccggg ttggcttagc    780
ttgagacgac ccaatactga atttgttagc tcggtcagtg aagtctacat gcatgataca    840
aaaagattga ctagtgttta agttttttt tttttttttt tttttttttca taaatggtag    900 tgtctcatat tagaaatggt agtttgaaaa gtattccagtt tgtttgttca ctttggatta    960 tttgatttg gttttgttaa ttgaatcagt tttgtttgaa aagtattcac ttttgaaaag   1020
tgttcacttt aaaaagtttt gtttgaaaag tgttcacttt gaaaagtatt ctttgagaag   1080
tgctcagttt tggtttgtcc acttacgatt attattcaca agctcagcg gatagtagtg   1140 actagtgact tatgactttg aataaagaat ttccctctaa aggaatgaat acattataaa   1200
tagattatta acctaagctt gatagagaag acagaacaaa aaaaaacaca agaacagggc   1260
aaggaaa                                                          1267
```

<210> SEQ ID NO 71
<211> LENGTH: 1199
<212> TYPE: DNA
<213> ORGANISM: Artificial sequence
<220> FEATURE:
<223> OTHER INFORMATION: Artificial sequence
<220> FEATURE:
<223> OTHER INFORMATION: P26456 (prAT5G12930::G1795(-UTR))

<400> SEQUENCE: 71

```
gattattcaa aagacaactc atgtgcccgc gcatgtgctt gacgttcgtt tgccgtgtat     60
```

```
tagaacttta aaaactgatt catataaatc atcggtcgat tgaaatatat taacatggat      120
tatgatgaca acaatcatta tacaattaag ttttatgaaa tgatcatcca caaaacataa      180
cttttgtcgg ctattttttt gttgacgtga caaactaaat tagtaaactg tgttttgagt      240
gcaaaaagat gagaaatttg tgggattgat tgcatagaat aacacttaca aaaatgtagg      300
tagtatgcag gggagtcaac aacagacgac ttttcataat tcagaaaacg aagaaaaaca      360
aaaagaaagg tcgatttccc aaggactagg gcatagcacg tgtctatatc actggaggat      420
atatcactta daccgttaga cgtcacgtgt aatcgtgtat taatgcttgc aaaatgtggt      480
tcaatcaaat acccaattaa gggttatgag aactaataca aaaatgtggt tcccgtaaat      540
aatgcatgag caagcacatg actgacatga gagatagacc agcgaataaa ggttaagtat      600
tgacgcacca tgcaaagcgt aacggtgaac tggagctcta ctggctgaga taattcacaa      660
ggtgaaggtg agatatattt taggagagcc agaaaggtag aacccaagac aaataaagag      720
agagaccaag tgagttttgg actaatgttt ttcaaagaat gtgtctataa ctatttatta      780
agttccaaaa aaagacaaat aaaagtatga ttttctata taggactact cgattaatct      840
taacaaaaag acgaataagc agaaaacata tatgtttgtt ttttcaaaac aataaccttg      900
gaaatcaaaa caccagaaaa atgtggctgt gaagaaaagt acaagagaga cagtaaaaag      960
aaaatgaacc aaaaaggcaa aaaaatgaat acgtggcttc aatgtagacc cagacgatga     1020
acgtcgcatc accttcctta cggggaaat ctcacatttt gaaattacag aaaactccaa     1080
agaacccaaa attgaatatt gaatattgaa aattgaaaaa atctctcttt gaagaattga     1140
aatctctctt tgaagacgaa cgaacctcgt tgattcctcc attcctcttc ggctcgtcc     1199
```

<210> SEQ ID NO 72
<211> LENGTH: 1215
<212> TYPE: DNA
<213> ORGANISM: Artificial sequence
<220> FEATURE:
<223> OTHER INFORMATION: Artificial sequence
<220> FEATURE:
<223> OTHER INFORMATION: P26459 (prAT5G24110::G1795(-UTR))

<400> SEQUENCE: 72

```
gtcgactaac agacatcacc gaaaaagtcg ccgaaaaaat tgaccggaac cacatatgta       60
aaaatgagtt ccaacaagag gcagtacaaa agaataggca taaccgtacc gcataagtgt      120
tcaagcccaa ggcaaagcca tatctaaaaa tattttcata caaaaaggtg tatacctaaa      180
attttctttt gaagtaagaa caaaaaaaaa gttaaaattt attttcatat gttctcgaaa      240
agtatattta ttctaatatg aaatggcaaa taatttgcc ccgctggaat ttctatatag      300
tttgcgttta ttagagtttg cgtttgtatt tagcattatt attatttgca ttgtcgttag      360
cttttacatc tgcatttagt gttatgtttc tagcttttgc tttggcattt ctattttttt      420
tttgttagag tttgattttg aatctatttt aagatttata tatgacgaat ttatttatta      480
tatatattat gaaatttcat atgttatact atatttttct aatgtatatt gtttagtctc      540
ataaactttt taaacgccta gattgtctaa acgtcgatta tgggttatat attgattatt      600
gacactaggt gatcaattgt cactccttat tgtctacagt tatcttaaac acttttatag      660
aaactctaga aatgctatct tgtattgaat ttggttccat aaatggatcg ataattaaac      720
ttgatccaaa acaaaatgaa tattccaaca taatgaccat atttgtctct tggaatttct      780
aaactcaata ttgaatttt atagcaaaat taaaatttac aatagaaaat catatcctaa      840
taagaatgaa tagttattaa caaattaata ttacgaatgt aagttaaatg attgagaccc      900
```
taatattaaa acaaaaccag atcatgtaat tcaaaatcca ataaatcaaa aataaaaagg    960
atcgagaagc agagaactgg tcagcatgtt ggactttcca aattcattga ccaaagactg   1020
gtctcacttc tcacaaacca catcagcttt cttcgttctt cagtcaaaaa gtcaaactat   1080
ctctctcaca catcctcttt aaattctcct ctttctcagt ttccagaagc catgcaaaaa   1140
taaacatagt aacaatactt taaactattt acaccacttt aatcttattc tccactcttt   1200
gaacgtagcg gccgc                                                    1215

<210> SEQ ID NO 73
<211> LENGTH: 1188
<212> TYPE: DNA
<213> ORGANISM: Artificial sequence
<220> FEATURE:
<223> OTHER INFORMATION: Artificial sequence
<220> FEATURE:
<223> OTHER INFORMATION: P26579 (prAT2G18690::G1795(-UTR))

<400> SEQUENCE: 73
gtttgaaaac cggtttatgt aactatcaag aaataatcaa aacaaaaaat ccaaaaataa     60
acttcaatgt gaattttgat ttgggctata tatttcaaat ttcagtctaa aatttattgg    120
caacaatatt attaaaaaaa aaaacctaca ttgttattac aatggggaaa cttatttatt    180
aagcggtata aaaggtttta tacataagta acgaaaagt agtaagtaaa cgaccatgag    240
ttggtaatta atttgcaaaa atgatggatg atacgtaaaa gtttaattat attatgttaa    300
aaattttact taccttaaaa acaaaagaga tcagatttaa agaaaagaga ggttagatta    360
aaggaggaag ttctacaaga aggagaacta tggatatgtt ttggtcatgg aagaaatagt    420
ttgctagatt tgtaagtgct ctgttttttct tttttttcaat catatttgga ttagaagtta    480
taatcattta gcaatttgca acgtcctcaa agaatgtttg aagctctaat tcttctatgt    540
tcggttaaat ataaatatat aatgacggtt tggtatagca tatagtttga ccctactgtt    600
tatgactcat tcatgatgac ttgttcgctt gaggaaacaa atttttttt tagatagatg    660 tttcattatc ttcacacggtt tcttgacatt ttcaacacga atagaggaag tgaatgttga    720
tcacgtacat ttgatgaaga agtcaacttg caatgttaaa catgttcctc ttatttttctt    780 tatataacat cttcatttat gacgcggtca ggaagtcatc attttttagac ttttcatcga    840 tgcattatgc ttcgggttct tgttcttgg atttgtctaa gtcttggttt cttcctttga    900
ttttggatat aatatgtagt aataataata tattgagggt tccgtgtact tggactcaat    960
caaatggatg acaagaatct ccgtaagcga agctaccccg aaatacaagc caaagacttc   1020 ttttttccata gaaaaatagc tggtcataat ctaaaggtat agtagttttt gaatgtttgg   1080
ttagtagtat ataagcccta gacagatagg tttgatctta taaaccctcg ccaccattac   1140
caaaaaccaa taagccaaga gcttttctca ttttttcttct tgaaaccc                1188

<210> SEQ ID NO 74
<211> LENGTH: 689
<212> TYPE: DNA
<213> ORGANISM: Artificial sequence
<220> FEATURE:
<223> OTHER INFORMATION: Artificial sequence
<220> FEATURE:
<223> OTHER INFORMATION: P26580 (prAT3G22060::G1795(-UTR))

<400> SEQUENCE: 74
gatgtagaag acaatctctt gacaactttc ctatttgtt tggttttgtt ttcttaattt      60 tgttttatt ttggttacaa gtcaaaactt ttttggttttg aaataatata atgtataaat    120

| | |
|---|---|
| cccttttaaa ttagtgaaaa ccctcaaaca agaaaaagaa caaaaaaaaa aattgattta | 180 |
| atatatttga gcagttaaag ggagaaaatt atcatttaga taaaatacat ttaaaaaaaa | 240 |
| agaatttatg tccacaccgt acatatctta gtttcactca gtcaaccctt tgaatgttga | 300 |
| cttttttcatt caccgcaata ccaagttccc ctcaactcat ggccctctac tttacatttc | 360 |
| taatttcatc tagaagcttg aaatgaaagt tggatcaaat gggacaaaaa attgttgttt | 420 |
| tgacataatt gcttcatctt agccaatcag ctaaattgac ttctttttttg ttcaaaggaa | 480 |
| ctctcgtgat tggaaaatga ccaaatccca attgtacaaa aatgaaaact tcaacccatt | 540 |
| ctaatattta ttaaataaat aaataacttg tctcaccacc caaagaccaa aatcatctag | 600 |
| ccactctata aaacatcctt acctcaacac ttcttctatc aaaaaaaaaa aagacaccct | 660 |
| ccacaaaata tcaattttct tccaaaaca | 689 |

<210> SEQ ID NO 75
<211> LENGTH: 1186
<212> TYPE: DNA
<213> ORGANISM: Artificial sequence
<220> FEATURE:
<223> OTHER INFORMATION: Artificial sequence
<220> FEATURE:
<223> OTHER INFORMATION: P26581 (prAT3G57240::G1795(-UTR))

<400> SEQUENCE: 75

| | |
|---|---|
| ttaatttcta gaatattttt gtcaataaag taccataaat gtaaaccaag ctaaatgggt | 60 |
| tggtccactt gcagttagat gattcttgct tatttacata aatatcgtca aaaaatttag | 120 |
| ttgtacgctt attgtttgat tatttagata ttttgagata atgtaataag ggacgtatct | 180 |
| actatctacg cagaaaaaaa cagcattgca gctgcccata tgcgtgaaat gaggctggcc | 240 |
| attgcaatgc attacttagg ttgatagtaa atttagaatg agtgatgaaa catttcaact | 300 |
| tattcacacta aaaactggaa aaatgccaaa agctccatat gcgggaaatg aggccatcat | 360 |
| caccattggc ttgtaccatg actccaaaac gcgaggactt aaagcttcga tatctatcta | 420 |
| aactatttat gaatggttca cagaattcat aacccgcatt tggtctggaa gattagtgat | 480 |
| tcataatcct gattattata aaagaaattt caattaatat cttaagatag tttgatatcc | 540 |
| ggcctatata ttttttcaaaa atgttatatt attcattgaa tatttaagag tggatatttt | 600 |
| attttggggc tctggaggat tcgttccaat taactcgaag attttagtgt ctagctagct | 660 |
| agttaggcct attgaaagct acgtgtatag aaaactcaca ttcttagact tttcaaagca | 720 |
| taggtttaga gagatattca tgaacggtga tttaatgtat aacattccaa aactatgatg | 780 |
| atatgacgcg atgactttgt ttcattcatt gacttgaatc cctccattcc ttctataaat | 840 |
| tagtgcaaaa tgctacgatt ttagtatata agttgcaag cttaacatta atcatgaaga | 900 |
| tgtgtaatgg atccagtttc ttagcctcat taccactgtt attgcttctt ctcagcttca | 960 |
| tattggcttc cttcttcgac acggcaggtt caatcttctt ttaacctatt gattatacca | 1020 |
| cattggtctc tttctgattc gttttcagaa ttttattctt ttcactaatg attcttcttt | 1080 |
| tgaattttaa gttggacaaa tcggagtgtg ctacgggaga aatggaaaca acctgcgacc | 1140 |
| cgcgtccgaa gtcgtggcgc tttaccaaca acggaacatc cggcgg | 1186 |

<210> SEQ ID NO 76
<211> LENGTH: 1178
<212> TYPE: DNA
<213> ORGANISM: Artificial sequence
<220> FEATURE:
<223> OTHER INFORMATION: Artificial sequence
<220> FEATURE:
<223> OTHER INFORMATION: P26582 (prAT2G18660::G1795(-UTR))

<400> SEQUENCE: 76

| | | | | | |
|---|---|---|---|---|---|
| tgtaaattta | aacttggacg | atgatataac | aacacaaatg | acatatgctt | aaaagttaaa | 60 |
| atctcatttt | ttatattttg | aatctttgat | tgatgaatta | tagcgacaag | ccgacaaagg | 120 |
| caacttcctc | ggtaagggca | atcgttatct | taagtttaat | ttgatcaaat | ctctttctca | 180 |
| gcgatagaaa | gtttaattgg | tatatagaga | tttgggcctt | tacataaaat | gatatttgaa | 240 |
| ggcccactaa | gcccaattat | tttccagaat | gttgaattca | taaacgcaga | tttacttgac | 300 |
| atgataacaa | agagaaattt | gtcttgattc | aaaaaaataa | aataaagaag | agacatttgt | 360 |
| cttttctcttg | taaaagaggt | caataaagca | aatttgtttt | tcatacttca | tcatttgact | 420 |
| aattttattg | gtgttatgta | acaaaccgaa | tattggagat | atcttaggga | gcaagtacgt | 480 |
| gaagtccgaa | gaatattcta | gatttcacta | ttacctttg | ttcaagttat | ttttttatat | 540 |
| gtttagaaaa | gttgaagaac | aatctgactc | ggataccatg | atagatttgg | gcttttaata | 600 |
| tgagatttca | actaaaaatc | aattggtaat | aggtggagtg | accctaacac | tttatatact | 660 |
| atttgataat | tttaattttt | taatgtggga | ctttcttcat | taacacattt | tgttttagta | 720 |
| gatggtccta | acgttagaac | ctaacactca | tcagaaggtt | taaaagacgg | ttatactttt | 780 |
| cccgatggtt | ttggatttgg | gtaaggttga | gaattttctc | aaggtaggat | tcgaagtgat | 840 |
| gttgagaata | ccctccttag | tttcttcgaa | atttccttcg | cagctttgtg | aaaataatat | 900 |
| ccacaaagaa | aaaaaaaatg | aactttaaat | ttcaaaccct | cgtggaattt | tccttcacac | 960 |
| atcatcatat | attcatattc | attcaattca | ccaagaaaat | ttaggtggag | taaggaataa | 1020 |
| caaattgtcc | tgtatgaaat | caatacaata | agtaatggaa | gacttgacgt | agaccaaaga | 1080 |
| cttttccttt | tacttacagt | ctttgagtcc | aattatatat | aaatactcgc | ttcccttttgc | 1140 |
| ttcgttattt | cacaaacaag | ttaaagaaaa | tgataaaa | | | 1178 |

<210> SEQ ID NO 77
<211> LENGTH: 450
<212> TYPE: DNA
<213> ORGANISM: Arabidopsis thaliana
<220> FEATURE:
<223> OTHER INFORMATION: G1795

<400> SEQUENCE: 77

| | | | | | |
|---|---|---|---|---|---|
| acaaacacgc | aaaagtcat | taatatatgg | atcaaggagg | tcgaggtgtc | ggtgccgagc | 60 |
| atggaaagta | ccggggagtt | cggagacgac | cttggggaaa | atatgcagca | gagatacgag | 120 |
| attcgaggaa | gcacggtgaa | cgtgtgtggc | ttggaacgtt | cgatacggca | gaggaagcgg | 180 |
| ctagagccta | tgaccaagct | gcttactcca | tgagaggcca | agcagcaatc | cttaacttcc | 240 |
| ctcatgagta | taacatgggg | agtggtgtct | cttcttccac | cgccatggct | ggatcttcct | 300 |
| ccgcctccgc | ctccgcttct | tcttcttcta | ggcaagtttt | tgaatttgag | tacttggatg | 360 |
| atagtgtttt | ggaggagctc | cttgaggaag | gagagaaacc | taacaagggc | aagaagaaat | 420 |
| gagcgagata | taattcatga | ttatttctaa | | | | 450 |

<210> SEQ ID NO 78
<211> LENGTH: 131
<212> TYPE: PRT
<213> ORGANISM: Arabidopsis thaliana
<220> FEATURE:
<223> OTHER INFORMATION: G1795 polypeptide

<400> SEQUENCE: 78

Met Asp Gln Gly Gly Arg Gly Val Ala Glu His Gly Lys Tyr Arg
1               5                   10                  15

Gly Val Arg Arg Arg Pro Trp Gly Lys Tyr Ala Ala Glu Ile Arg Asp
            20                  25                  30

Ser Arg Lys His Gly Glu Arg Val Trp Leu Gly Thr Phe Asp Thr Ala
            35                  40                  45

Glu Glu Ala Ala Arg Ala Tyr Asp Gln Ala Ala Tyr Ser Met Arg Gly
50                  55                  60

Gln Ala Ala Ile Leu Asn Phe Pro His Glu Tyr Asn Met Gly Ser Gly
65                  70                  75                  80

Val Ser Ser Ser Thr Ala Met Ala Gly Ser Ser Ala Ser Ala Ser
                85                  90                  95

Ala Ser Ser Ser Arg Gln Val Phe Glu Phe Glu Tyr Leu Asp Asp
            100                 105                 110

Ser Val Leu Glu Glu Leu Leu Glu Gly Glu Lys Pro Asn Lys Gly
            115                 120                 125

Lys Lys Lys
        130

<210> SEQ ID NO 79
<211> LENGTH: 696
<212> TYPE: DNA
<213> ORGANISM: Arabidopsis thaliana
<220> FEATURE:
<223> OTHER INFORMATION: G1792

<400> SEQUENCE: 79
aatccataga tctcttatta ataacagtg ctgaccaagc tcttacaaag caaaccaatc      60
tagaacacca aagttaatgg agagctcaaa caggagcagc aacaaccaat cacaagatga     120
caagcaagct cgtttccggg gagttcgaag aaggccttgg ggaaagtttg cagcagagat     180
tcgagacccg tcgagaaacg gtgcccgtct ttggctcggg acatttgaga ccgctgagga     240
ggcagcaagg gcttatgacc gagcagcctt taaccttagg ggtcatctcg ctatactcaa     300
cttccctaat gagtattatc cacgtatgga cgactactcg cttcgccctc cttatgcttc     360
ttcttcttcg tcgtcgtcat cgggttcaac ttctactaat gtgagtcgac aaaaccaaag     420
agaagttttc gagtttgagt atttggacga taaggttctt gaagaacttc ttgattcaga     480
agaaaggaag agataatcac gattagtttt gttttgatat tttatgtggc actgttgtgg     540
ctacctacgt gcattatgtg catgtatagg tcgcttgatt agtactttat aacatgcatg     600
ccacgaccat aaattgtaag agaagacgta ctttgcgttt tcatgaaata tgaatgttag     660
atggtttgag tacaaaaaaa aaaaaaaaa aaaaaa                                696

<210> SEQ ID NO 80
<211> LENGTH: 139
<212> TYPE: PRT
<213> ORGANISM: Arabidopsis thaliana
<220> FEATURE:
<223> OTHER INFORMATION: G1792 polypeptide

<400> SEQUENCE: 80

Met Glu Ser Ser Asn Arg Ser Ser Asn Asn Gln Ser Gln Asp Asp Lys
1               5                   10                  15

Gln Ala Arg Phe Arg Gly Val Arg Arg Pro Trp Gly Lys Phe Ala
            20                  25                  30

Ala Glu Ile Arg Asp Pro Ser Arg Asn Gly Ala Arg Leu Trp Leu Gly
            35                  40                  45

Thr Phe Glu Thr Ala Glu Glu Ala Ala Arg Ala Tyr Asp Arg Ala Ala
        50                  55                  60

Phe Asn Leu Arg Gly His Leu Ala Ile Leu Asn Phe Pro Asn Glu Tyr
 65                  70                  75                  80

Tyr Pro Arg Met Asp Asp Tyr Ser Leu Arg Pro Pro Tyr Ala Ser Ser
                85                  90                  95

Ser Ser Ser Ser Ser Ser Gly Ser Thr Ser Thr Asn Val Ser Arg Gln
            100                 105                 110

Asn Gln Arg Glu Val Phe Glu Phe Gly Tyr Leu Asp Asp Lys Val Leu
        115                 120                 125

Glu Glu Leu Leu Asp Ser Glu Glu Arg Lys Arg
        130                 135

<210> SEQ ID NO 81
<211> LENGTH: 549
<212> TYPE: DNA
<213> ORGANISM: Arabidopsis thaliana
<220> FEATURE:
<223> OTHER INFORMATION: G1791

<400> SEQUENCE: 81
atgtacatgc aaaacaaaa accttaaaag ctttcatgga acgtatagag tcttataaca      60
cgaatgagat gaaatacaga ggcgtacgaa agcgtccatg gggaaaatat gcggcggaga     120
ttcgcgactc agctagacac ggtgctcgtg tttggcttgg acgtttaac acagcggaag      180
acgcggctcg ggcttatgat agagcagctt tcggcatgag aggccaaagg gccattctca    240
attttcctca cgagtatcaa atgatgaagg acggtccaaa tggcagccac gagaatgcag    300
tggcttcctc gtcgtcggga tatagaggag gaggtggtgg tgatgatggg agggaagtta   360
ttgagttcga gtatttggat gatagtttat tggaggagct tttagattat ggtgagagat    420
ctaaccaaga caattgtaac gacgcaaacc gctagatcat cactacttac ttacagtgta    480
atgtttttgg agtaaagagt aataatcaat ataatatact ttagtttagg aaaaaaaaa     540
aaaaaaaaa                                                             549

<210> SEQ ID NO 82
<211> LENGTH: 139
<212> TYPE: PRT
<213> ORGANISM: Arabidopsis thaliana
<220> FEATURE:
<223> OTHER INFORMATION: G1791 polypeptide

<400> SEQUENCE: 82

Met Glu Arg Ile Glu Ser Tyr Asn Thr Asn Glu Met Lys Tyr Arg Gly
 1               5                  10                  15

Val Arg Lys Arg Pro Trp Gly Lys Tyr Ala Ala Glu Ile Arg Asp Ser
            20                  25                  30

Ala Arg His Gly Ala Arg Val Trp Leu Gly Thr Phe Asn Thr Ala Glu
        35                  40                  45

Asp Ala Ala Arg Ala Tyr Asp Arg Ala Ala Phe Gly Met Arg Gly Gln
    50                  55                  60

Arg Ala Ile Leu Asn Phe Pro His Glu Tyr Gln Met Met Lys Asp Gly
 65                  70                  75                  80

Pro Asn Gly Ser His Glu Asn Ala Val Ala Ser Ser Ser Gly Tyr
                85                  90                  95

Arg Gly Gly Gly Gly Asp Asp Gly Arg Glu Val Ile Glu Phe Glu
            100                 105                 110

```
Tyr Leu Asp Asp Ser Leu Leu Glu Glu Leu Leu Asp Tyr Gly Glu Arg
        115                 120                 125

Ser Asn Gln Asp Asn Cys Asn Asp Ala Asn Arg
    130                 135

<210> SEQ ID NO 83
<211> LENGTH: 553
<212> TYPE: DNA
<213> ORGANISM: Arabidopsis thaliana
<220> FEATURE:
<223> OTHER INFORMATION: G30

<400> SEQUENCE: 83
ctcttctgac gcacaacagt atatacacat acacagatat atggatcaag gaggtcgtag      60
cagtggtagt ggaggaggag gagccgagca agggaagtac cgtggagtaa ggagacgacc    120
ttggggtaaa tacgccgcgg aaataagaga ttcgaggaag cacggagagc gtgtgtggct    180
agggacattc gacactgcgg aagacgcggc tcgagcctat gaccgagccg cctattcaat    240
gagaggcaaa gctgccattc tcaacttccc tcacgagtat aacatgggaa ccggatcctc    300
atccactgcg gctaattctt cttcctcgtc gcagcaagtt tttgagtttg agtacttgga    360
cgatagcgtt ttggatgaac ttcttgaata tggagagaac tataacaaga ctcataatat    420
caacatgggc aagaggcaat aaagggaata caatcggtat taactgaaag ttatgtgaaa    480
gaccattttc agttataaca aataaaataa aatcccaagc gtacaaagct gtttctaaaa    540
aaaaaaaaaa aaa                                                        553

<210> SEQ ID NO 84
<211> LENGTH: 133
<212> TYPE: PRT
<213> ORGANISM: Arabidopsis thaliana
<220> FEATURE:
<223> OTHER INFORMATION: G30 polypeptide

<400> SEQUENCE: 84

Met Asp Gln Gly Gly Arg Ser Ser Gly Ser Gly Gly Gly Gly Ala Glu
1               5                   10                  15

Gln Gly Lys Tyr Arg Gly Val Arg Arg Pro Trp Gly Lys Tyr Ala
        20                  25                  30

Ala Glu Ile Arg Asp Ser Arg Lys His Gly Glu Arg Val Trp Leu Gly
        35                  40                  45

Thr Phe Asp Thr Ala Glu Asp Ala Ala Arg Ala Tyr Asp Arg Ala Ala
    50                  55                  60

Tyr Ser Met Arg Gly Lys Ala Ala Ile Leu Asn Phe Pro His Glu Tyr
65                  70                  75                  80

Asn Met Gly Thr Gly Ser Ser Thr Ala Ala Asn Ser Ser Ser
                85                  90                  95

Ser Gln Gln Val Phe Glu Phe Glu Tyr Leu Asp Asp Ser Val Leu Asp
            100                 105                 110

Glu Leu Leu Glu Tyr Gly Glu Asn Tyr Asn Lys Thr His Asn Ile Asn
        115                 120                 125

Met Gly Lys Arg Gln
    130

<210> SEQ ID NO 85
<211> LENGTH: 964
<212> TYPE: DNA
<213> ORGANISM: Arabidopsis thaliana
<220> FEATURE:
<223> OTHER INFORMATION: G28
```

<400> SEQUENCE: 85

```
gaaatctcaa caagaaccaa accaaacaac aaaaaaacat tcttaataat tatctttctg    60
ttatgtcgat gacggcggat tctcaatctg attatgcttt tcttgagtcc atacgacgac   120
acttactagg agaatcggag ccgatactca gtgagtcgac agcgagttcg gttactcaat   180
cttgtgtaac cggtcagagc attaaaccgg tgtacgacg aaaccctagc tttagcaaac    240
tgtatccttg cttcaccgag agctggggag atttgccgtt gaaagaaaac gattctgagg   300
atatgttagt ttacggtatc ctcaacgacg ccttcacgg cggttgggag ccgtcttctt    360
cgtcttccga cgaagatcgt agctctttcc cgagtgttaa gatcgagact ccggagagtt   420
tcgcggcggt ggattctgtt ccggtcaaga aggagaagac gagtcctgtt tcggcggcgg   480
tgacggcggc gaagggaaag cattatagag gagtgagaca aaggccgtgg gggaaatttg   540
cggcggagat tagagatccg gcgaagaacg gagctagggt ttggttagga acgtttgaga   600
cggcggagga cgcggcgttg gcttacgaca gagctgcttt caggatgcgt ggttcccgcg   660
ctttgttgaa ttttccgttg agagttaatt caggagaacc cgacccggtt cgaatcaagt   720
ccaagagatc ttctttttct tcttctaacg agaacggagc tccgaagaag aggagaacgg   780
tggccgccgg tggtggaatg gataagggat tgacggtgaa gtgcgaggtt gttgaagtgg   840
cacgtgcga tcgtttattg gttttataat tttgattttt ctttgttgga tgattatatg    900
attcttcaaa aagaagaac gttaataaaa aaattcgttt attattaaaa aaaaaaaaaa   960
aaaa                                                               964
```

<210> SEQ ID NO 86
<211> LENGTH: 268
<212> TYPE: PRT
<213> ORGANISM: Arabidopsis thaliana
<220> FEATURE:
<223> OTHER INFORMATION: G28 polypeptide

<400> SEQUENCE: 86

```
Met Ser Met Thr Ala Asp Ser Gln Ser Asp Tyr Ala Phe Leu Glu Ser
1               5                   10                  15

Ile Arg Arg His Leu Leu Gly Glu Ser Glu Pro Ile Leu Ser Glu Ser
            20                  25                  30

Thr Ala Ser Ser Val Thr Gln Ser Cys Val Thr Gly Gln Ser Ile Lys
        35                  40                  45

Pro Val Tyr Gly Arg Asn Pro Ser Phe Ser Lys Leu Tyr Pro Cys Phe
    50                  55                  60

Thr Glu Ser Trp Gly Asp Leu Pro Leu Lys Glu Asn Asp Ser Glu Asp
65                  70                  75                  80

Met Leu Val Tyr Gly Ile Leu Asn Asp Ala Phe His Gly Gly Trp Glu
                85                  90                  95

Pro Ser Ser Ser Ser Asp Glu Asp Arg Ser Phe Pro Ser Val
            100                 105                 110

Lys Ile Glu Thr Pro Glu Ser Phe Ala Ala Val Asp Ser Val Pro Val
        115                 120                 125

Lys Lys Glu Lys Thr Ser Pro Val Ser Ala Ala Val Thr Ala Ala Lys
    130                 135                 140

Gly Lys His Tyr Arg Gly Val Arg Gln Arg Pro Trp Gly Lys Phe Ala
145                 150                 155                 160

Ala Glu Ile Arg Asp Pro Ala Lys Asn Gly Ala Arg Val Trp Leu Gly
                165                 170                 175
```

```
            Thr Phe Glu Thr Ala Glu Asp Ala Ala Leu Ala Tyr Asp Arg Ala Ala
                        180                 185                 190

Phe Arg Met Arg Gly Ser Arg Ala Leu Leu Asn Phe Pro Leu Arg Val
                        195                 200                 205

Asn Ser Gly Glu Pro Asp Pro Val Arg Ile Lys Ser Lys Arg Ser Ser
                        210                 215                 220

Phe Ser Ser Asn Glu Asn Gly Ala Pro Lys Lys Arg Arg Thr Val
            225                 230                 235                 240

Ala Ala Gly Gly Gly Met Asp Lys Gly Leu Thr Val Lys Cys Glu Val
                                245                 250                 255

Val Glu Val Ala Arg Gly Asp Arg Leu Leu Val Leu
                        260                 265

<210> SEQ ID NO 87
<211> LENGTH: 988
<212> TYPE: DNA
<213> ORGANISM: Arabidopsis thaliana
<220> FEATURE:
<223> OTHER INFORMATION: G133

<400> SEQUENCE: 87
ctcttcaaca aaagattaa acaaagagag aagaatatgg cgagagggaa gatccagatc      60
aagaggatag agaaccagac aaacagacaa gtgacgtatt caaagagaag gaatggttta    120
ttcaagaaag cacatgagct cacggttttg tgtgatgcta gggtttcgat tatcatgttc    180
tctagctcca acaagcttca tgagtatatc agccctaaca ccacaacgaa ggagatcgta    240
gatctgtacc aaactatttc tgatgtcgat gtttgggcca ctcaatatga gcgaatgcaa    300
gaaaccaaga ggaaactgtt ggagacaaat agaaatctcc ggactcagat caagcagagg    360
ctaggtgagt gtttggacga gcttgacatt caggagctgc gtcgtcttga ggatgaaatg    420
gaaaacactt tcaaactcgt tcgcgagcgc aagttcaaat ctcttgggaa tcagatcgag    480
accaccaaga aaaagaacaa aagtcaacaa gacatacaaa agaatctcat acatgagctg    540
gaactaagag ctgaagatcc tcactatgga ctagtagaca atggaggaga ttacgactca    600
gttcttggat accaaatcga agggtcacgt gcttacgctc ttcgtttcca ccagaaccat    660
caccactatt accccaacca tggccttcat gcaccctctg cctctgacat cattaccttc    720
catcttcttg aataattaaa ggctaaaagg tttgctggtg ccatcattgt ctatctaatt    780
atttagtaac tacttaaaac ataaggcatg gtgttgctaa aaccttaaac tgtcatgttt    840
cttagttatg tattttaaag cctaaagaaa tatggattgt gtgatcagta gtgcttaggc    900
ttattgtgtg tggaatgttt tcaagacttt tatcatgtat cgtattatta tattgaccac    960
tctacttaat tatgctacaa atttactc                                       988

<210> SEQ ID NO 88
<211> LENGTH: 232
<212> TYPE: PRT
<213> ORGANISM: Arabidopsis thaliana
<220> FEATURE:
<223> OTHER INFORMATION: G133 polypeptide

<400> SEQUENCE: 88

Met Ala Arg Gly Lys Ile Gln Ile Lys Arg Ile Glu Asn Gln Thr Asn
            1               5                  10                  15

Arg Gln Val Thr Tyr Ser Lys Arg Arg Asn Gly Leu Phe Lys Lys Ala
                        20                  25                  30

His Glu Leu Thr Val Leu Cys Asp Ala Arg Val Ser Ile Ile Met Phe
                        35                  40                  45
```

| | | | | | | | | | | | | |
|---|---|---|---|---|---|---|---|---|---|---|---|---|
| Ser | Ser | Ser | Asn | Lys | Leu | His | Glu | Tyr | Ile | Ser | Pro | Asn | Thr | Thr | Thr |
| | 50 | | | | 55 | | | | | 60 | | | | | |
| Lys | Glu | Ile | Val | Asp | Leu | Tyr | Gln | Thr | Ile | Ser | Asp | Val | Asp | Val | Trp |
| 65 | | | | | 70 | | | | | 75 | | | | | 80 |
| Ala | Thr | Gln | Tyr | Glu | Arg | Met | Gln | Glu | Thr | Lys | Arg | Lys | Leu | Leu | Glu |
| | | | | 85 | | | | | 90 | | | | | 95 | |
| Thr | Asn | Arg | Asn | Leu | Arg | Thr | Gln | Ile | Lys | Gln | Arg | Leu | Gly | Glu | Cys |
| | | | 100 | | | | | 105 | | | | | 110 | | |
| Leu | Asp | Glu | Leu | Asp | Ile | Gln | Glu | Leu | Arg | Arg | Leu | Glu | Asp | Glu | Met |
| | | 115 | | | | | 120 | | | | | 125 | | | |
| Glu | Asn | Thr | Phe | Lys | Leu | Val | Arg | Glu | Arg | Lys | Phe | Lys | Ser | Leu | Gly |
| | 130 | | | | | 135 | | | | | 140 | | | | |
| Asn | Gln | Ile | Glu | Thr | Thr | Lys | Lys | Lys | Asn | Lys | Ser | Gln | Gln | Asp | Ile |
| 145 | | | | | 150 | | | | | 155 | | | | | 160 |
| Gln | Lys | Asn | Leu | Ile | His | Glu | Leu | Glu | Leu | Arg | Ala | Glu | Asp | Pro | His |
| | | | | 165 | | | | | 170 | | | | | 175 | |
| Tyr | Gly | Leu | Val | Asp | Asn | Gly | Gly | Asp | Tyr | Asp | Ser | Val | Leu | Gly | Tyr |
| | | | 180 | | | | | 185 | | | | | 190 | | |
| Gln | Ile | Glu | Gly | Ser | Arg | Ala | Tyr | Ala | Leu | Arg | Phe | His | Gln | Asn | His |
| | | 195 | | | | | 200 | | | | | 205 | | | |
| His | His | Tyr | Tyr | Pro | Asn | His | Gly | Leu | His | Ala | Pro | Ser | Ala | Ser | Asp |
| | 210 | | | | | 215 | | | | | 220 | | | | |
| Ile | Ile | Thr | Phe | His | Leu | Leu | Glu | | | | | | | | |
| 225 | | | | | 230 | | | | | | | | | | |

```
<210> SEQ ID NO 89
<211> LENGTH: 1227
<212> TYPE: DNA
<213> ORGANISM: Arabidopsis thaliana
<220> FEATURE:
<223> OTHER INFORMATION: G1540

<400> SEQUENCE: 89
atctctttac taccagcaag ttgttttctt gctaacttca aacttctctt tctcttgttc      60
ctctctaagt cttgatctta tttaccgtta actttgtgaa caaaagtcga atcaaacaca     120
catggagccg ccacagcatc agcatcatca tcatcaagcc gaccaagaaa gcggcaacaa     180
caacaacaag tccggctctg gtggttacac gtgtcgccag accagcacga ggtggacacc     240
gacgacggag caaatcaaaa tcctcaaaga actttactac aacaatgcaa tccggtcacc     300
aacagccgat cagatccaga agatcactgc aaggctgaga cagttcggaa agattgaggg     360
caagaacgtc ttttactggt tccagaacca taaggctcgt gagcgtcaga agaagagatt     420
caacggaaca aacatgacca caccatcttc atcacccaac tcggttatga tggcggctaa     480
cgatcattat catcctctac ttcaccatca tcacggtgtt cccatgcaga gacctgctaa     540
ttccgtcaac gttaaactta accaagacca tcatctctat catcataaca agccatatcc     600
cagcttcaat aacgggaatt taaatcatgc aagctcaggt actgaatgtg gtgttgttaa     660
tgcttctaat ggctacatga gtagccatgt ctatggatct atggaacaag actgttctat     720
gaattacaac aacgtaggtg gaggatgggc aaacatggat catcattact catctgcacc     780
ttacaacttc ttcgatagag caaagcctct gtttggtcta gaaggtcatc aagacgaaga     840
agaatgtggt ggcgatgctt atctggaaca tcgacgtacg cttcctctct ccctatgca     900 cggtgaagat cacatcaacg gtggtagtgg tgccatctgg aagtatgcc aatcggaagt     960 tcgcccttgc gcttctcttg agctacgtct gaactagctc ttacgccggt gtcgctcggg    1020
```

```
attaaagctc tttcctctct ctctctcttt cgtactcgta tgttcacaac tatgcttcgc    1080
tagtgattaa tgatgcagtt gttatattag tagttaacta gttatctctc gttatgtgta    1140
atttgtaatt actagctaag tatcgtctag gtttaattgt aattgacaac cgtttatctc    1200
tatgatgaat aagttaaatt tatatat                                        1227
```

```
<210> SEQ ID NO 90
<211> LENGTH: 291
<212> TYPE: PRT
<213> ORGANISM: Arabidopsis thaliana
<220> FEATURE:
<223> OTHER INFORMATION: G1540 polypeptide

<400> SEQUENCE: 90
```

| | | | | | | | | | | | | | | |
|---|---|---|---|---|---|---|---|---|---|---|---|---|---|---|
| Met | Glu | Pro | Pro | Gln | His | Gln | His | His | His | Gln | Ala | Asp | Gln | Glu |
| 1 | | | | 5 | | | | | 10 | | | | | 15 |
| Ser | Gly | Asn | Asn | Asn | Lys | Ser | Gly | Ser | Gly | Gly | Tyr | Thr | Cys | Arg |
| | | | 20 | | | | | 25 | | | | | 30 | |
| Gln | Thr | Ser | Thr | Arg | Trp | Thr | Pro | Thr | Thr | Glu | Gln | Ile | Lys | Ile | Leu |
| | | 35 | | | | | 40 | | | | | 45 | | |
| Lys | Glu | Leu | Tyr | Tyr | Asn | Asn | Ala | Ile | Arg | Ser | Pro | Thr | Ala | Asp | Gln |
| 50 | | | | | 55 | | | | | 60 | | | | | |
| Ile | Gln | Lys | Ile | Thr | Ala | Arg | Leu | Arg | Gln | Phe | Gly | Lys | Ile | Glu | Gly |
| 65 | | | | 70 | | | | | 75 | | | | | 80 | |
| Lys | Asn | Val | Phe | Tyr | Trp | Phe | Gln | Asn | His | Lys | Ala | Arg | Glu | Arg | Gln |
| | | | | 85 | | | | | 90 | | | | | 95 | |
| Lys | Lys | Arg | Phe | Asn | Gly | Thr | Asn | Met | Thr | Thr | Pro | Ser | Ser | Ser | Pro |
| | | | 100 | | | | | 105 | | | | | 110 | | |
| Asn | Ser | Val | Met | Met | Ala | Ala | Asn | Asp | His | Tyr | His | Pro | Leu | Leu | His |
| | | 115 | | | | | 120 | | | | | 125 | | | |
| His | His | His | Gly | Val | Pro | Met | Gln | Arg | Pro | Ala | Asn | Ser | Val | Asn | Val |
| | 130 | | | | | 135 | | | | | 140 | | | | |
| Lys | Leu | Asn | Gln | Asp | His | His | Leu | Tyr | His | His | Asn | Lys | Pro | Tyr | Pro |
| 145 | | | | | 150 | | | | | 155 | | | | | 160 |
| Ser | Phe | Asn | Asn | Gly | Asn | Leu | Asn | His | Ala | Ser | Ser | Gly | Thr | Glu | Cys |
| | | | | 165 | | | | | 170 | | | | | 175 | |
| Gly | Val | Val | Asn | Ala | Ser | Asn | Gly | Tyr | Met | Ser | Ser | His | Val | Tyr | Gly |
| | | | 180 | | | | | 185 | | | | | 190 | | |
| Ser | Met | Glu | Gln | Asp | Cys | Ser | Met | Asn | Tyr | Asn | Asn | Val | Gly | Gly | Gly |
| | | 195 | | | | | 200 | | | | | 205 | | | |
| Trp | Ala | Asn | Met | Asp | His | His | Tyr | Ser | Ser | Ala | Pro | Tyr | Asn | Phe | Phe |
| | 210 | | | | | 215 | | | | | 220 | | | | |
| Asp | Arg | Ala | Lys | Pro | Leu | Phe | Gly | Leu | Glu | Gly | His | Gln | Asp | Glu | Glu |
| 225 | | | | | 230 | | | | | 235 | | | | | 240 |
| Glu | Cys | Gly | Gly | Asp | Ala | Tyr | Leu | Glu | His | Arg | Arg | Thr | Leu | Pro | Leu |
| | | | | 245 | | | | | 250 | | | | | 255 | |
| Phe | Pro | Met | His | Gly | Glu | Asp | His | Ile | Asn | Gly | Gly | Ser | Gly | Ala | Ile |
| | | | 260 | | | | | 265 | | | | | 270 | | |
| Trp | Lys | Tyr | Gly | Gln | Ser | Glu | Val | Arg | Pro | Cys | Ala | Ser | Leu | Glu | Leu |
| | | 275 | | | | | 280 | | | | | 285 | | | |
| Arg | Leu | Asn | | | | | | | | | | | | | |
| | | 290 | | | | | | | | | | | | | |

```
<210> SEQ ID NO 91
<211> LENGTH: 1275
<212> TYPE: DNA
```

<213> ORGANISM: Arabidopsis thaliana
<220> FEATURE:
<223> OTHER INFORMATION: G549

<400> SEQUENCE: 91

```
atggatcctg aaggtttcac gagtggctta ttccggtgga acccaacgag agcattggtt      60
caagcaccac ctccggttcc acctccgctg cagcaacagc cggtgacacc gcagacggct     120
gcttttggga tgcgacttgg tggtttagag ggactattcg gtccgtacgg tatacgtttc     180
tacacggcgg cgaagatagc ggagttaggt tttacggcga gcacgcttgt gggtatgaag     240
gacgaggagc ttgaagagat gatgaatagt ctctctcata tctttcgttg ggagcttctt     300
gttggtgaac ggtacggtat caaagctgcc gttagagctg aacggagacg attgcaagaa     360
gaggaggaag aggaatcttc tagacgccgt catttgctac tctccgccgc tggtgattcc     420
ggtactcatc acgctcttga tgctctctcc caagaagatg attggacagg ttatctgag      480
gaaccggtgc agcaacaaga ccagactgat gcggcgggga taacggcgg aggaggaagt      540
ggttactggg acgcaggtca aggaaagatg aagaagcaac agcagcagag acggagaaag     600
aaaccaatgc tgacgtcagt ggaaaccgac gaagacgtca acgaaggtga ggatgacgac     660
gggatggata acggcaacgg aggtagtggt ttggggacag agacagag ggagcatccg       720
tttatcgtaa cggagcctgg ggaagtggca cgtggcaaaa agaacggctt agattatctg     780
ttccacttgt acgaacaatg ccgtgagttc cttcttcagg tccagacaat tgctaaagac     840
cgtggcgaaa aatgccccac caaggtgacg aaccaagtat tcaggtacgc gaagaaatca     900
ggagcgagtt acataaacaa gcctaaaatg cgacactacg ttcactgtta cgctctccac     960
tgcctagacg aagaagcttc aaatgctctc agaagagcgt ttaaagaacg cggtgagaac    1020
gttggctcat ggcgtcaggc ttgttacaag ccacttgtga acatcgcttg tcgtcatggc    1080
tgggatatag acgccgtctt taacgctcat cctcgtctct ctatttggta tgttccaaca    1140
aagctgcgtc agctttgcca tttggagcgg aacaatgcgg ttgctgcggc tcggctttta    1200
gttggcggta ttagctgtac cggatcgtcg acgtctggac gtggtggatg cggcggcgac    1260
gacttgcgtt tctag                                                    1275
```

<210> SEQ ID NO 92
<211> LENGTH: 424
<212> TYPE: PRT
<213> ORGANISM: Arabidopsis thaliana
<220> FEATURE:
<223> OTHER INFORMATION: G549 polypeptide

<400> SEQUENCE: 92

```
Met Asp Pro Glu Gly Phe Thr Ser Gly Leu Phe Arg Trp Asn Pro Thr
1               5                   10                  15

Arg Ala Leu Val Gln Ala Pro Pro Val Pro Pro Leu Gln Gln
            20                  25                  30

Gln Pro Val Thr Pro Gln Thr Ala Ala Phe Gly Met Arg Leu Gly Gly
        35                  40                  45

Leu Glu Gly Leu Phe Gly Pro Tyr Gly Ile Arg Phe Tyr Thr Ala Ala
    50                  55                  60

Lys Ile Ala Glu Leu Gly Phe Thr Ala Ser Thr Leu Val Gly Met Lys
65                  70                  75                  80

Asp Glu Glu Leu Glu Glu Met Met Asn Ser Leu Ser His Ile Phe Arg
                85                  90                  95

Trp Glu Leu Leu Val Gly Glu Arg Tyr Gly Ile Lys Ala Ala Val Arg
            100                 105                 110
```

| | | | | | | | | | | | | |
|---|---|---|---|---|---|---|---|---|---|---|---|---|
|Ala|Glu|Arg|Arg|Arg|Leu|Gln|Glu|Glu|Glu|Glu|Ser|Ser|Arg|
| | |115| | | |120| | | |125| | | |
|Arg|Arg|His|Leu|Leu|Leu|Ser|Ala|Ala|Gly|Asp|Ser|Gly|Thr|His|His|
| |130| | | | |135| | | |140| | | | |
|Ala|Leu|Asp|Ala|Leu|Ser|Gln|Glu|Asp|Asp|Trp|Thr|Gly|Leu|Ser|Glu|
|145| | | | |150| | | | |155| | | | |160|
|Glu|Pro|Val|Gln|Gln|Gln|Asp|Gln|Thr|Asp|Ala|Ala|Gly|Asn|Asn|Gly|
| | | | |165| | | | |170| | | | |175| |
|Gly|Gly|Gly|Ser|Gly|Tyr|Trp|Asp|Ala|Gly|Gln|Gly|Lys|Met|Lys|Lys|
| | | |180| | | | |185| | | | |190| | |
|Gln|Gln|Gln|Gln|Arg|Arg|Lys|Lys|Pro|Met|Leu|Thr|Ser|Val|Glu|
| | |195| | | | |200| | | | |205| | |
|Thr|Asp|Glu|Asp|Val|Asn|Glu|Gly|Glu|Asp|Asp|Gly|Met|Asp|Asn|
| |210| | | | |215| | | | |220| | | |
|Gly|Asn|Gly|Gly|Ser|Gly|Leu|Gly|Thr|Glu|Arg|Gln|Arg|Glu|His|Pro|
|225| | | | |230| | | | |235| | | | |240|
|Phe|Ile|Val|Thr|Glu|Pro|Gly|Glu|Val|Ala|Arg|Gly|Lys|Lys|Asn|Gly|
| | | | |245| | | | |250| | | | |255| |
|Leu|Asp|Tyr|Leu|Phe|His|Leu|Tyr|Glu|Gln|Cys|Arg|Glu|Phe|Leu|Leu|
| | | |260| | | | |265| | | | |270| | |
|Gln|Val|Gln|Thr|Ile|Ala|Lys|Asp|Arg|Gly|Glu|Lys|Cys|Pro|Thr|Lys|
| | |275| | | | |280| | | | |285| | | |
|Val|Thr|Asn|Gln|Val|Phe|Arg|Tyr|Ala|Lys|Lys|Ser|Gly|Ala|Ser|Tyr|
| |290| | | | |295| | | | |300| | | | |
|Ile|Asn|Lys|Pro|Lys|Met|Arg|His|Tyr|Val|His|Cys|Tyr|Ala|Leu|His|
|305| | | | |310| | | | |315| | | | |320|
|Cys|Leu|Asp|Glu|Glu|Ala|Ser|Asn|Ala|Leu|Arg|Arg|Ala|Phe|Lys|Glu|
| | | | |325| | | | |330| | | | |335| |
|Arg|Gly|Glu|Asn|Val|Gly|Ser|Trp|Arg|Gln|Ala|Cys|Tyr|Lys|Pro|Leu|
| | | |340| | | | |345| | | | |350| | |
|Val|Asn|Ile|Ala|Cys|Arg|His|Gly|Trp|Asp|Ile|Asp|Ala|Val|Phe|Asn|
| | |355| | | | |360| | | | |365| | | |
|Ala|His|Pro|Arg|Leu|Ser|Ile|Trp|Tyr|Val|Pro|Thr|Lys|Leu|Arg|Gln|
| |370| | | | |375| | | | |380| | | | |
|Leu|Cys|His|Leu|Glu|Arg|Asn|Asn|Ala|Val|Ala|Ala|Ala|Ala|Leu|
|385| | | | |390| | | | |395| | | | |400|
|Val|Gly|Gly|Ile|Ser|Cys|Thr|Gly|Ser|Ser|Thr|Ser|Gly|Arg|Gly|Gly|
| | | | |405| | | | |410| | | | |415| |
|Cys|Gly|Gly|Asp|Asp|Leu|Arg|Phe|
| | | |420| | | | |

<210> SEQ ID NO 93
<211> LENGTH: 859
<212> TYPE: DNA
<213> ORGANISM: Arabidopsis thaliana
<220> FEATURE:
<223> OTHER INFORMATION: G1266

<400> SEQUENCE: 93

```
caatccacta acgatcccta accgaaaaca gagtagtcaa gaaacagagt attttttcta      60
catggatcca tttttaattc agtccccatt ctccggcttc tcaccggaat attctatcgg     120
atcttctcca gattctttct catcctcttc ttctaacaat tactctcttc ccttcaacga     180
gaacgactca gaggaaatgt ttctctacgg tctaatcgag cagtccacgc aacaaaccta     240
tattgactcg gatagtcaag accttccgat caaatccgta agctcaagaa agtcagagaa     300
```

```
gtcttacaga ggcgtaagac gacggccatg ggggaaattc gcggcggaga taagagattc    360
gactagaaac ggtattaggg tttggctcgg gacgttcgaa agcgcggaag aggcggcttt    420
agcctacgat caagctgctt ctctcgatga gagggtcctcg gcgattctca attttttcggc   480 ggagagagtt caagagtcgc tttcggagat taaatatacc tacgaggatg gttgttctcc    540
ggttgtggcg ttgaagagga aacactcgat gagacggaga atgaccaata agaaacgaa    600 agatagtgac tttgatcacc gctccgtgaa gttagataat gtagttgtct ttgaggattt    660
gggagaacag taccttgagg agcttttggg gtcttctgaa atagtggga cttggtgaaa     720 gattaggatt tgtattaggg accttaagtt tgaagtggtt gattaatttt aaccctaata    780
tgttttttgt ttgcttaaat atttgattct attgagaaac atcgaaaaca gtttgtatgt    840
acttttgtga tacttggcg                                                  859
```

<210> SEQ ID NO 94
<211> LENGTH: 218
<212> TYPE: PRT
<213> ORGANISM: Arabidopsis thaliana
<220> FEATURE:
<223> OTHER INFORMATION: G1266 polypeptide

<400> SEQUENCE: 94

```
Met Asp Pro Phe Leu Ile Gln Ser Pro Phe Ser Gly Phe Ser Pro Glu
1               5                   10                  15

Tyr Ser Ile Gly Ser Ser Pro Asp Ser Phe Ser Ser Ser Ser Asn
            20                  25                  30

Asn Tyr Ser Leu Pro Phe Asn Glu Asn Asp Ser Glu Glu Met Phe Leu
        35                  40                  45

Tyr Gly Leu Ile Glu Gln Ser Thr Gln Gln Thr Tyr Ile Asp Ser Asp
    50                  55                  60

Ser Gln Asp Leu Pro Ile Lys Ser Val Ser Ser Arg Lys Ser Glu Lys
65                  70                  75                  80

Ser Tyr Arg Gly Val Arg Arg Pro Trp Gly Lys Phe Ala Ala Glu
                85                  90                  95

Ile Arg Asp Ser Thr Arg Asn Gly Ile Arg Val Trp Leu Gly Thr Phe
            100                 105                 110

Glu Ser Ala Glu Glu Ala Ala Leu Ala Tyr Asp Gln Ala Ala Phe Ser
        115                 120                 125

Met Arg Gly Ser Ser Ala Ile Leu Asn Phe Ser Ala Glu Arg Val Gln
    130                 135                 140

Glu Ser Leu Ser Glu Ile Lys Tyr Thr Tyr Glu Asp Gly Cys Ser Pro
145                 150                 155                 160

Val Val Ala Leu Lys Arg Lys His Ser Met Arg Arg Met Thr Asn
                165                 170                 175

Lys Lys Thr Lys Asp Ser Asp Phe Asp His Arg Ser Val Lys Leu Asp
            180                 185                 190

Asn Val Val Phe Glu Asp Leu Gly Glu Gln Tyr Leu Glu Glu Leu
        195                 200                 205

Leu Gly Ser Ser Glu Asn Ser Gly Thr Trp
    210                 215
```

<210> SEQ ID NO 95
<211> LENGTH: 1216
<212> TYPE: DNA
<213> ORGANISM: artificial sequence
<220> FEATURE:
<223> OTHER INFORMATION: artificial sequence

```
<220> FEATURE:
<223> OTHER INFORMATION: P26708-direct promoter-fusion of prAT5G24090
      to G1795 coding sequence

<400> SEQUENCE: 95
aaatggtcca gttttggccc aaatatttaa caacatttgg gttacgagta tttgcccttt     60
acaaatggat caacaatctc cctggatcaa tatttagtgg ccggtttcat gaatcaacat    120
attctttttt tttttttgtc taaagaatca acatattcta aatcaccaaa acactttggt    180
caacaatttt cgacaatata tggaaattag gttggattat catgcgactt ttttctgatt    240
aattttatgt attttttaatt tacgatgtaa ttcggactac taatttgtat tatgataact    300
ttacattttc catactactc aagtccaagt aaaatactat tgtatatata tctttggatt    360
ttacataaat taatggggag gcctaataaa atatactcgg agtatatcat ttgactttga    420
aatttatcga gtcaaatcaa tgattgtatt tttggtaaaa acaattatta tgaagacttt    480
gaaagttttt aatgatttta atttcaaaaa ttagtaaatg ctggtctggt tatccatcca    540
ttggaagaga aataagacc ttttcaaagc tagttgataa aaaaagttct cggtcctatc    600
cctcatctta taagaaatt attaatacgt ttagggattc aattcacaga agatttaaaa    660
acaaatggaa aataggatat taccataata attatggttc aacaacaatt tcgatttcta    720
atttgaataa tggaaattta gatcaaaaat agttccgact catagataaa ttgaaatgtg    780
ccaaatgtca cgtaaaccag caagaggaca aagtcaacac cacaagagac gacgacgagc    840
acagtgtgag gttatgatat ataccctctg cgagactgcg actgctatta ctgatttgat    900
cccaagtttt tttttttttt ttgaaattta ttttttcttt atacacaatt acatagtggt    960
aagagattct agatggcttc ttaatgtttg agatttatat ctagtttaag taggaaagct   1020
atattatttg aagaaagaaa aaaacaacca atcaaagtca tgcaatgtgt gtgagagaca   1080
ttataacata catagataag atataaaat taaagcaaac aaaagtcata ttttacttct   1140
tttataaaaa aagaagttaa gcaataacaa acaaacacat aaccacaaag aagacaaaac   1200
atctttaacc aaaaac                                                   1216

<210> SEQ ID NO 96
<211> LENGTH: 1207
<212> TYPE: DNA
<213> ORGANISM: artificial sequence
<220> FEATURE:
<223> OTHER INFORMATION: artificial sequence
<220> FEATURE:
<223> OTHER INFORMATION: P26707-direct promoter-fusion of prAT5G62150 to
      G1795 coding sequence

<400> SEQUENCE: 96
tggtatatgc acgacaggac aaccgataca atgacagttg gttccaaaaa aaaagtttaa     60
tcctaaatat atgaataatc gaatcgatca ataacacgtt gacaaaaaac gaacaaataa    120
tcacactgat gaaccacttt ataatgaaca gagaattttg taatctgaaa attttgaaag    180
tcaagaggtt aatcaagtaa ttatagaaag gtagttgtaa cgttggcttt tgtggaacta    240
ataacttacg tgtctttaaa cggcggctac tttggaaggc tacgtttctt aatttgaacc    300
tcattttctc cattttcctt cgttatacg atatcttttt caaaaaagtg acccaataac    360
cacacatata acatatttag tataactttg aatataaacg aatcaatgat atctgaattt    420
tattttgatt ttgatcttga tttttgttgt tttttgtcga ggctattgcc ttgccacttt    480
ggatgaagga acccggctaa ggtaagaccc cctgcctaat attagcctcc ggcgaatttt    540
gcactcagaa attacattat gttatagttt tggaattta gtttaaattt gtaaaagtat    600
```

```
taaaacaatt ggtcaactat tatattaatt agctcaagag tgctttcaaa aacatatctt        660
aaatttaata aagaaatatt ccaatatctt aaccagtact aaaagagaag atcagaaaat        720
ttcttataaa actttaatct aataaaatca tctacgactc taccattcaa tattttttg         780 ttattgtttt atttacatat ttcttttaat atttacatat ctcttttcct ttttgctaaa        840
aaaaagttgg cataaaaatt actaaatttt aagcgtaaaa aaataaaatt aattattgtc        900
tattgccatt tttggaggat ggatatgatt tggaggaata gttaaagaaa gtgctaaaat        960
ctcctttagt gagtcacaac cgttgacctt caccgcaagg cacaagagac caagtctcta       1020
acccaacaca acacaaaacc cataaactga aaagactaac ctaccctatc ttgccatata       1080
aatccctctc gagcaacgca tgttaaataa acctaattta tacattcatt ctcaaagtca       1140
aaaggagaca gggagagaga gagagagaga gagaattcaa agcgtttttt ttttataaat       1200
taaaggc                                                                 1207
```

<210> SEQ ID NO 97
<211> LENGTH: 1222
<212> TYPE: DNA
<213> ORGANISM: artificial sequence
<220> FEATURE:
<223> OTHER INFORMATION: artificial sequence
<220> FEATURE:
<223> OTHER INFORMATION: prAT3G23550 disease inducible promoter

<400> SEQUENCE: 97

```
aatgatgttg attatgggag aatcttgcta gattctttag tcaaaagaat tggagttctt         60
agactctcat aggaagggaa gatcttcccc accattcctt acacgcaacg tgagttatct        120
agaatttagc ttctacctgc tcttgagtct tagcaagtca aagattagta gcagcagtgc        180
agcacactat taacaattac atcaaccatc agcgtcagaa gacaatttaa ccagactaat        240
attctctaaa atgttagccg tttattttga attttttgat ggccggaaac taactcttta        300
ctacttgatg gtagtagggt tggcttactt ggtgggagct acaatggttc cgcagccggc        360
cccaactctt gaactctagg agttttttt gttcttccat tatattgttt tctttctttt         420
ttttcgaaaa aaactcttcc attataatgt cggtttttt tttatttgga taatggcaca        480
accatatcat tactgtaaac caatccggta aaaaaaaat agaatttaaa caattataaa         540
taaaatttgg taatggtagg atcagccatt atggtcatct ttggacgtgg gatcagccat        600
tgtaatgtct atagggcggc ctaaagaaaa atcctcccaa aacctctaaa taatattgag        660
ccggcagaag gaccaccaca cttgcacaca tcataatcag aagctaagtc ctaaatatgt        720
atatatatcc acttgattcc taatatacat ttttttttt gttaaaatac ctaatataca         780
taagaataag atgtatatac ttacaagatt ttataaaag aaactaaaga tgatatatat         840
atcaaatata tgtacataac acttgattcc taatccaagc actaattctg gctttgtcta        900
cttggtgagt catgattcat gagtgttaat attaaattca taaatgtgtc tctgtgtctt        960
aatattttag ttctgtgttt aatattttca taaactattt ttgcgtacct ttcttatttt       1020
atacttactt ttctttttt ccctcgtgtt tgtgcatgga gagtcgaaat tggttggctt       1080
ctcctctgac agagacaggc cctttgaaca tatccaatta aaaagctctc cacttactcc       1140
ttatatagtt cttcaccttt acaaataaaa atttgtctag cttctcctac tcttcgccag       1200
atccaaattc cttgaagata ca                                               1222
```

<210> SEQ ID NO 98
<211> LENGTH: 657

-continued

```
<212> TYPE: DNA
<213> ORGANISM: artificial sequence
<220> FEATURE:
<223> OTHER INFORMATION: artificial sequence
<220> FEATURE:
<223> OTHER INFORMATION: prAT4G11890 disease inducible promoter

<400> SEQUENCE: 98
tcttaaagtc cttttacact tggtctagac ccaaaaatcg ttggctttct atgatcggtc      60
tttgtcagcg tgtcatttac gtgacgtggt tggtttggtt cgaaatttct aagtagctga     120
aaattcagtt ccgttccttc caagaacatc atcttgaagt agaattcttt gtgacaaaca     180
aaaaaaaatg gtagaattct atggttatat atatatatat atatatatat atatatatgt     240
ttattataac aacagaccta atatcttcta tgttttatgt aatatctatt tattttttgt     300
tatttattga acctacatac aaataaaaca aaacaaagta aacttctaaa taatatattt     360
ttcattttca ttttagttga aatataattt gattttcaat accaaactat ataatatcaa     420
tattcagaat aagttaattg ttacgtatta aaaacaatgc aagaacaaat gaagaagcca     480
aaatatccaa aatgaatagt agaagtcaag gtcaacatag tggactctaa caatatcaac     540
gaagtcaacc gttgaagaaa ttaaataact tgtctaataa gttcttcttt tttcttggat     600
taaatacttg tttgaagcaa attcagagac actgtcttcg tcttcatctt tgctatg       657
```

DISEASE-INDUCIBLE PROMOTERS

CROSS REFERENCE TO RELATED APPLICATIONS

Figure 1:
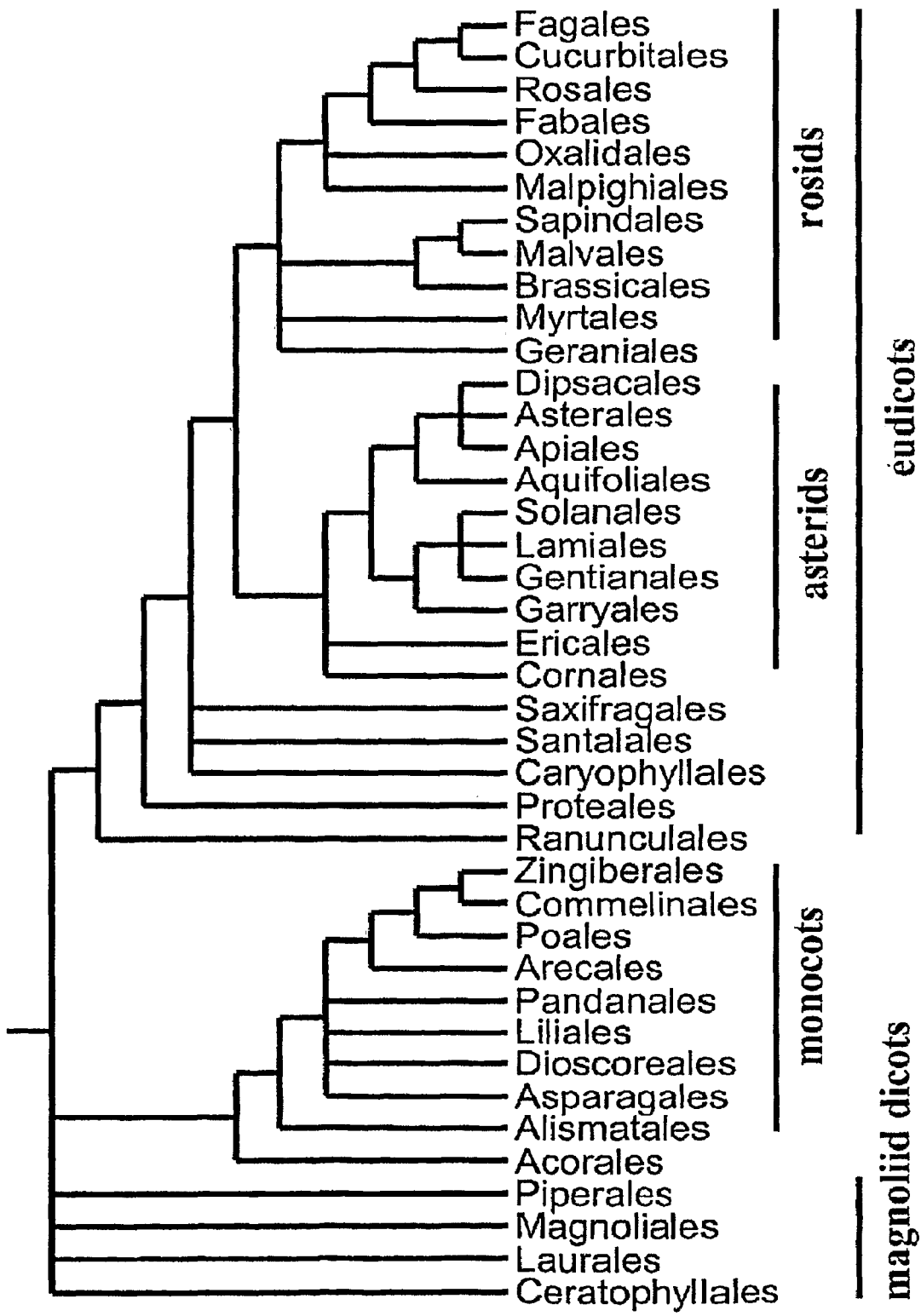

This is a U.S. National Phase patent application of PCT/US2007/009890, filed Apr. 23, 2007, which claims priority to U.S. Provisional patent application Ser. No. 60/794,671, filed Apr. 24, 2006, all of which are hereby incorporated by reference in the present disclosure in their entirety.

JOINT RESEARCH AGREEMENT

The claimed invention, in the field of functional genomics and the characterization of plant genes for the improvement of plants, was made by or on behalf of Mendel Biotechnology, Inc. and Monsanto Corporation as a result of activities undertaken within the scope of a joint research agreement in effect on or before the date the claimed invention was made.

FIELD OF THE INVENTION

The present invention relates to plant genomics and more specifically pertains to disease-inducible promoters that mediate gene expression during a plant's response to pathogens.

BACKGROUND OF THE INVENTION

Protection of crops against fungal pathogens is one of the most significant unmet needs in agriculture. Despite these significant losses, less than 5 percent of U.S. corn and soybean acreage is treated with fungicides (Gianessi and Marcelli (2000) Pesticide Use in U.S. Crop Production: 1997, National Summary Report, November, 2000), for agronomic reasons and due to the diverse nature of the pathogens responsible for those losses.

In conventional pathogen-resistant crop varieties, resistance is achieved by using standard breeding techniques to introgress resistance (R) genes, which recognize or interact with pathogen virulence factors and activate defense responses, from wild germplasm into domesticated germplasm. However, R gene-mediated resistance is not usually durable because the pathogen mutates, eliminating the virulence factor detected by the plant. Since virulence factors appear to have redundant functions, individual factors can be lost with little, if any, diminished pathogenicity. Only in a few rare cases is durable resistance observed, and this is usually attributed to an essential function of a given virulence factor in the host-pathogen interaction. Moreover, and very importantly, R gene-medicated resistance protects crops against a limited spectrum of fungal pathogens. Most crops suffer from multiple pathogen problems, so that the industry seeks broad-spectrum, durable disease solutions.

The expression of the defense response can be engineered by altering the expression of regulatory proteins such as transcription factors (reviewed in Gurr and Rushton (2005) Trends Biotechnol. 23: 275-282). We have previously shown that constitutive and ectopic overexpression of key transcription factors involved in the natural defense response results in enhanced disease resistance in transgenic plants (e.g., see U.S. Pat. No. 6,664,446 or US Patent Application 20030046723). In many instances, the gain of function phenotype (disease resistance) is observed in interactions with multiple fungal and bacterial pathogens, a major advantage for the engineering of this trait in crops. This provides experimental evidence that altering the expression of natural defense responses is an effective method for engineering disease resistance in plants.

The applicability of this technology to crop species may be limited by negative side effects associated with constitutive overexpression of disease defense protein(s). Pleiotropic effects such as delayed growth and development and alteration in flowering time are common. It has been proposed that genes conferring resistance to pathogens impose a cost on overall fitness and development. Plants have achieved a balance between fitness and resistance by the evolution of inducible defenses.

The development of effective resistance of crops to different classes of pathogens will require the dissociation of the gain of function phenotype (disease resistance) from the negative side effects. We hypothesize that limiting overexpression of disease resistance transcription factors to infected tissues, only when disease pressure arises, will significantly reduce or eliminate the impact on yield and fitness, while retaining the gain of function phenotype. The present invention addresses the difficulties in identifying promoters with unique expression characteristics for applicability in the development of disease resistance in crops. We believe that the solution to this technical problems lies with the selection of plant promoters with key expression characteristics. These promoters may also be useful for controlled expression of other defense regulatory proteins, antimicrobial proteins, elicitors that induce defense responses, etc.

SUMMARY OF THE INVENTION

The present invention is directed to a recombinant polynucleotide that comprising any of the promoter sequences of the invention, including SEQ ID NOs: 22, 12, 23, 32,19, 1, 2, 3, 4, 5, 6, 7, 8, 9, 10, 11, 13, 14, 15, 16, 17, 18, 20, 21, 24, 25, 26, 27, 28, 29, 30, 31, 33, 34, 35, 36, 37, 38 or 39.

Generally, the promoter is an RNA polymerase binding site that is located 5' relative to and operably linked to a nucleic acid sequence that is responsible for conferring improved resistance to a plant disease. For example, the nucleic acid sequence may be a natural or artificial disease resistance (R) gene, or an avr gene. The nucleic acid sequence may also encode a polypeptide that is a transcription factor, a kinase, a phosphatase, an enzyme producing a fungitoxic compound, an enzyme producing a phytoalexin, a fungicidal protein, a bactericidal protein, or a natural or artificial inducer of programmed cell death.

The present invention is also directed to an expression vector comprising a recombinant polynucleotide comprising any of the promoter sequences of the invention, including SEQ ID NOs: 22, 12, 23, 32, 19, 1, 2, 3, 4, 5, 6, 7, 8, 9, 10, 11, 13, 14, 15, 16, 17, 18, 20, 21, 24, 25, 26, 27, 28, 29, 30, 31, 33, 34, 35, 36, 37, 38 or 39.

The present invention also pertains to a transgenic plant comprising a recombinant polynucleotide comprising any of the promoter sequences of the invention, including SEQ ID NOs: 22, 12, 23, 32, 19, 1, 2, 3, 4, 5, 6, 7, 8, 9, 10, 11, 13, 14, 15, 16, 17, 18, 20, 21, 24, 25, 26, 27, 28, 29, 30, 31, 33, 34, 35, 36, 37, 38 or 39, as well as a transgenic seed that may be produced by this transgenic plant.

The present invention is also encompassed by a method for producing a transgenic plant having greater resistance to a pathogen than a control plant. The method steps include generating an expression vector comprising a promoter sequence comprising any of SEQ ID NOs: 22, 12, 23, 32, 19, 1, 2, 3, 4, 5, 6, 7, 8, 9, 10, 11, 13, 14, 15, 16, 17, 18, 20, 21, 24, 25, 26, 27, 28, 29, 30, 31, 33, 34, 35, 36, 37, 38 or 39, where the promoter sequence is operably linked to a nucleotide sequence that encodes a polypeptide that regulates a defense response in a plant; and then transforming a target plant with the expression vector to produce a transgenic plant that has greater resistance to the pathogen than the control plant.

BRIEF DESCRIPTION OF THE SEQUENCE LISTING AND DRAWINGS

The Sequence Listing provides exemplary polynucleotide and polypeptide sequences of the invention. The traits associated with the use of the sequences are included in the Examples.

CD-ROMs Copy 1 and Copy 2, and the CRF copy of the Sequence Listing under CFR Section 1.821(e), are read-only memory computer-readable compact discs. Each contains a copy of the Sequence Listing in ASCII text format. The Sequence Listing is named "MB10078PCT.ST25.txt", the electronic file of the Sequence Listing contained on each of these CD-ROMs was created on Apr. 4, 2007, and is 151 kilobytes in size. The copies of the Sequence Listing on the CD-ROM discs are hereby incorporated by reference in their entirety.

FIG. 1 shows a conservative estimate of phylogenetic relationships among the orders of flowering plants (modified from Soltis et al. (1997) *Ann. Missouri Bot. Gard.* 84: 1-49). Those plants with a single cotyledon (monocots) are a monophyletic lade nested within at least two major lineages of dicots; the eudicots are further divided into rosids and asterids. *Arabidopsis* is a rosid eudicot classified within the order Brassicales; rice is a member of the monocot order Poales. FIG. 1 was adapted from Daly et al. (2001) *Plant Physiol.* 127: 1328-1333.

Figure 2:
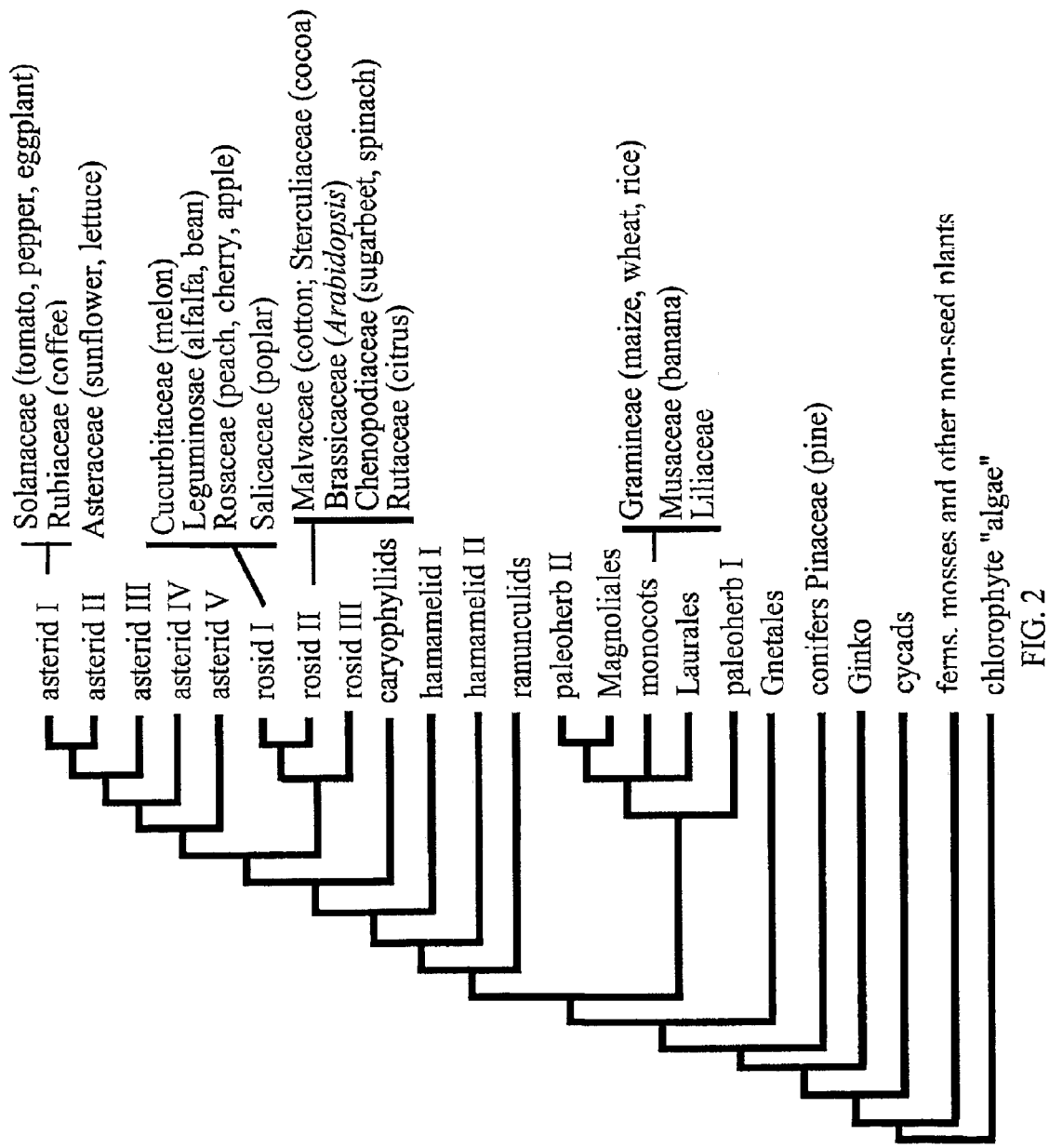

FIG. 2 shows a phylogenic dendogram depicting phylogenetic relationships of higher plant taxa, including clades containing tomato and *Arabidopsis*; adapted from Ku et al. (2000) *Proc. Natl. Acacd. Sci. USA* 97: 9121-912; and Chase et al. (1993) *Ann. Missouri Bot. Gard.* 80: 528-580.

Figure 3:
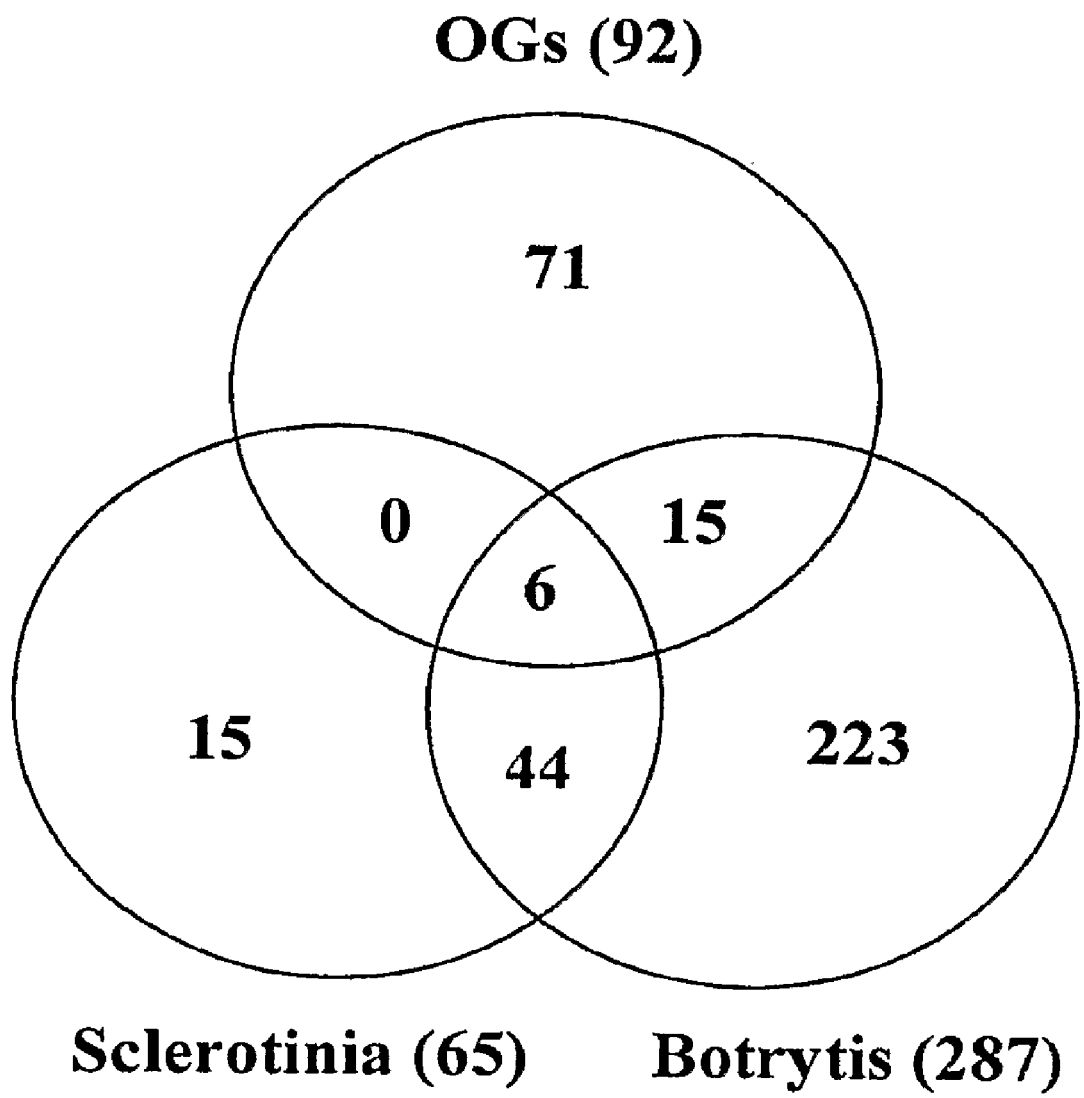

FIG. 3 shows a Venn diagram illustrating the relationships among genes with sustained expression versus *Sclerotinia*, *Botrytis* or oligogalacturonide (OG) treatments.

Figure 4:

FIG. 4 compares transgenic prAT1G35230::G1795 *Arabidopsis* seedlings on the left side of this plate with wild-type control seedlings on the right side of the plate. All seedlings were challenged with the necrotrophic pathogen *Sclerotinia sclerotiorum*. In this experiment, this line of overexpressors resisted infection by *Sclerotinia*. However, the control plants were significantly and obviously infected. When constitutively overexpressed, the AP2 family transcription factor G1795 (polynucleotide SEQ ID NO: 77 and polypeptide SEQ ID NO: 78) confers significant disease resistance but generally also produces significant dwarfing. However, when the G1795 polynucleotide was overexpressed under the regulatory control of the disease-inducible prAT1G35230 promoter (promoter SEQ ID NO: 22, expression vector SEQ ID NO: 59), prAT1G35230::G1795 overexpressors were generally of similar morphology at similar stages of growth as the controls (not shown). This line was also much more resistant to the biotrophic pathogen *Erysiphe* than wild type plants (not shown).

Figure 5:

FIG. 5 compares nine transgenic plants (lower left, upper left and upper right quadrants) overexpressing the transcription factor G1795 under the regulatory control of the novel disease-inducible prAT3G02840 promoter (promoter SEQ ID NO: 32, expression vector SEQ ID NO: 69) with three wild-type control *Arabidopsis* plants (lower right quadrant), all challenged with the biotrophic pathogen *Erysiphe orontii*, eight days after inoculation. When constitutively expressed, G11795 confers disease resistance but also produces dwarfed, dark green plants. However, prAt3G02840::G1795 overexpressors were generally of the same size and reached the late rosette stage after growing for about the same period of time as the controls. The overexpressing plants in this line also appeared to be free of disease symptoms, unlike the control plants that were visibly and significantly infected. These results demonstrated that transgenic plant lines can be generated and selected that overexpress a transcription factor under the regulatory control of an inducible promoter, while producing plants with significant disease resistance and minimal adverse growth or developmental effects. This line of overexpressors was also more resistant to the necrotrophic pathogen *Sclerotinia* (data not shown).

Figure 6:

In FIG. 6, the nine transgenic plants overexpressing G1795 under the regulatory control of another disease-inducible promoter, prAT1G02360 (promoter SEQ ID NO: 19, expression vector SEQ ID NO: 56; lower left, upper left and upper right quadrants), were generally of the same size and development stage (late rosette) as the three control plants in the lower right quadrant. Unlike the control plants that were visibly infected eight days after inoculation, the transgenic plants appeared to be nearly disease free after inoculation with *Erysiphe orontii*. This line of overexpressors was also significantly more resistant to the necrotrophic pathogen *Sclerotinia* (data not shown).

DETAILED DESCRIPTION

The present invention relates to polynucleotides and polypeptides for modifying phenotypes of plants, particularly promoter sequences associated with increased resistance to pathogens and/or disease, and/or increased yield with respect to a control plant (for example, a genetically unaltered or non-transgenic plant such as a wild-type plant of the same species, or a transgenic plant line that comprises an empty expression vector). Throughout this disclosure, various information sources are referred to and/or are specifically incorporated. The information sources include scientific journal articles, patent documents, textbooks, and World Wide Web page addresses. While the reference to these information sources clearly indicates that they can be used by one of skill in the art, each and every one of the information sources cited herein are specifically incorporated in their entirety, whether or not a specific mention of "incorporation by reference" is noted. The contents and teachings of each and every one of the information sources can be relied on and used to make and use embodiments of the invention.

As used herein and in the appended claims, the singular forms "a", "an", and "the" include the plural reference unless the context clearly dictates otherwise. Thus, for example, a reference to "a host cell" includes a plurality of such host cells, and a reference to "a stress" is a reference to one or more stresses and equivalents thereof known to those skilled in the art, and so forth.

Definitions

"Nucleic acid molecule" refers to an oligonucleotide, polynucleotide or any fragment thereof. It may be DNA or RNA of genomic or synthetic origin, double-stranded or single-stranded, and combined with carbohydrate, lipids, protein, or other materials to perform a particular activity such as transformation or form a useful composition such as a peptide nucleic acid (PNA).

"Polynucleotide" is a nucleic acid molecule comprising a plurality of polymerized nucleotides, e.g., at least about 15 consecutive polymerized nucleotides. A polynucleotide may be a nucleic acid, oligonucleotide, nucleotide, or any fragment thereof. In many instances, a polynucleotide comprises a nucleotide sequence encoding a polypeptide (or protein) or a domain or fragment thereof. Additionally, the polynucleotide may comprise a promoter, an intron, an enhancer region, a polyadenylation site, a translation initiation site, 5' or 3' untranslated regions, a reporter gene, a selectable marker, or the like. The polynucleotide can be single-stranded or double-stranded DNA or RNA. The polynucleotide optionally comprises modified bases or a modified backbone. The polynucleotide can be, e.g., genomic DNA or RNA, a transcript (such as an mRNA), a cDNA, a PCR product, a cloned DNA, a synthetic DNA or RNA, or the like. The polynucleotide can be combined with carbohydrate, lipids, protein, or other materials to perform a particular activity such as transformation or form a useful composition such as a peptide nucleic acid (PNA). The polynucleotide can comprise a sequence in either sense or antisense orientations. "Oligonucleotide" is substantially equivalent to the terms amplimer, primer, oligomer, element, target, and probe and is preferably single-stranded.

A "recombinant polynucleotide" is a polynucleotide that is not in its native state, e.g., the polynucleotide comprises a nucleotide sequence not found in nature, or the polynucleotide is in a context other than that in which it is naturally found, e.g., separated from nucleotide sequences with which it typically is in proximity in nature, or adjacent (or contiguous with) nucleotide sequences with which it typically is not in proximity. For example, the sequence at issue can be cloned into a vector, or otherwise recombined with one or more additional nucleic acid.

An "isolated polynucleotide" is a polynucleotide, whether naturally occurring or recombinant, that is present outside the cell in which it is typically found in nature, whether purified or not. Optionally, an isolated polynucleotide is subject to one or more enrichment or purification procedures, e.g., cell lysis, extraction, centrifugation, precipitation, or the like.

"Gene" or "gene sequence" refers to the partial or complete coding sequence of a gene, its complement, and its 5' or 3' untranslated regions. A gene is also a functional unit of inheritance, and in physical terms is a particular segment or sequence of nucleotides along a molecule of DNA (or RNA, in the case of RNA viruses) involved in producing a polypeptide chain. The latter may be subjected to subsequent processing such as chemical modification or folding to obtain a functional protein or polypeptide. A gene may be isolated, partially isolated, or found with an organism's genome. By way of example, a transcription factor gene encodes a transcription factor polypeptide, which may be functional or require processing to function as an initiator of transcription.

Operationally, genes may be defined by the cis-trans test, a genetic test that determines whether two mutations occur in the same gene and that may be used to determine the limits of the genetically active unit (Rieger et al. (1976) *Glossary of Genetics and Cytogenetics: Classical and Molecular*, 4th ed., Springer Verlag, Berlin). A gene generally includes regions preceding ("leaders"; upstream) and following ("trailers"; downstream) the coding region. A gene may also include intervening, non-coding sequences, referred to as "introns", located between individual coding segments, referred to as "exons". Most genes have an associated promoter region, a regulatory sequence 5' of the transcription initiation codon (there are some genes that do not have an identifiable promoter). The function of a gene may also be regulated by enhancers, operators, and other regulatory elements.

A "promoter" or "promoter region" refers to an RNA polymerase binding site on a segment of DNA, generally found upstream or 5' relative to a coding sequence under the regulatory control of the promoter. Promoters regulate expression of the coding sequences under their regulatory control by providing a recognition site for RNA polymerase and/or other factors necessary for start of transcription at the correct site. A promoter or promoter region may include variations of promoters found in the present Sequence Listing, which may be derived by ligation to other regulatory sequences, random mutagenesis, controlled mutagenesis, and/or by the addition or duplication of enhancer sequences. Promoters disclosed in the present Sequence Listing and biologically functional equivalents or variations thereof may drive the transcription of operably-linked coding sequences when comprised within an expression vector and introduced into a host plant. Promoters such as those found in the Sequence Listing (i.e., SEQ ID NOs: 1-39) may be used to generate disease-inducible promoters containing essential promoter elements.

A "polypeptide" is an amino acid sequence comprising a plurality of consecutive polymerized amino acid residues e.g., at least about 15 consecutive polymerized amino acid residues. In many instances, a polypeptide comprises a polymerized amino acid residue sequence that is a transcription factor or a domain or portion or fragment thereof. Additionally, the polypeptide may comprise: (i) a localization domain; (ii) an activation domain; (iii) a repression domain; (iv) an oligomerization domain; (v) a DNA-binding domain; or the like. The polypeptide optionally comprises modified amino acid residues, naturally occurring amino acid residues not encoded by a codon, non-naturally occurring amino acid residues.

"Protein" refers to an amino acid sequence, oligopeptide, peptide, polypeptide or portions thereof whether naturally occurring or synthetic.

A "recombinant polypeptide" is a polypeptide produced by translation of a recombinant polynucleotide. A "synthetic polypeptide" is a polypeptide created by consecutive polymerization of isolated amino acid residues using methods well known in the art. An "isolated polypeptide," whether a naturally occurring or a recombinant polypeptide, is more enriched in (or out of) a cell than the polypeptide in its natural state in a wild-type cell, e.g., more than about 5% enriched, more than about 10% enriched, or more than about 20%, or more than about 50%, or more, enriched, i.e., alternatively denoted: 105%, 110%, 120%, 150% or more, enriched relative to wild type standardized at 100%. Such an enrichment is not the result of a natural response of a wild-type plant. Alternatively, or additionally, the isolated polypeptide is separated from other cellular components with which it is typically associated, e.g., by any of the various protein purification methods herein.

"Homology" refers to sequence similarity between a reference sequence and at least a fragment of a newly sequenced clone insert or its encoded amino acid sequence.

"Identity" or "similarity" refers to sequence similarity between two polynucleotide sequences or between two polypeptide sequences, with identity being a more strict comparison. The phrases "percent identity" and "% identity" refer to the percentage of sequence similarity found in a comparison of two or more polynucleotide sequences or two or more polypeptide sequences. "Sequence similarity" refers to the percent similarity in base pair sequence (as determined by any suitable method) between two or more polynucleotide sequences. Two or more sequences can be anywhere from 0-100% similar, or any integer value therebetween. Identity or similarity can be determined by comparing a position in each sequence that may be aligned for purposes of comparison. When a position in the compared sequence is occupied by the same nucleotide base or amino acid, then the molecules are identical at that position. A degree of similarity or identity between polynucleotide sequences is a function of the number of identical, matching or corresponding nucleotides at positions shared by the polynucleotide sequences. A degree of identity of polypeptide sequences is a function of the number of identical amino acids at corresponding positions shared by the polypeptide sequences. A degree of homology or similarity of polypeptide sequences is a function of the number of amino acids at corresponding positions shared by the polypeptide sequences.

"Complementary" refers to the natural hydrogen bonding by base pairing between purines and pyrimidines. For example, the sequence A-C-G-T (5'->3') forms hydrogen bonds with its complements A-C-G-T (5'->3') or A-C-G-U (5'->3'). Two single-stranded molecules may be considered partially complementary, if only some of the nucleotides bond, or "completely complementary" if all of the nucleotides bond. The degree of complementarity between nucleic acid strands affects the efficiency and strength of hybridization and amplification reactions. "Fully complementary" refers to the case where bonding occurs between every base pair and its complement in a pair of sequences, and the two sequences have the same number of nucleotides.

The terns "paralog" and "ortholog" are defined below in the section entitled "Orthologs and Paralogs". In brief, orthologs and paralogs are evolutionarily related genes that have similar sequences and functions. Orthologs are structurally related genes in different species that are derived by a speciation event. Paralogs are structurally related genes within a single species that are derived by a duplication event. The term "equivalog" describes members of a set of homologous proteins that are conserved with respect to function since their last common ancestor. Related proteins are grouped into equivalog families, and otherwise into protein families with other hierarchically defined homology types. This definition is provided at the Institute for Genomic Research (TIGR) World Wide Web (www) website, "tigr.org" under the heading "Terms associated with TIGRFAMs".

In general, the term "variant" refers to molecules with some differences, generated synthetically or naturally, in their base or amino acid sequences as compared to a reference (native) polynucleotide or polypeptide, respectively. These differences include substitutions, insertions, deletions or any desired combinations of such changes in a native polynucleotide of amino acid sequence.

With regard to polynucleotide variants, differences between presently disclosed polynucleotides and polynucleotide variants are limited so that the nucleotide sequences of the former and the latter are closely similar overall and, in many regions, identical. Due to the degeneracy of the genetic code, differences between the former and latter nucleotide sequences may be silent (i.e., the amino acids encoded by the polynucleotide are the same, and the variant polynucleotide sequence encodes the same amino acid sequence as the presently disclosed polynucleotide. Variant nucleotide sequences may encode different amino acid sequences, in which case such nucleotide differences will result in amino acid substitutions, additions, deletions, insertions, truncations or fusions with respect to the similar disclosed polynucleotide sequences. These variations may result in polynucleotide variants encoding polypeptides that share at least one functional characteristic. The degeneracy of the genetic code also dictates that many different variant polynucleotides can encode identical and/or substantially similar polypeptides in addition to those sequences illustrated in the Sequence Listing.

Also within the scope of the invention is a variant of a gene promoter listed in the Sequence Listing, that is, one having a sequence that differs from one of the polynucleotide sequences in the Sequence Listing, or a complementary sequence.

The term "plant" includes whole plants, shoot vegetative organs/structures (for example, leaves, stems and tubers), roots, flowers and floral organs/structures (for example, bracts, sepals, petals, stamens, carpels, anthers and ovules), seed (including embryo, endosperm, and seed coat) and fruit (the mature ovary), plant tissue (for example, vascular tissue, ground tissue, and the like) and cells (for example, guard cells, egg cells, and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, horsetails, psilophytes, lycophytes, bryophytes, and multicellular algae (see for example, FIG. 1, adapted from Daly et al. (2001) supra, FIG. 2, adapted from Ku et al. (2000) supra; and see also Tudge (2000) in *The Variety of Life*, Oxford University Press, New York, N.Y. pp. 547-606.

A "control plant" as used in the present invention refers to a plant cell, seed, plant component, plant tissue, plant organ or whole plant used to compare against transgenic or genetically modified plant for the purpose of identifying an enhanced phenotype in the transgenic or genetically modified plant. A control plant may in some cases be a transgenic plant line that comprises an empty vector or marker gene, but does not contain the recombinant polynucleotide of the present invention that is expressed in the transgenic or genetically modified plant being evaluated. In general, a control plant is a plant of the same line or variety as the transgenic or genetically modified plant being tested. A suitable control plant would include a genetically unaltered or non-transgenic plant of the parental line used to generate a transgenic plant herein.

"Wild type" or "wild-type", as used herein, refers to a plant cell, seed, plant component, plant tissue, plant organ or whole plant that has not been genetically modified or treated in an experimental sense. Wild-type cells, seed, components, tissue, organs or whole plants may be used as controls to compare levels of expression and the extent and nature of trait modification with cells, tissue or plants of the same species in which expression of a defense response polypeptide is altered, e.g., in that it has been overexpressed or ectopically expressed.

A "transgenic plant" refers to a plant that contains genetic material not found in a wild-type plant of the same species, variety or cultivar. The genetic material may include a transgene, an insertional mutagenesis event (such as by transposon or T-DNA insertional mutagenesis), an activation tagging sequence, a mutated sequence, a homologous recombination event or a sequence modified by chimeraplasty. Typically, the foreign genetic material has been introduced into the plant by human manipulation, but any method can be used as one of skill in the art recognizes.

A transgenic plant may contain an expression vector or cassette. The expression cassette typically comprises a polypeptide-encoding sequence operably linked (i.e., under regulatory control of) to appropriate inducible or constitutive regulatory sequences that allow for the controlled expression of polypeptide. The expression cassette can be introduced into a plant by transformation or by breeding after transformation of a parent plant. A plant refers to a whole plant as well as to a plant part, such as seed, fruit, leaf, or root, plant tissue, plant cells or any other plant material, e.g., a plant explant, as well as to progeny thereof, and to in vitro systems that mimic biochemical or cellular components or processes in a cell.

A "trait" refers to a physiological, morphological, biochemical, or physical characteristic of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g. by measuring resistance to pathogens or tolerance to water deprivation or particular salt or sugar concentrations, or by the observation of the expression level of a gene or genes, e.g., by employing Northern analysis, RT-PCR, microarray gene expression assays, or reporter gene expression systems, or by agricultural observations such as extent of disease, hyperosmotic stress tolerance or yield. Any technique can be used to measure the amount of, comparative level of, or difference in any selected chemical compound or macromolecule in the transgenic plants, however.

"Trait modification" refers to a detectable difference in a characteristic in a plant ectopically expressing a polynucleotide or polypeptide of the present invention relative to a plant not doing so, such as a wild-type plant. In some cases, the trait modification can be evaluated quantitatively. For example, the trait modification can entail at least about a 2% increase or decrease, or an even greater difference, in an observed trait as compared with a control or wild-type plant. It is known that there can be a natural variation in the modified trait. Therefore, the trait modification observed entails a change of the normal distribution and magnitude of the trait in the plants as compared to control or wild-type plants.

The term "transcript profile" refers to the expression levels of a set of genes in a cell in a particular state, particularly by comparison with the expression levels of that same set of genes in a cell of the same type in a reference state. For example, the transcript profile of a particular defense response protein in a suspension cell is the expression levels of a set of genes in a cell knocking out or overexpressing that defense response protein compared with the expression levels of that same set of genes in a suspension cell that has normal levels of that defense response protein. The transcript profile can be presented as a list of those genes whose expression level is significantly different between the two treatments, and the difference ratios. Differences and similarities between expression levels may also be evaluated and calculated using statistical and clustering methods.

"Ectopic expression or altered expression" in reference to a polynucleotide indicates that the pattern of expression in, e.g., a transgenic plant or plant tissue, is different from the expression pattern in a wild-type plant or a reference plant of the same species. The pattern of expression may also be compared with a reference expression pattern in a wild-type plant of the same species. For example, the polynucleotide or polypeptide is expressed in a cell or tissue type other than a cell or tissue type in which the sequence is expressed in the wild-type plant, or by expression at a time other than at the time the sequence is expressed in the wild-type plant, or by a response to different inducible agents, such as hormones or environmental signals, or at different expression levels (either higher or lower) compared with those found in a wild-type plant. The term also refers to altered expression patterns that are produced by lowering the levels of expression to below the detection level or completely abolishing expression. The resulting expression pattern can be transient or stable, constitutive or inducible. In reference to a polypeptide, the term "ectopic expression or altered expression" further may relate to altered activity levels resulting from the interactions of the polypeptides with exogenous or endogenous modulators or from interactions with factors or as a result of the chemical modification of the polypeptides.

The term "overexpression" as used herein refers to a greater expression level of a gene in a plant, plant cell or plant tissue, compared to expression in a wild-type plant, cell or tissue, at any developmental or temporal stage for the gene. Overexpression can occur when, for example, the genes encoding one or more defense response proteins are under the control of a strong promoter (e.g., the cauliflower mosaic virus 35S transcription initiation region). Overexpression may also under the control of an inducible promoter such as a disease-inducible promoter. Thus, overexpression may occur throughout a plant or in the presence of particular environmental signals, depending on the promoter used. Overexpression may take place in plant cells normally lacking expression of polypeptides functionally equivalent or identical to the present defense response proteins. Overexpression may also occur in plant cells where endogenous expression of the present defense response proteins or functionally equivalent molecules normally occurs, but such normal expression is at a lower level. Overexpression thus results in a greater than normal production, or "overproduction" of the defense response protein in the plant, cell or tissue.

DESCRIPTION OF THE SPECIFIC EMBODIMENTS

We have shown that overexpression of transcription factors can lead to enhanced disease resistance in *Arabidopsis* plants. However, overexpression of these defense proteins generally comes at a price; the overexpressing plant is often small and may have other undesirable developmental effects such as delayed development, low yield or fertility. This raises an obvious question: can regulation of transcription factor pathways be controlled in a manner that confers disease resistance and yet avoids much or all of the growth and developmental penalty? Overexpression and associated disease resistance without significant adverse morphological effects would make these transcription factors effective commercial tools for disease resistance. Use of disease-inducible promoters mya provide disease resistance while mitigating the undesirable effects of constitutive overexpression of transcription factors responsible for that resistance.

The development of effective disease resistance in these plants is likely to require a promoter(s) that responds rapidly to disease pressure, as well as sustained expression throughout disease progression to maximize effectiveness. The selection strategy for identifying commercially valuable disease-inducible promoters thus considered the following criteria. Promoters of interest would be:

expressed at a low basal level (that is, in the absence of plant disease);

induced strongly and at a sustained induction level early in the course of a plant disease;

specific to the defense response (the ability to be induced by other environmental factors increases frequency of expression and the likelihood that the plant would have reduced size or yield); and ideally induced by multiple pathogens and/or elicitors (providing a common early response to pathogen detection).

Transcript profiling (TxP) is a powerful tool for promoter discovery, providing a global insight in genes expression, regulation and induction levels in host-pathogen interaction. As outlined below, disease-inducible promoters have been identified in microarrays by transcript profiling of plants exposed to pathogen-related challenges. When a transcription factor sequence that is known to confer disease resistance but which also causes significant adverse morphological consequences was overexpressed under the regulatory control of disease-inducible promoters, the result was the production of disease resistant plants of normal (i.e., wild type) or near-normal stature and development.

Promoters showing early induction in a compatible pathogenic interaction and little or no background expression could be used to drive expression of transcription factors to provide enhanced disease resistance with little adverse affect on yield ("yield drag"). Promoters of genes that are induced relatively late in compatible interactions, such as the classic pathogenesis-related (PR) genes, are less likely to be effective, since they reflect a late induction of defense responses that is ineffective at stopping pathogen growth. Therefore, we concentrated on very early time points in fungal interactions and early events following recognition of pathogen-derived elicitors.

A number of microarray data sets were mined to define candidate promoters, providing insight in multiple host-pathogen interactions as well as in plant innate immunity. Plant pathogens fall into two major classes: biotrophs and necrotrophs (reviewed in Oliver and Ipcho (2004) *Mol. Plant. Pathol.* 5: 347-352). Biotrophic pathogens obtain energy by parasitizing living plant tissue, while necrotrophs obtain energy from dead plant tissue. Examples of biotrophs include the powdery mildews, rusts, and downy mildews; these pathogens can only grow in association with living plant tissue, and parasitize plants through extracellular feeding structures called haustoria. Examples of necrotrophs include *Sclerotinia sclerotiorum* (white mold), *Botrytis cinerea* (grey mold), and *Cochliobolus heterostrophus* (Southern corn leaf blight). The general pathogenic strategy of necrotrophs is to kill plant tissue through toxins and lytic enzymes, and live off the released nutrients. Pathologists also recognize a third class of pathogens, called hemibiotrophs: these pathogens have an initial biotrophic stage, followed by a necrotrophic stage once a parasitic association with plant cells has been established. In general, different defense responses have been found to be induced in plants in response to attack by a biotrophic or necrotrophic pathogen. Infection by biotrophic pathogens often induces defense responses mediated by the plant hormone salicylic acid, while attack by a necrotrophic pathogen often induces defense responses mediated by coordinated action of the hormones ethylene and jasmonate. To identify promoters with the broadest specificity, we included expression profiles from plant treatments with both biotrophs and necrotrophs. The plant treatments included:

1. *Sclerotinia sclerotiorum* is a necrotrophic fungus that causes important diseases known as white mold, *Sclerotinia* wilt or stalk rot, or *Sclerotinia* head rot on a wide variety of broadleaf crops. This pathogen is known to infect about 408 species of plants, including the model plant species *Arabidopsis*.
2. *Botrytis cinerea* or gray mold is a necrotrophic fungus that infects a wide array of herbaceous annual and perennial plants. *Botrytis* infections are favored by cool, rainy spring and summer weather.
3. Oligogalacturonides (OGs), homopolymers of alpha-1, 4-linked D-galacturonic acid, are released from the plant cell wall upon insect feeding, wounding, or the action of cell wall-degrading enzymes secreted by some necrotrophic fungal and bacterial pathogens (Doares et al. (1995) *Proc. Natl. Acad. Sci. U.S.A.* 92: 4095-4098; Bergey et al. (1996) *Proc. Natl. Acad. Sci. U.S.A.* 93: 12053-12058). They are well-characterized elicitors of the inducible defense response.
4. *Erysiphe* species are biotrophic fungal plant pathogens that cause powdery mildew on a wide range of host plants. They are obligate pathogens that cannot survive in the absence of living host tissue, in contrast to *Botrytis* and *Sclerotinia*, which attack plants by killing tissue and living off released nutrients (necrotrophy). *Erysiphe orontii* is one of several powdery mildew species that infect *Arabidopsis*.

Global microarray analysis of multiple pathogenic interactions allowed the identification of a large number of disease-inducible genes, however, only a subset were found to be of particular interest for the development of disease resistance in crops or other commercially valuable species. Analysis of gene expression data after *Sclerotinia*, *Botrytis*, and OG-treatment, allowed the identification of candidate promoters with desirable expression characteristics. Subsequent analysis of gene expression data from an *Arabidopsis-Erysiphe orontii* interaction resulted in the identification of several additional promoters. Thus, the current invention is a set of *Arabidopsis* promoters responsive to multiple pathogens and to elicitors (oligogalacturonides), and a method for their potential use for the engineering of disease tolerance in crops. As shown in Table 6, thirty-nine of these promoters have thus far been examined in detail.

EXAMPLES

Example I

Time Courses for Microarray Experiments

Microarray analysis of multiple pathogenic interactions allowed the identification of a large number of disease-inducible genes. Baseline time courses in *Arabidopsis* were produced for treatment with salicylic acid, methyl jasmonate, and 1-aminocyclopropane-1-carboxylic acid (ACC), for infection with *Sclerotinia*, *Botrytis* and *Erysiphe*, and for treatment with oligogalacturonides elicitors. Additional time course microarrays were used to better defined the behavior of the lead candidate promoters in abiotic stress conditions, such as water deprivation in soil grown *Arabidopsis* plants, cold treatment of *Arabidopsis* seedlings, NaCl treatment of *Arabidopsis* seedlings, and mannitol treatment of *Arabidopsis* seedlings. In these baseline studies, we focused on early and medium-term responses, via samples collected over a time-course following the treatments. Specific methodology for these experiments is described below.

*Sclerotinia* and *Botrytis* infection were carried out on plates. An appropriate growth protocol was developed by adapting standard plate disease assay conditions, with emphasis on retaining conditions that allowed resistant transgenic lines to be distinguished from sensitive non-transgenic lines. Appropriate time points for analysis were determined by 1) monitoring development of disease symptoms and 2) induction of reporter genes. Wild-type seedlings were grown on plates containing 50% MS, 0.05% MES, 1% sucrose medium with 44 seeds/plate, under 24 h light. After 10 days, seedlings were transplanted to 25 mm deep plates with the same medium minus sucrose for pathogen treatment. Seedlings were inoculated with *Sclerotinia* or *Botrytis* or mock-inoculated with water on day 14. Inoculum was prepared as follows. Both pathogens were maintained on Potato Dextrose Agar plates transferred weekly. Three days before seedling inoculation, a *Sclerotinia* hyphal plug from a two-week old plate was used to inoculate a bottle of half-strength Potato Dextrose Broth. This culture was allowed to grow at room temperature until the day of seedling inoculation. The hyphal ball was rescued from the medium, weighed, and ground in a blender with water (50 ml/gm tissue). After grinding, the mycelial suspension was filtered through two layers of cheesecloth and the resulting suspension was diluted 1:5 in water. The *Botrytis* inoculum was prepared by making a spore suspension ($10^6$ spores/ml) in water from two-week old plates on the day of seedling inoculation. Plants were inoculated by spraying to run-off with the *Sclerotinia* mycelial suspension, *Botrytis* spore suspension, or water, using a Preval aerosol sprayer. After inoculation, plates were returned to the growth chamber and the lights were set to 12 h dark/12 h light, immediate darkness. Tissues were harvested at 1, 4, 8, and 48 hours after inoculation. Separate root and shoot tissues were collected, and replicate pooled shoot samples from each treatment time were hybridized to microarrays.

The hormone treatments were performed at the seedling stage on plates, and experiments were performed on separately harvested root and shoot samples. For all hormone treatments, wild-type seedlings were grown on plates, 37 seeds/plate, under 24 h light. After 7-8 days, seedlings were transplanted to vertically-oriented square plates, and treatments begun on the 13th day. Plants were treated in the morning with either SA (400 µM), ACC (100 µM), MeJA (100 µM) or ABA (100 µM); control plants were given a mock treatment appropriate for the experimental treatment. Treatments were applied by lying each plate flat on a lab bench, then pouring on treatment solution until all seedling tissue was submerged. The solution remained on the plates for 5 minutes, then was removed, and plates were returned (in vertical orientation) to the growth chamber. All treatments were applied in parallel. Tissues were harvested throughout the day. For the SA, ACC, and MeJA time courses, samples were selected for analysis at 0.5, 4, 8 and 24 hours post-treatment. For the ABA treatment, tissues were harvested at 1, 4, and 8 and 24 hours. Separate root and shoot tissues were collected, and replicate samples from each treatment and time were hybridized to microarrays.

For soil-based water deprivation experiments, wild-type Col-0 plants were grown singly in plastic pots in 10 h light. At 8 weeks a drought treatment was begun by randomly relocating all pots in the morning onto four-rack long shelves covered in absorbent paper. On each shelf, multiple plants were maintained as well-watered controls by isolating the pot in a weighboat. After 3 days of dry-down, potential random harvest locations were chosen on each subsequent day, excluding borders. Random selection was done over multiple strata determined by relative location in the growth room. For each harvest selection, plants that were showing the predominant drought phenotype of that day were actually harvested. Replicate samples were harvested for microarrays and physiological measurements. Based on a cluster analysis of the physiological measurements, samples were classified into three levels of drought stress (mild, moderate and severe) and two rehydration states, 2 hr and 23 hr post-rehydration. Replicate samples, pooled from plants that clustered the most closely from each group, were hybridized to microarrays.

Other abiotic stress treatments (NaCl, cold, and mannitol) were carried out on plates. Wild-type seedlings were grown on round plates, 37 seeds/plate, under 24 h light. After 7-8 days, seedlings were transplanted to vertically-oriented square plates, and treatments begun on the 13th day. Plants were treated in the morning with either NaCl (200 mM), mannitol (400 mM), or cold (4° C.) water; control plants were given a mock treatment. All treatments were applied in parallel, by submerging the seedlings up to the root-shoot boundary for the duration of the experiment. This was accomplished by placing the plates upright in the lid of a pipette tip box filled with treatment solution. After roots were submerged, the boxes containing the plates were returned to the growth chamber. Samples were then taken throughout the day. Tissues were harvested at 0.5, 1, 4, and 8 hours. Separate root and shoot samples were collected and replicate pooled samples from each treatment time were hybridized to microarrays. A total of 64 microarrays were used, 8 per treatment set for each tissue.

Data for oligogalacturonide and *Erysiphe orontii* treatments was obtained from experiments done for the *Arabidopsis* 2010 program (http://ausubellab.mgh.harvard.edu/imds/). For oligogalacturonide treatments, *Arabidopsis* seedlings were grown for ten days in liquid medium, then treated with 200 µg/ml OG. The seedlings were harvested at 1 h and 6 h post treatment. Assays were run in triplicate, about 15 seedlings per experiment were harvested. For *Erysiphe orontii* treatment, 4-week old Col wild-type plants were infected with conidia from 10-day old *E. orontii* cultures. Leaves were harvested at 6, 12, 18, 24, 48, 72, 96, and 120 hours post-inoculation. Inoculations were done at different times of day so that all harvesting could be done at the same time of day, in the middle of the 12-hour light cycle. To limit effects of age, only leaves number 7 to 10 were harvested. Replicates are derived from three independent biological experiments, with no overlap in growing periods.

Example II

Definition of Criteria for Promoter Selection

Desired induction pattern: We hypothesized that promoters showing strong, early, and relatively sustained induction levels throughout disease progression would be good candidates for use in driving transcription factor expression.

A complication in defining criteria was the lack of spatial expression data in compatible interactions with *Sclerotinia* and *Botrytis*. The datasets used were limited to average expression at the whole seedling or rosette level, and did not distinguish between local and systemic responses. Spatial localization of gene induction may further vary during disease progression as the plant responds to pathogen ingress. A strong but highly localized response to the pathogen may translate into a relatively weak fold induction in mRNA prepared from whole seedlings, which would be indistinguishable from weak systemic induction. Because of this limitation, we chose weakly restrictive selection criteria in regards to promoter strength (as seen at the whole seedling level).

Based on these considerations, we defined the selection criteria as follows: genes with greater than 2-fold induction at the early (1 hr) and late (48 hr) time points in the interaction with either *Sclerotinia* or *Botrytis*. A total of 3418 non-redundant genes (3653 MRT) were significantly induced in at least one time point following *Sclerotinia*, *Botrytis* or OG treatments (BH corrected p-value <0.05). Of those, less than 10% (n=302) meet the selection criteria outlined above. Throughout the document, we refer to genes selected as having a "sustained" expression profile. We used OG-treatment transcript profiling (TxP) to complement, and often support, selection of candidate genes from pathogen TxP.

Basal Expression Level: Basal expression levels of candidate promoters were evaluated in mock treatments used for the baseline *Sclerotinia* and *Botrytis* TxP data. After normalization, relative signal intensity across all experiments ranged from 0.05, the lower limit of detection, to a maximum relative intensity of 35. To define a range of acceptable baseline intensity level for candidate disease-inducible promoters, the expression of a number of known tissue-specific and disease-inducible promoters in untreated seedlings was examined. These data appear in Table 1. As a whole, the relative intensity values observed were in agreement with the expected expression level reported from the literature. A relative signal intensity of less than 1 was defined as acceptable basal expression level for candidate disease-inducible promoters. A limited number (n=39; 13%) of the 302 candidate genes had a basal intensity value greater than 1. In Table 1, the values for "Average Intensity" were determined from the Average Signal Intensity in mock treatments (1-48 hr)*.

gen treatment (n=302), 10% (n=30) showed significant induction or repression following either or both abiotic treatments. Two promoters AT1G35230 (SEQ ID NO: 22) and AT5G48540 (SEQ ID NO: 28) showed moderate induction in cold or NaCl treatment. Promoters AT1G35230 (construct P26467, SEQ ID NO: 59), or AT5G48540 (construct P26461, SEQ ID NO: 65), were cloned into *Arabidopsis* plants and evaluated for disease resistance. Table 2 illustrates the regulation of the disease-inducible gene set in abiotic stress treatments. A relatively large number of disease-inducible genes

TABLE 1

Basal TxP Signal Intensity of Known Developmentally- or Disease-Regulated Genes

| Sequence Name | Gene | Expression Profile | Average Intensity* | Reference |
|---|---|---|---|---|
| AT1G68530 | CUT1 | epidermal specific | 7.71 | Kunst et al. (2000) *Biochem. Soc. Trans.* 28: 651-654 |
| G133 | AP3 | flower specific | 0.09 | Jack et al. (1992) *Cell* 68: 683-697 |
| G1540 | WUS | flower specific | 0.13 | Schoof et al. (2000) *Cell* 100: 635-644 |
| G549 | LFY | meristem specific | 0.11 | Weigel et al. (1992) *Cell* 69: 843-859 |
| AT2G26290 | ARSK1 | root specific | 0.09 | Hwang and Goodman (1995) *Plant J.* 8: 37-43 |
| AT4G19680 | IRT2 | root specific | 0.09 | Vert et al. (2001) *Plant J.* 26, 181-189 |
| AT5G40420 | OLE | seed specific | 0.11 | Zou et al. (1996) *Plant Mol. Biol.* 31: 429-433 |
| AT2G14610 | PR-1 | disease, low basal | 0.20 | Ward et al. (1991) *Plant Cell* 3: 1085-1094 |
| AT3G57260 | BGL2 | disease, low basal | 0.26 | Ward et al. (1991) supra |
| AT1G75040 | PR5 | disease, low basal | 0.50 | Ward et al. (1991) supra |
| AT2G02120 | PDF2.1 | disease, low basal | 0.18 | Ward et al. (1991) supra |
| G1266 | ERF1 | disease, low basal | 0.08 | Solano et al. (1998) *Genes Dev.* 12: 3703-3714 |
| AT1G66160 | ATCMPG1 | disease, low basal | 0.55 | Heise et al. (2002) *Proc. Natl. Acad. Sci. U.S.A.* 99: 9049-9054 |
| AT3G26830 | PAD3 | disease, low basal | 0.41 | Zhou et al. (1999) *Plant Cell* 11: 2419-2428 |
| AT1G18250 | ATLP-1 | disease, low basal | 0.43 | Hu and Reddy (1997) *Plant Mol. Biol.* 34: 949-959 |
| AT2G03760 | RAR047 | disease, low basal | 0.71 | Lacomme and Roby (1996) *Plant Mol. Biol.* 30: 995-1008 |
| AT5G06860 | PGIP1 | disease, moderate basal | 3.78 | Ferrari et al. (2003) *Plant Cell* 15: 93-106 |
| AT3G45640 | ATMPK3 | disease, moderate basal | 4.29 | Asai et al. (2002) *Nature* 415: 977-983 |
| AT2G47730 | GST6 | disease, high basal | 10.01 | Chen and Singh (1999) *Plant J.* 19: 667-677 |
| AT5G24780 | VSP1 | wounding, low basal | 0.27 | Utsugi et al. (1998) *Plant Mol. Biol.* 38: 565-576 |
| AT5G24770 | VSP2 | wounding, low basal | 0.82 | Utsugi et al. (1998) supra |
| AT2G24850 | TAT3 | wounding, low basal | 0.44 | Titarenko et al. (1997) *Plant Physiol.* 115: 817-826 |
| G1792 | G1792 | disease, low basal | 0.16 | |
| G28 | G28/ATERF-1 | disease, low basal | 1.01 | |

Identification of Genes Induced by Multiple Pathogens: Genes induced in multiple pathogenic interactions are likely components of convergent signaling pathways in compatible, incompatible, or non-host interactions. In selecting candidate disease-inducible promoters, we first prioritized genes with sustained expression in both *Sclerotinia* and *Botrytis* interactions. We complemented this gene set with genes showing sustained induction in one pathogenic interaction but changing significantly (BH-corrected value<0.05 at any time point) in either remaining treatment. Using a consolidated gene list of 302 non-redundant genes with sustained induction in either of the pathogenic interactions, we compared expression profiles across treatments. A Venn diagram (FIG. 3) provides an alternative view of the relationships of genes with sustained expression level across treatments.

Inducibility by abiotic stresses: We prioritized promoters specific to pathogenic interactions. Any genes showing greater than 4-fold induction in cold or NaCl treatment were considered carefully, but in large part they were excluded. Of all the genes with sustained expression in at least one pathoshowed strong and significant induction after mannitol treatment. This bias is particularly obvious for genes selected for sustained expression in pathogenic interactions. The current literature supports the model that mannitol may be perceived by plants as a fungal elicitor, although this hypothesis has not been demonstrated experimentally (Jennings (1984) *Adv. Microbiol. Physiol.* 25: 149-193; Joosten et al. (1990) *Neth. J. Plant Pathol.* 96: 103-112; Smirnoff and Cumbes (1989) *Phytochem.* 28: 1057-1060. For this reason, we did not consider mannitol treatment when evaluating abiotic stress responsiveness of the candidate promoter set. Finally, we noted a close relationship between pathogen-induced genes and soil drought treatment. Nearly 85% of the genes with sustained expression in either *Sclerotinia* or *Botrytis* interactions were significantly regulated in soil drought treatment. Crosstalk between disease, hormone, and drought-related signaling pathways has been reported, consistent with the current data. We selected candidate promoters from the three groups: neutral in soil drought, positively regulated by drought, and negatively regulated by drought.

TABLE 2

Regulation of disease-inducible genes by abiotic stresses.

|  | Drought | Cold | NaCl | Mannitol |
|---|---|---|---|---|
| Disease-Inducible Genes Significantly Induced (n = 3418) | 68% | 12% | 5% | 20% |
| Disease-Inducible Genes with Sustained Expression (n = 302) | 84% | 20% | 7% | 42% |

Relationship to hormone treatment: Regulation by hormones was examined to assess and retain diversity in our selection of candidate promoters. Within our focused group of genes with sustained expression (n=302), 174 (57%) were induced by SA-treatment, 31 (10%) by MeJA, and three (1%) by ACC (ethylene). When possible, we included representatives of all groups.

Cis-element analysis: Cis-element analysis provided additional criteria for promoter selection. We concluded from a general analysis using *Sclerotinia, Botrytis*, and OG-inducible gene sets clustered for equivalent expression profiles that genes harboring a W-box are generally early-responsive, while genes with the GCC-, S- or G-box are late-responsive. We analyzed each candidate promoter for the presence of particular these cis-elements. In general, we preferentially weighted the selection of promoters harboring multiple W-boxes when facing a choice between genes with otherwise equivalent expression characteristics, and we also attempted to choose promoters with diverse cis element combinations for testing.

Example III

Candidate Promoters

Analysis of disease-related microarrays, as described in the summary section, allowed the identification of candidate promoters with desirable expression characteristics. These promoters are listed in the Sequence Listing, which also includes fold induction in interactions with *Sclerotinia, Botrytis*, and OG-treatment. These promoters and the extent to which they were induced at various time points after the *Sclerotinia, Botrytis*, and OG-treatments are shown in Table 3.

TABLE 3

Candidate promoter list generated from analysis of disease-related microarrays

| | | Fold increase (hours post inoculation) | | | | | | | | |
|---|---|---|---|---|---|---|---|---|---|---|
| | | *Sclerotinia* Fold Induction | | | | *Botrytis* Fold Induction | | | OGs Fold Induction | |
| AGI (SEQ ID NO:) | Description | 1 | 4 | 8 | 48 | 1 | 4 | 48 | 1 | 6 |
| AT1G16420 (1) | Hypothetical protein common family; similar to latex-abundant protein (GI:4235430)(*Hevea brasiliensis*) | 19 | 2.5 | 1.3 | 1.5 | 14 | 4.5 | 4.7 | 6.4 | −1 |
| AT1G26380 (2) | FAD-linked oxidoreductase family, similar to SP|P30986 reticuline oxidase precursor (Berberine-bridge-forming enzyme) (BBE) (Tetrahydroprotoberberine synthase) (*Eschscholzia californica*) | 19.2 | 5.6 | 2 | 4 | 13 | 6.2 | 13.6 | 100 | 1.6 |
| AT1G26420 (3) | FAD-linked oxidoreductase family, similar to SP|P30986 reticuline oxidase precursor (Berberine-bridge-forming enzyme) (BBE) (Tetrahydroprotoberberine synthase) (*Eschscholzia californica*) | 3.4 | 4.7 | 2.8 | 4.1 | 3.4 | 3.3 | 14.1 | 43.5 | 1.2 |
| AT1G28190 (4) | Expressed protein | 7.7 | 3.6 | 2.7 | 2.2 | 5.1 | 4.5 | 6.3 | 20 | −1 |
| AT1G56060 (5) | Hypothetical protein | 34.6 | 3.2 | 1.7 | 3.2 | 20 | 5.4 | 8.5 | 32.4 | −2 |
| AT1G61560 (6) | [MLO6] *Arabidopsis thaliana* membrane protein Mlo6 mRNA, complete cds; seven transmembrane MLO protein family (MLO6) | 5.8 | 3.2 | 1.4 | 1.9 | 3.8 | 3.3 | 4.8 | 9.9 | −1 |
| AT2G32210 (9) | Expressed protein | 3.6 | 2.7 | 1.7 | 2.1 | 3.3 | 3.4 | 4.5 | n/d | n/d |
| AT2G35980 (11) | [YLS9] *Arabidopsis thaliana* YLS9 mRNA for hin1 homolog, complete cds; harpin-induced protein 1 family (HIN1) | 4.6 | 12 | 3.1 | 5.2 | 2.8 | 6.5 | 37.8 | 40.7 | 1.4 |
| AT3G18250 (12) | Hypothetical protein | 2.1 | 2.3 | 5.4 | 2.5 | 1.6 | 2.8 | 10.1 | 7.2 | −2 |
| AT3G63380 (13) | Calcium-transporting ATPase (calcium pump), putative, similar to SP|Q9LF79 Calcium-transporting ATPase | 12.5 | 3 | 4.6 | 2.7 | 5.8 | 1.9 | 6.3 | 16.6 | 1.7 |

TABLE 3-continued

Candidate promoter list generated from analysis of disease-related microarrays

| AGI (SEQ ID NO:) | Description | Sclerotinia Fold Induction | | | | Botrytis Fold Induction | | | OGs Fold Induction | |
|---|---|---|---|---|---|---|---|---|---|---|
| | | 1 | 4 | 8 | 48 | 1 | 4 | 48 | 1 | 6 |
| | 8, plasma membrane-type (EC 3.6.3.8) (Ca2+-ATPase, isoform 8) {*Arabidopsis thaliana*} | | | | | | | | | |
| AT4G01010 (14) | [ATCNGC13] Member of Cyclic nucleotide gated channel family; cyclic nucleotide-regulated ion channel, putative (CNGC13), similar to CaM-regulated potassium ion channel (ACBK1) GI:8515883 from (*Arabidopsis thaliana*) | 7.3 | 2 | 1.1 | 2.1 | 6 | 2.2 | 5 | 5.5 | −1 |
| AT4G21390 (15) | Serine/threonine kinase - like protein, serine/threonine kinase BRLK, *Brassica oleracea*, gb:Y12531 | 11.8 | 3.7 | 1.3 | 2.1 | 7.3 | 4.9 | 6.3 | 6.2 | −1 |
| AT4G35110 (16) | Expressed protein, pEARLI 4, *Arabidopsis thaliana*, PATCHX:G871782 | 5.7 | 1.9 | 1.7 | 2.3 | 4.6 | 1.4 | 7.2 | 19 | 1.6 |
| AT5G22530 (17) | Expressed protein | 5.5 | 1.3 | 1.3 | 1.7 | 4.7 | 2.2 | 6 | 4.1 | −2 |
| AT5G64905 (18) | Expressed protein | 7.5 | 2.7 | 1.7 | 2.1 | 4.2 | 4 | 13.7 | 31.5 | −2 |
| AT1G02360 (19) | Glycosyl hydrolase family 19 (chitinase), similar to chitinase precursor GI:5880845 from (*Petroselinum crispum*) | 19.3 | 4.2 | 5.7 | 1.5 | 15 | 4.8 | 9 | 27.5 | 3.6 |
| AT1G24140 (20) | Metallo proteinase -related, similar to GB:AAB61099 | 11.3 | 3.9 | 1.6 | 2.4 | 7.3 | 5.5 | 9.6 | 3.6 | −2 |
| AT1G24145 (21) | Expressed protein | 9 | 3.7 | 1.9 | 3.7 | 7.1 | 5.7 | 16.6 | n/d | n/d |
| AT1G35230 (22) | [AGP5] Arabinogalactan-protein (AGP5) mRNA, complete cds; arabinogalactan-protein (AGP5), identical to gi_3883128_gb_AAC77827 | 9.2 | 7.4 | 6.3 | 5.2 | 7 | 7.3 | 15.3 | 16.9 | −3 |
| AT1G57630 (23) | Disease resistance protein (TIR class), putative, domain signature TIR exists, suggestive of a disease resistance protein | 25.5 | 4.2 | 4.3 | 4.1 | 15 | 3.7 | 19.9 | 65.3 | −2 |
| AT1G67810 (24) | Hypothetical protein | 14.9 | 4.7 | 2.8 | 3.1 | 9.8 | 3.7 | 8.1 | 19.4 | 3.3 |
| AT4G18250 (25) | Receptor serine/threonine kinase-related protein, receptor serine/threonine kinase PR5K, PATCHX:G1235680 | 11.6 | 2 | 1.5 | 3.1 | 8.1 | 2.1 | 9.7 | 3.7 | 1.1 |
| AT4G35180 (26) | Amino acid transporter family, similar to amino acid permease 1 GI:976402 from (*Nicotiana sylvestris*); Transmembrane amino acid transporter protein | 7.3 | 1.8 | 2.5 | 2.6 | 5.7 | 2.4 | 12.9 | 16.3 | 1 |
| AT5G18470 (27) | Expressed protein, S-receptor kinase PK3 precursor, maize, PIR:T02753 | 4.5 | 2.5 | 1.5 | 3.6 | 4.4 | 2.5 | 11.5 | 4.5 | −1 |
| AT5G48540 (28) | Secretory protein-related (33 kDa); domain of unknown function | 6.2 | 2.7 | 1.7 | 3 | 5.2 | 2.8 | 7.5 | 4.5 | −1 |
| AT1G30700 (29) | FAD-linked oxidoreductase family, similar to SP\|P30986 reticuline oxidase precursor (Berberine-bridge-forming enzyme) (BBE) (Tetrahydroprotoberberine synthase) (*Eschscholzia californica*) | 3.4 | 1.4 | 5 | 1.1 | 4.1 | 1.6 | 13.3 | 59.3 | 2.6 |

TABLE 3-continued

Candidate promoter list generated from analysis of disease-related microarrays

| AGI (SEQ ID NO:) | Description | Sclerotinia Fold Induction | | | | Botrytis Fold Induction | | | OGs Fold Induction | |
|---|---|---|---|---|---|---|---|---|---|---|
| | | 1 | 4 | 8 | 48 | 1 | 4 | 48 | 1 | 6 |
| AT2G29460 (30) | [GST22] Chromosome II glutathione S-transferase (GST22) mRNA,; glutathione transferase, putative | 3.5 | 4.3 | 7.3 | 3.6 | 4.8 | 2.1 | 10.5 | 16.2 | 3.7 |
| AT2G43620 (31) | Glycosyl Hydrolase family 19 (chitinase), similar to basic endochitinase CHB4 precursor SP:Q06209 from (*Brassica napus*) | 4 | 4.1 | 3.3 | 7.4 | 2.9 | 2 | 8.7 | 3.9 | 1.1 |
| AT3G02840 (32) | Expressed protein | 16.7 | 2.3 | 1.2 | 1.2 | 6.6 | 2.7 | 4.4 | 22.2 | −1 |
| AT3G26830 (33) | [CYP71B15/PAD3] Putative camalexin biosynthesis gene; [PAD3] Mutations in pad3 are defective in biosynthesis of the indole derived phytoalexin camalexin. Encodes a putative cytochrome P450 monooxygenase | 2.3 | 3.5 | 3.7 | 5 | 2.3 | 1.5 | 19.7 | 18.5 | −1 |
| AT5G12930 (34) | Expressed protein, predicted proteins | 13 | 8.4 | 2.3 | 1.7 | 9.1 | 4.5 | 6.6 | 43.7 | −1 |
| AT5G24110 (35) | WRKY family transcription factor; [WRKY30] member of WRKY Transcription Factor; Group III | 9.4 | 3.7 | 1 | 1.6 | 3.8 | 2.6 | 4.9 | 70.9 | −1 | n/d = not done

Additional promoters selected from *Erysiphe* time series microarray experiments and soil drought treatments. Public microarrays comprising a time series of a compatible interaction between *Arabidopsis* and the obligate biotrophic fungal pathogen *Erysiphe orontii* were analyzed to complement our current selection. We relied essentially on the same selection criteria that we previously defined in pathogenic interaction with *Sclerotinia* and *Botrytis*. The selection criteria are summarized below:

a) Genes with early induction profile: Disease-inducible promoters in interaction with *Erysiphe* were identified from a time series microarrays from samples collected at 6, 12, 18, 24, 48, 72, 96 and 120 hrs post-inoculation. The selection requirement for this analysis was based on BH corrected p-value and significance defined at a p-value less than 0.05. 1683 genes were found to be significantly induced following treatment with *Erysiphe*, but fewer than 3% (n=45) are induced early. Early expression was defined by a change in expression level within a period of 72 hrs following inoculation with *Erysiphe*.

b) Genes with low basal expression: Low basal expression level is important to minimize potential pleiotropic phenotypes associated with the development of disease resistance trait in crops. Basal expression level was evaluated in mock treatments. For any given gene, relative signal intensity after normalization ranges between 0.05, our limit of detection, to a maximum intensity of 35. A relative signal intensity of less than 1 was defined as acceptable basal expression level for candidate disease-inducible promoters. Of the 45 candidate promoters defined above, 11 were retained for further evaluation.

c) Genes induced by multiple pathogens: Genes induced in multiple pathogenic interactions are likely components of convergent signaling pathways in compatible, incompatible, or non-host interactions. In selecting candidate disease-inducible promoters, we prioritized genes (n=7; one of which previously selected) that were also induced in interactions with either *Sclerotinia* or *Botrytis*. The six identified promoters and the extent to which they were induced at various time points after *Erysiphe, Sclerotinia, Botrytis*, and OG-treatments are shown in Table 4.

In addition, we hypothesized that promoters with both strong drought and pathogen induction might be useful for expression of G1792 and related genes. Therefore, we compared our sets of candidate pathogen-inducible promoters with a set of drought-inducible promoters from microarray data derived from soil drought experiments. Despite the fact that many of our pathogen-inducible promoter candidates showed some drought induction, this induction was relatively mild, and there was no overlap with the candidate drought promoter list. Therefore, it was necessary to relax the selection criteria for both pathogen and drought induction. Comparison of expanded lists of drought-inducible and disease-inducible candidates identified two that were induced by both drought and pathogen infection (AT5G24090, SEQ ID NO: 7, and AT5G62150, SEQ ID NO: 8). These two promoters are included in Table 4.

TABLE 4

Promoter induction at various time points after Erysiphe, Sclerotinia, Botrytis, and OG-treatments

| | | Fold increase (days post inoculation) | | | | | | | | Fold increase (hours post inoculation) | | | | | | | | |
|---|---|---|---|---|---|---|---|---|---|---|---|---|---|---|---|---|---|---|
| | | Erysiphe | | | | | | | | Sclerotinia | | | | Botrytis | | | OG | |
| AGI | Description | 0.25 | 0.5 | 0.75 | 1 | 2 | 3 | 4 | 5 | 1 | 4 | 8 | 48 | 1 | 4 | 48 | 1 | 6 |
| AT3G23550 (97) | MATE efflux protein family | 6.9 | — | — | — | — | 4.2 | 5.2 | 4.3 | 2.0 | 2.0 | 2.5 | — | 2.0 | — | 6.3 | 19.5 | — |
| AT2G18690 (36) | expressed protein | 2.3 | — | — | — | — | 4.4 | 4.9 | 14.1 | 5.0 | 3.2 | 2.0 | 4.0 | 4.0 | 3.2 | 10.0 | 8.4 | — |
| AT3G22060 (37) | receptor protein kinase-related | 2.3 | — | — | — | — | 2.3 | — | — | 2.5 | — | — | 3.2 | 2.0 | — | 6.3 | 3.5 | — |
| AT3G57240 (38) | [BG3] encodes a glycosyl hydrolase | — | — | — | 2.4 | 2.5 | 4.6 | 7.2 | 8.7 | — | — | — | — | — | — | 7.9 | — | — |
| AT2G18660 (39) | expressed protein | — | — | — | — | 4.7 | 16.6 | 21.0 | 33.0 | — | — | — | — | — | — | 12.6 | — | — |
| AT4G11890 (98) | [AT4G11890.2] protein kinase family | — | — | — | — | 2.2 | 3.9 | 5.5 | 9.1 | 3.2 | — | — | 3.2 | — | — | 5.0 | 7.1 | — |
| AT5G24090 (7) | acidic endochitinase (CHIB1) | −1.3 | 1.0 | −1.1 | 1.8 | −1.3 | 1.5 | 2.8 | 3.0 | 1.0 | 2.1 | 3.7 | 2.0 | 2.0 | 1.8 | 7.7 | 3.5 | −1.4 |
| AT5G62150 (8) | peptidoglycan-binding LysM domain-containing protein | −1.2 | 1.0 | −1.2 | −1.2 | 1.2 | 1.4 | 2.3 | 4.0 | 4.3 | 1.7 | 2.3 | 1.4 | 2.9 | 2.5 | 5.6 | 8.4 | −1.1 |

Example IV

Preparation of Transgenic Plants

Promoter cloning. For genes showing appropriate patterns of regulation, approximately 1.2 kb of upstream sequence were cloned by PCR (unless this region contained another gene, in which case the upstream sequence up to the next gene was cloned). Each promoter was cloned into an expression vector (vectors used in this study included SEQ ID NOs: 40-76) in front of G1795, SEQ ID NO: 77, a gene that provides Sclerotinia and Erysiphe resistance, but which also produces substantial deleterious morphological effects (e.g., dwarfing, late development, reduced fertility) when constitutively overexpressed. A subset of promoters was also cloned in front of G 1792, SEQ ID NO: 79, a gene related to G1795, but which provides Botrytis and Erysiphe resistance and slightly less severe morphological side effects when overexpressed.

Transformation. Transformation of Arabidopsis was performed by an Agrobacterium-mediated protocol based on the method of Bechtold and Pelletier (1998) Methods Mol. Biol. 82: 259-266. Unless otherwise specified, all experimental work was performed using the Columbia ecotype.

Plant preparation. Arabidopsis seeds were sown on mesh covered pots. The seedlings were thinned so that 6-10 evenly spaced plants remained on each pot 10 days after planting. The primary bolts were cut off a week before transformation to break apical dominance and encourage auxiliary shoots to form. Transformation was typically performed at 4-5 weeks after sowing.

Bacterial culture preparation. Agrobacterium stocks were inoculated from single colony plates or from glycerol stocks and grown with the appropriate antibiotics and grown until saturation. On the morning of transformation, the saturated cultures were centrifuged and bacterial pellets are re-suspended in Infiltration Media (0.5× MS, 1× B5 Vitamins, 5% sucrose, 1 mg/ml benzylaminopurine riboside, 200 µl/L Silwet L77) until an A600 reading of 0.8 was reached.

Transformation and seed harvest. The Agrobacterium solution was poured into dipping containers. All flower buds and rosette leaves of the plants were immersed in this solution for 30 seconds. The plants were laid on their side and wrapped to keep the humidity high. The plants were kept this way overnight at 4° C. and then the pots were turned upright, unwrapped, and moved to the growth racks.

The plants were maintained on the growth rack under 24-hour light until seeds were ready to be harvested. Seeds were harvested when 80% of the siliques of the transformed plants were ripe (approximately 5 weeks after the initial transformation). This seed was deemed T0 seed, since it was obtained from the T0 generation, and was later plated on selection plates (either kanamycin or sulfonamide). Resistant plants that were identified on such selection plates comprise the T1 generation.

T1 plants were subjected to morphological analysis. Promoters that produced a substantial amelioration of the negative effects of G1795 (SEQ ID NO: 77) overexpression were subjected to further analysis by propagation into the T2 generation, where the plants were analyzed for disease resistance.

Example V

Disease Assays

Resistance to Sclerotinia sclerotiorum and Botrytis cinerea was assessed in plate-based assays. Unless otherwise stated, all experiments were performed with the Arabidopsis thaliana ecotype Columbia (Col-0). Control plants for assays on lines containing direct promoter-fusion constructs were wild-type plants or Col-0 plants transformed an empty transformation vector (pMEN65).

Prior to plating, seed for all experiments were surface sterilized in the following manner: (1) 5 minute incubation with mixing in 70% ethanol; (2) 20 minute incubation with mixing in 30% bleach, 0.01% Triton X-100; (3) five rinses with sterile water. Seeds were resuspended in 0.1% sterile agarose and stratified at 4° C. for 2-4 days.

Sterile seeds were sown on starter plates (15 mm deep) containing 50% MS solution, 1% sucrose, 0.05% MES, and 1% Bacto-Agar. 40 to 50 seeds were sown on each plate. Plates were incubated at 22° C. under 24-hour light (95-110 µE m−2 s−1) in a germination growth chamber. On day 10, seedlings were transferred to assay plates (25 mm deep plates with medium minus sucrose). On day 14, seedlings were inoculated (specific method below). After inoculation, plates were put in a growth chamber under a 12-hour light/12-hour dark schedule. Light intensity was lowered to 70-80 µE m−2 s−1 for the disease assay.

Sclerotinia inoculum preparation. A Sclerotinia liquid culture was started three days prior to plant inoculation by cutting a small agar plug (¼ sq. inch) from a 14- to 21-day old Sclerotinia plate (on Potato Dextrose Agar; PDA) and placing it into 100 ml of half-strength Potato Dextrose Broth. The culture was allowed to grown in the Potato Dextrose Broth at room temperature under 24-hour light for three days. On the day of seedling inoculation, the hyphal ball was retrieved from the medium, weighed, and ground in a blender with water (50 ml/gm tissue). After grinding, the mycelial suspension was filtered through two layers of cheesecloth and the resulting suspension was diluted 1:5 in water. Plants were inoculated by spraying to run-off with the mycelial suspension using a Preval aerosol sprayer.

Botrytis inoculum preparation. Botrytis inoculum was prepared on the day of inoculation. Spores from a 14- to 21-day old plate (on PDA) were resuspended in a solution of 0.05% glucose, 0.03M $KH_2PO_4$ to a final concentration of $10^4$ spores/ml. Seedlings were inoculated with a Preval aerosol sprayer, as with Sclerotinia inoculation.

Resistance to Erysiphe cichoracearum was assessed in a soil-based assay. Erysiphe cichoracearum was propagated on a pad4 mutant line in the Col-0 background, which is highly susceptible to Erysiphe (Reuber et al. (1998) Plant J. 16: 473-485), or on squash plants, since this particular strain also parasitizes squash. Inocula were maintained by using a small paintbrush to dust conidia from a 2-3 week old culture onto 4-week old plants. For the assay, seedlings were grown on plates for one week under 24-hour light in a germination chamber, then transplanted to soil and grown in a walk-in growth chamber under a 12-hour light/12-hour dark light regimen, 70% humidity. Each line was transplanted to two 13 cm square pots, nine plants per pot. In addition, three control plants are transplanted to each pot, for direct comparison with the test line. Approximately 3.5 weeks after transplanting, plants are inoculated using settling towers, as described by Reuber et al. (1998). Generally, three to four heavily infested leaves are used per pot for the disease assay. Level of fungal growth is evaluated eight to ten days after inoculation.

Example VI

Experimental Results

FIGS. 4-6 illustrate results obtained by overexpressing a disease defense response protein under the regulatory control of disease-inducible promoters of the invention. G1795 (polynucleotide SEQ ID NO: 77 and polypeptide SEQ ID NO: 78) is a transcription factor that, when constitutively overexpressed, has been shown to impart significant broad-spectrum disease resistance to both necrotrophic and biotrophic pathogens. However, this resistance comes at a price; constitutive expression of this Arabidopsis transcription factor generally causes development of small, dark green, late developing and poorly fertile plants. However, overexpression under the regulatory control of the promoter prAT3G02840 (promoter SEQ ID NO: 32, expression vector SEQ ID NO: 69) or prAT1G02360 (promoter SEQ ID NO: 19, expression vector SEQ ID NO: 56) produced plants that appeared normal in growth and development, and yet showed significant resistance to Erysiphe, as compared to control plants (FIGS. 5 and 6, respectively). AT1G02360::G1795 transgenic plants remained essentially free of the biotrophic pathogen. Both prAT1G02360::G1795 and AT1G02360::G1795 transgenic plants were also moderately more resistant to Sclerotinia than controls (Table 6). Transgenic prAT1G35230::G1795 Arabidopsis seedlings challenged with Sclerotinia sclerotiorum effectively resist infection by this necrotrophic pathogen. Control seedlings similarly treated became infected to a significant degree (FIG. 4). When the G1795 polynucleotide was overexpressed under the regulatory control of prAT1G35230 (SEQ ID NO: 22, expression vector SEQ ID NO: 59), the overexpressors achieved similar morphology at various stages of growth as controls. This line was also much more resistant to the biotrophic pathogen Erysiphe than controls.

Table 5 provides results from ten Arabidopsis lines overexpressing G1795 under the regulatory control of another disease-inducible promoter, prAT4G21390 (polynucleotide SEQ ID NO: 15, expression vector SEQ ID NO: 52). Line 662 appeared to be of particular interest in that the plants were wild-type in appearance and generally, in their development (at the late stage of growth, line 662 plants appeared to be slightly late in their development relative to controls). In spite of their wild-type-like appearance, plants of this line were substantially resistant to the necrotrophic pathogen Sclerotinia and remained essentially free of the biotrophic pathogen Erysiphe after inoculation. These results demonstrate that lines of plants that overexpress a disease resistance gene (e.g., a transcription factor) under the regulatory control of a disease-inducible promoter of the invention can be selected that are both similar to wild-type or nearly wild-type in appearance and growth characteristics and yet highly resistant to a broad range of plant pathogens.

For Tables 5-7, resistance scores are indicated as:
+++ Test plants appeared to be essentially free of pathogen
++ Substantially enhanced resistance compared to controls. The phenotype was very consistent for a given line.
+ Enhanced resistance compared to controls. The response was consistent but was only moderately above the normal levels of variability observed.
wt No detectable difference from wild-type controls.
For Tables 6-7, morphology scores are indicated as:
1 No detectable difference from wild-type controls
2 Slightly small, dark green and late developing
3 Moderately small, dark green and late developing
4 Severely dwarfed with other adverse morphological and developmental characteristics

TABLE 5

Morphological, developmental and disease-resistance characteristics of prAT4G21390::G1795 (promoter SEQ ID NO: 15, expression vector SEQ ID NO: 52) overexpressing T1 and T2 lines.

| Line | T1 Morphology and Development | T2 Sclerotinia Resistance | T2 Erysiphe Resistance |
|---|---|---|---|
| 661 | Slightly small, dark green, late developing | + | +++ |
| 662 | Wild type | ++ | +++ |
| 663 | Wild type | Not done | Wild type |
| 664 | Slightly small, dark green, late developing | + | +++ |

TABLE 5-continued

Morphological, developmental and disease-resistance characteristics of prAT4G21390::G1795 (promoter SEQ ID NO: 15, expression vector SEQ ID NO: 52) overexpressing T1 and T2 lines.

| Line | T1 Morphology and Development | T2 *Sclerotinia* Resistance | T2 *Erysiphe* Resistance |
|---|---|---|---|
| 665 | Slightly small, dark green, late developing | + | ++ |
| 666 | Slightly small, dark green, late developing | + | +++ |
| 667 | Slightly small, dark green, late developing | + | +++ |
| 669 | Slightly small, dark green, late developing | Wild type | +++ |
| 670 | Slightly small, dark green, late developing | Wild type | +++ |
| 671 | Slightly small, dark green, late developing | Wild type | ++ |

Tables 6 and 7 list promoters that have been examined for their effect on plant morphology as well as their ability to confer disease resistance in crops.

TABLE 6

Morphological, developmental and disease-resistance characteristics of plants overexpressing G1795 under the regulatory control of disease inducible promoters found in the Sequence Listing

| Promoter SEQ ID NO: | Promoter | Gene natively regulated by promoter | Regulation | Predominant T1 morphology | Predominant T2 *Sclerotinia* Resistance Level | Predominant T2 *Erysiphe* Resistance Level |
|---|---|---|---|---|---|---|
| 1 | prAT1G16420 | unknown, similar to latex prot | SA-induced | 3 | +/++ | +++ |
| 2 | prAT1G26380 | FAD-linked oxidoreductase family | drought-neutral, SA induced | 3 | + | +++ |
| 3 | prAT1G26420 | FAD-linked oxidoreductase family | mannitol repressed (slight) | 1 | + | +/++ |
| 4 | prAT1G28190 | expressed prot | mannitol induced (slight) | 2 | +/++ | +++ |
| 5 | prAT1G56060 | hypothetical protein | SA induced | 3 | + | +++ |
| 6 | prAT1G61560 | *Arabidopsis thaliana* membrane protein Mlo6 | mannitol repressed (slight) | 2 | +/++ | ++ |
| 7 | prAT5G24090 | acidic endochitinase (CHIB1) | Drought, mannitol induced | 3 | ++ | ++ |
| 8 | prAT5G62150 | Peptidoglycan-binding LysM domain-containing protein | Drought, mannitol induced | 2 | ++ | + |
| 9 | prAT2G32210 | expressed protein | drought neutral, SA slightly induced | 3 | ++ | +++ |
| 11 | prAT2G35980 | harpin-induced protein 1 family (HIN1) | mannitol induced (slight) | 2 | + | +++ |
| 12 | prAT3G18250 | hypothetical protein | SA induced | 2 | ++ | ++ |
| 13 | prAT3G63380 | Calcium-transporting ATPase | none | 3 | ++ | ++ |
| 14 | prAT4G01010 | Cyclic nucleotide gated channel | none | 3 | ++ | +++ |
| 15 | prAT4G21390 | serine/threonine kinase | none | 2 | + | +++ |
| 16 | prAT4G35110 | Expressed protein | none | 3 | ++ | +++ |
| 17 | prAT5G22530 | expressed protein | SA induced | 2 | + | ++ |
| 18 | prAT5G64905 | expressed protein | none | 2 | + | ++ |
| 19 | prAT1G02360 | chitinase | SA-induced, drought repressed | 2 | + | +++ |

TABLE 6-continued

Morphological, developmental and disease-resistance characteristics of plants overexpressing G1795 under the regulatory control of disease inducible promoters found in the Sequence Listing

| Promoter SEQ ID NO: | Promoter | Gene natively regulated by promoter | Regulation | Predominant T1 morphology | Predominant T2 Sclerotinia Resistance Level | Predominant T2 Erysiphe Resistance Level |
|---|---|---|---|---|---|---|
| 20 | prAT1G24140 | metallo-proteinase | drought repressed, SA induced | 3 | + | +++ |
| 21 | prAT1G24145 | unknown | drought repressed, SA, ABA-induced | 3 | +/++ | +++ |
| 22 | prAT1G35230 | Arabino-galactan-protein (AGP5) | drought repressed, slight cold, salt induction, ABA, SA induced | 2 | + | +++ |
| 23 | prAT1G57630 | TIR R gene | SA induced, drought repressed | 3 | + | +++ |
| 24 | prAT1G67810 | hypothetical protein | SA induced, drought repressed | 3 | ++ | +++ |
| 25 | prAT4G18250 | receptor serine/threonine kinase PR5K | drought repressed | 2 | + | ++ |
| 26 | prAT4G35180 | Amino acid transporter family | SA induced, drought, ABA repressed | 1 | + | wt |
| 27 | prAT5G18470 | S-receptor kinase precursor? | drought repressed, SA, mannitol induced | 3 | ++ | +++ |
| 28 | prAT5G48540 | Secretory protein | Related drought repressed, cold, ABA, SA induced | 3 | + | +++ |
| 29 | prAT1G30700 | FAD-linked oxido-reductase family | drought induced | 2 | + | ++/+++ |
| 30 | prAT2G29460 | Chromosome II glutathione S-transferase (GST22) | SA, ABA, drought, mannitol induced | 2 | + | ++/+++ |
| 31 | prAT2G43620 | chitinase | induced drought recovery, mannitol, ABA | 3 | + | ++ |
| 32 | prAT3G02840 | CMPG group elicitor-induced prot | drought, SA induced | 2 | + | ++ |
| 33 | prAT3G26830 | PAD3 camalexin biosynthetic gene | drought induced | 2 | + | ++/+++ |
| 34 | prAT5G12930 | expressed protein | drought (recovery) induced | 2 | + | +/++ |
| 35 | prAT5G24110 | WRKY30 | drought induced (slight) | 2 | ++ | +++ |
| 36 | prAT2G18690 | expressed protein | SA induced, drought repressed | 4 | + | +++ |
| 37 | prAT3G22060 | receptor protein kinase related | drought repressed | 1 | ++ | + |
| 38 | prAT3G57240 | (BG3) encodes a member of glycosyl hydrolase family 17 | SA, mannitol induced, drought repressed | 1 | + | wt |
| 39 | prAT2G18660 | expressed protein | SA induced, drought repressed | 3 | + | +++ |

TABLE 7

Morphological, developmental and disease-resistance characteristics of plants overexpressing G1792 under the regulatory control of disease inducible promoters found in the Sequence Listing

| Promoter SEQ ID NO: | Promoter | Gene natively regulated by promoter | Regulation | Predominant T1 morphology | Predominant T2 Sclerotinia Resistance Level | Predominant T2 Erysiphe Resistance Level |
|---|---|---|---|---|---|---|
| 15 | prAT4G21390 | serine/threonine kinase | none | 1 | + | + |
| 23 | prAT1G57630 | TIR R gene | SA induced, drought repressed | 1 | wt | ++ |
| 25 | prAT4G18250 | receptor serine/threonine kinase PR5K | drought repressed | 1 | + | wt |
| 32 | prAT3G02840 | CMPG group elicitor-induced prot | drought, SA induced | 1 | + | wt |
| 34 | prAT5G12930 | expressed protein | drought (recovery) induced | 1 | + | wt |

Example VII

Transformation of Dicots to Produce Increased Disease Resistance

Manipulation of the expression levels of various classes of genes may be used to regulate defense response. This may include for example, genes encoding transcription factors, ERF transcription factors, G28 (SEQ ID NO: 86), G1792 (SEQ ID NO: 80), G1795 (SEQ ID NO: 78), G1791 (SEQ ID NO: 82), or G30 (SEQ ID NO: 84), other genes that regulate defense responses include, for example, kinases and phosphatases, genes that encode enzymes producing phytoalexins or other fungitoxic compounds, genes that encoded fungicidal or bactericidal proteins, or genes that encode natural or artificial inducers of programmed cell death, including natural or artificial disease resistance (R) genes and Avr genes, or other genes that promote cell death. These polynucleotide sequences recombined into, for example, one of the expression vectors of the invention, or another suitable expression vector comprising a disease-inducible promoter found in the present Sequence Listing and operably linked to the gene conferring the plant defense response. The expression vector may be transformed into a plant for the purpose of modifying plant traits and improving yield and/or quality. The cloning vector may be introduced into a variety of plants by means well known in the art such as, for example, direct DNA transfer or Agrobacterium tumefaciens-mediated transformation. It is now routine to produce transgenic plants using most dicot plants (see Weissbach and Weissbach (1989) Methods for Plant Molecular Biology, Academic Press; Gelvin et al. (1990) Plant Molecular Biology Manual, Kluwer Academic Publishers; Herrera-Estrella et al. (1983) Nature 303: 209; Bevan (1984) Nucleic Acids Res. 12: 8711-8721; and Klee (1985) Bio/Technology 3: 637-642). Methods for analysis of traits are routine in the art and examples are disclosed above.

Numerous protocols for the transformation of tomato and soy plants have been previously described, and are well known in the art. Gruber et al. (1993), in Methods in Plant Molecular Biology and Biotechnology, p. 89-119, and Glick and Thompson (1993) Methods in Plant Molecular Biology and Biotechnology, eds., CRC Press, Inc., Boca Raton, describe several expression vectors and culture methods that may be used for cell or tissue transformation and subsequent regeneration. For soybean transformation, methods are described by Miki et al. (1993) in Methods in Plant Molecular Biology and Biotechnology, p. 67-88, Glick and Thompson, eds., CRC Press, Inc., Boca Raton; and U.S. Pat. No. 5,563,055, (Townsend and Thomas), issued Oct. 8, 1996.

There are a substantial number of alternatives to Agrobacterium-mediated transformation protocols, other methods for the purpose of transferring exogenous genes into soybeans or tomatoes. One such method is microprojectile-mediated transformation, in which DNA on the surface of microprojectile particles is driven into plant tissues with a biolistic device (see, for example, Sanford et al. (1987) Part. Sci. Technol. 5:27-37; Christou et al. (1992) Plant. J. 2: 275-281; Sanford (1993) Methods Enzymol. 217: 483-509; Klein et al. (1987) Nature 327: 70-73; U.S. Pat. No. 5,015,580 (Christou et al), issued May 14, 1991; and U.S. Pat. No. 5,322,783 (Tomes et al.), issued Jun. 21, 1994).

Alternatively, sonication methods (see, for example, Zhang et al. (1991) Bio/Technology 9: 996-997); direct uptake of DNA into protoplasts using $CaCl_2$ precipitation, polyvinyl alcohol or poly-L-ornithine (see, for example, Hain et al. (1985) Mol. Gen. Genet. 199: 161-168; Draper et al. (1982) Plant Cell Physiol. 23: 451-458); liposome or spheroplast fusion (see, for example, Deshayes et al. (1985) EMBO J., 4: 2731-2737; Christou et al. (1987) Proc. Nail. Acad. Sci. USA 84: 3962-3966); and electroporation of protoplasts and whole cells and tissues (see, for example, Donn et al.(1990) in Abstracts of VIIth International Congress on Plant Cell and Tissue Culture IAPTC, A2-38: 53; D'Halluin et al. (1992) Plant Cell 4: 1495-1505; and Spencer et al. (1994) Plant Mol. Biol. 24: 51-61) have been used to introduce foreign DNA and expression vectors into plants.

After a plant or plant cell is transformed (and the latter regenerated into a plant), the transformed plant may be crossed with itself or a plant from the same line, a non-transformed or wild-type plant, or another transformed plant from a different transgenic line of plants. Crossing provides the advantages of producing new and often stable transgenic varieties. Genes and the traits they confer that have been introduced into a tomato or soybean line may be moved into distinct line of plants using traditional backcrossing techniques well known in the art. Transformation of tomato plants may be conducted using the protocols of Koornneef et al (1986) In *Tomato Biotechnology*: Alan R. Liss, Inc., 169-178, and in U.S. Pat. No. 6,613,962, the latter method described in brief here. Eight day old cotyledon explants are precultured for 24 hours in Petri dishes containing a feeder layer of *Petunia hybrida* suspension cells plated on MS medium with 2% (w/v) sucrose and 0.8% agar supplemented with 10 µM α-naphthalene acetic acid and 4.4 µM 6-benzylaminopurine. The explants are then infected with a diluted overnight culture of *Agrobacterium tumefaciens* containing an expression vector comprising a polynucleotide of the invention for 5-10 minutes, blotted dry on sterile filter paper and cocultured for 48 hours on the original feeder layer plates. Culture conditions are as described above. Overnight cultures of *Agrobacterium tumefaciens* are diluted in liquid MS medium with 2% (w/v/) sucrose, pH 5.7) to an $OD_{600}$ of 0.8.

Following cocultivation, the cotyledon explants are transferred to Petri dishes with selective medium comprising MS medium with 4.56 µM zeatin, 67.3 µM vancomycin, 418.9 µM cefotaxime and 171.6 µM kanamycin sulfate, and cultured under the culture conditions described above. The explants are subcultured every three weeks onto fresh medium. Emerging shoots are dissected from the underlying callus and transferred to glass jars with selective medium without zeatin to form roots. The formation of roots in a kanamycin sulfate-containing medium is a positive indication of a successful transformation.

Transformation of soybean plants may be conducted using the methods found in, for example, U.S. Pat. No. 5,563,055 (Townsend et al., issued Oct. 8, 1996), described in brief here. In this method soybean seed is surface sterilized by exposure to chlorine gas evolved in a glass bell jar. Seeds are germinated by plating on ⅒ strength agar solidified medium without plant growth regulators and culturing at 28° C. with a 16 hour day length. After three or four days, seed may be prepared for cocultivation. The seedcoat is removed and the elongating radicle removed 3-4 mm below the cotyledons.

Overnight cultures of *Agrobacterium tumefaciens* harboring the expression vector comprising a polynucleotide of the invention are grown to log phase, pooled, and concentrated by centrifugation. Inoculations are conducted in batches such that each plate of seed was treated with a newly resuspended pellet of *Agrobacterium*. The pellets are resuspended in 20 ml inoculation medium. The inoculum is poured into a Petri dish containing prepared seed and the cotyledonary nodes are macerated with a surgical blade. After 30 minutes the explants are transferred to plates of the same medium that has been solidified. Explants are embedded with the adaxial side up and level with the surface of the medium and cultured at 22° C. for three days under white fluorescent light. These plants may then be regenerated according to methods well established in the art, such as by moving the explants after three days to a liquid counter-selection medium (see U.S. Pat. No. 5,563,055).

The explants may then be picked, embedded and cultured in solidified selection medium. After one month on selective media transformed tissue becomes visible as green sectors of regenerating tissue against a background of bleached, less healthy tissue. Explants with green sectors are transferred to an elongation medium. Culture is continued on this medium with transfers to fresh plates every two weeks. When shoots are 0.5 cm in length they may be excised at the base and placed in a rooting medium.

Example VIII

Transformation of Monocots to Produce Increased Disease Resistance

Similar to the general approach disclosed above for dicots, the expression levels of various classes of polynucleotides may be altered to regulate defense response by overexpression under the regulatory control of a disease-inducible promoter of the invention. The polynucleotides may include natural or artificial disease resistance (R) genes and avr genes, or other genes that promote cell death, or the polynucleotides may encode, for example, transcription factors, ERF transcription factors, G28 (SEQ ID NO: 86), G1792 (SEQ ID NO: 80), G1795 (SEQ ID NO: 78), G1791 (SEQ ID NO: 82), or G30 (SEQ ID NO: 84), other polypeptides that regulate defense responses include, for example, kinases and phosphatases, enzymes producing phytoalexins or other fungitoxic compounds, fungicidal or bactericidal proteins, or natural or artificial inducers of programmed cell death.

Cereal plants such as, but not limited to, corn, wheat, rice, sorghum, or barley, may be transformed with the present polynucleotide promoter sequences cloned into a vector containing, for example, a kanamycin-resistance marker. The expression vectors may also be found in the Sequence Listing, or any other suitable expression vector may be similarly used. For example, pMEN020 may be modified to replace the NptII coding region with the BAR gene of *Streptomyces hygroscopicus* that confers resistance to phosphinothricin. The KpnI and BglII sites of the Bar gene are removed by site-directed mutagenesis with silent codon changes.

The cloning vector may be introduced into a variety of cereal plants by means well known in the art including direct DNA transfer or *Agrobacterium tumefaciens*-mediated transformation. The latter approach may be accomplished by a variety of means, including, for example, that of U.S. Pat. No. 5,591,616, in which monocotyledon callus is transformed by contacting dedifferentiating tissue with the *Agrobacterium* containing the cloning vector.

The sample tissues are immersed in a suspension of $3 \times 10^{-9}$ cells of *Agrobacterium* containing the cloning vector for 3-10 minutes. The callus material is cultured on solid medium at 25° C. in the dark for several days. The calli grown on this medium are transferred to Regeneration medium. Transfers are continued every 2-3 weeks (2 or 3 times) until shoots develop. Shoots are then transferred to Shoot-Elongation medium every 2-3 weeks. Healthy looking shoots are transferred to rooting medium and after roots have developed, the plants are placed into moist potting soil.

The transformed plants arc then analyzed for the presence of the NPTII gene/kanamycin resistance by ELISA, using the ELISA NPTII kit from SPrime-3Prime Inc. (Boulder, Colo.).

It is also routine to use other methods to produce transgenic plants of most cereal crops (Vasil (1994) *Plant Mol. Biol.* 25: 925-937) such as corn, wheat, rice, sorghum (Cassas et al. (1993) *Proc. Natl. Acad. Sci. USA* 90: 11212-11216), and barley (Wan and Lemeaux (1994) *Plant Physiol.* 104: 37-48). DNA transfer methods such as the microprojectile method can be used for corn (Fromm et al. (1990) *Bio/Technol.* 8: 833-839; Gordon-Kamm et al. (1990) *Plant Cell* 2: 603-618; Ishida (1990) *Nature Biotechnol.* 14:745-750), wheat (Vasil et al. (1992) *Bio/Technol.* 10:667-674; Vasil et al. (1993) *Bio/Technol.* 11: 1553-1558; Weeks et al. (1993) *Plant Physiol.* 102:1077-1084), and rice (Christou (1991) *Bio/Technol.* 9:957-962; Hiei et al. (1994) *Plant J.* 6:271-282; Aldemita and Hodges (1996) *Planta* 199; 612-617; and Hiei et al. (1997) *Plant Mol. Biol.* 35:205-218). For most cereal plants, embryogenic cells derived from immature scutellum tissues are the preferred cellular targets for transformation (Hiei et al. (1997)supra; Vasil (1994) supra). For transforming corn embryogenic cells derived from immature scutellar tissue using microprojectile bombardment, the A188XB73 genotype is the preferred genotype (Fromm et al. (1990) supra; Gordon-Kamm et al. (1990) supra). After microprojectile bombardment the tissues are selected on phosphinothricin to identify the transgenic embryogenic cells (Gordon-Kamm et al. (1990) supra). Transgenic plants are regenerated by standard corn regeneration techniques (Fromm et al. (1990) supra; Gordon-Kamm et al. (1990) supra).

Example IX

Analysis or Disease Resistance

Northern blot analysis, RT-PCR or microarray analysis of the regenerated, transformed plants may be used to show expression of a polypeptide that regulates a plant's defense response. To verify the ability to confer biotic stress resistance, mature plants overexpressing a such a polypeptide, or alternatively, seedling progeny of these plants, may be challenged by a pathogen. By comparing control plants (for example, wild type or transformed with an empty vector) and transgenic plants similarly treated, the transgenic plants may be shown to have greater resistance to the particular pathogen.

After a dicot plant, monocot plant or plant cell has been transformed (and the latter regenerated into a plant) and shown to have greater resistance to disease, similar or greater size, or greater yield relative to a control plant under the biotic stress conditions, the transformed monocot plant may be crossed with itself or a plant from the same line, a non-transformed or wild-type monocot plant, or another transformed monocot plant from a different transgenic line of plants.

These experiments would demonstrate that sequences that regulate plant defense responses may be controlled by disease-inducible promoters of the invention can be identified and shown to confer greater yield and greater disease resistance in dicots or monocots, including resistance to broad classes of pathogens.

Example X

Sequences that Confer Significant Improvements to Non-*Arabidopsis* Species

Disease-inducible promoters of the invention may be operably linked with polynucleotide sequences that confer disease resistance and the vectors incorporated into crop or forestry plants. In addition to these sequences, it is expected that similar (e.g., synthetically manipulated) or newly discovered promoter sequences closely related to the promoter sequences found in the Sequence Listing can also regulate and improve disease resistance in a similar manner to the sequences found in the Sequence Listing, when transformed into a any of a considerable variety of plants of different species, and including dicots and monocots. The polynucleotides that regulate a plant defense response may confer disease resistance in a non-*Arabidopsis* species when the polynucleotides are overexpressed under the regulatory control of a promoter of the invention without having a significant adverse impact on plant morphology and/or development. The lines that display useful traits may be selected for further study or commercial development.

Monocotyledonous plants, including rice, corn, wheat, rye, sorghum, barley and others, may be transformed with a plasmid containing a promoter of the invention and a polynucleotide encoding a plant defense response polypeptide. The expression vector may contain a kanamycin-resistance or other selectable marker.

The cloning vector may be introduced into monocots by, for example, means described in the previous Example, including direct DNA transfer or *Agrobacterium tumefaciens*-mediated transformation. The latter approach may be accomplished by a variety of means, including, for example, that of U.S. Pat. No. 5,591,616, in which monocotyledon callus is transformed by contacting dedifferentiating tissue with the *Agrobacterium* containing the cloning vector.

The sample tissues are immersed in a suspension of $3\times10^{-9}$ cells of *Agrobacterium* containing the cloning vector for 3-10 minutes. The callus material is cultured on solid medium at 25° C. in the dark for several days. The calli grown on this medium are transferred to Regeneration medium. Transfers are continued every 2-3 weeks (2 or 3 times) until shoots develop. Shoots are then transferred to Shoot-Elongation medium every 2-3 weeks. Healthy looking shoots are transferred to rooting medium and after roots have developed, the plants are placed into moist potting soil.

The transformed plants are then analyzed for the presence of the NPTII gene/kanamycin resistance by ELISA, using the ELISA NPTII kit from 5Prime-3Prime Inc. (Boulder, Colo.).

Northern blot analysis, RT-PCR or microarray analysis of the regenerated, transformed plants may be used to show expression of a particular defense response polypeptide that is capable of conferring increased disease resistance, or increased size or yield, in the transformed plants.

To verify the ability to confer disease resistance, mature plants, or alternatively, seedling progeny of these plants, that express a plant defense response protein, may be challenged using methods described in the above Examples. By comparing wild type plants and the transgenic plants, the latter are shown be more resistant to disease as compared to wild-type or non-transformed control plants, or controls plants transformed with an empty vector, similarly treated.

All publications and patent applications mentioned in this specification are herein incorporated by reference to the same extent as if each individual publication or patent application was specifically and individually indicated to be incorporated by reference.

The present invention is not limited by the specific embodiments described herein. The invention now being fully described, it will be apparent to one of ordinary skill in the art that many changes and modifications can be made thereto without departing from the spirit or scope of the appended claims. Modifications that become apparent from the foregoing description and accompanying figures fall within the scope of the claims.

What is claimed is:

1. A recombinant polynucleotide capable of modulating transcription in a plant, and the recombinant polynucleotide comprises a nucleic acid sequence with at least 95% similarity to SEQ ID NO: 22, or a fragment thereof, or a complement thereof, wherein the nucleic acid sequence, or the fragment thereof, or the complement thereof, regulates expression of a polypeptide in a plant cell in response to a plant disease.

2. The recombinant polynucleotide of claim 1, wherein the recombinant polynucleotide is an RNA polymerase binding site located 5' relative to and operably linked to a nucleic acid sequence that confers, or encodes a sequence that confers, more resistance to a plant disease than the resistance of a control plant.

3. The recombinant polynucleotide of claim 2, wherein the nucleic acid sequence is a natural disease resistance (R) gene, an artificial disease resistance (R) gene, or an avr gene, or the nucleic acid sequence encodes a polypeptide selected from the group consisting of a transcription factor, a kinase, a phosphatase, an enzyme producing a fungitoxic compound, an enzyme producing a phytoalexin, a fungicidal protein, a bactericidal protein, and a natural or artificial inducer of programmed cell death.

4. The recombinant polynucleotide of claim 3, wherein the transcription factor is selected from the group consisting of SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92 and SEQ ID NO: 94.

5. An expression vector comprising the recombinant polynucleotide of claim 1.

6. A transgenic plant comprising the recombinant polynucleotide of claim 1.

7. The transgenic plant of claim 6, wherein the recombinant polynucleotide comprises an RNA polymerase binding site located 5' relative to and operably linked to a nucleic acid sequence that confers, or encodes a polypeptide that confers, greater resistance to a plant disease than the resistance of a control plant.

8. The transgenic plant of claim 7 wherein the nucleic acid sequence is selected from the group consisting of a natural disease resistance (R) gene, an artificial disease resistance (R) gene, and an avr gene, or the nucleic acid sequence encodes a polypeptide selected from the group consisting of a transcription factor, a kinase, a phosphatase, an enzyme producing a fungitoxic compound, an enzyme producing a phytoalexin, a fungicidal protein, a bactericidal protein, and a natural or artificial inducer of programmed cell death.

9. The transgenic plant of claim 8, wherein the transcription factor is selected from the group consisting of SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92 and SEQ ID NO: 94.

10. The transgenic plant of claim 6, wherein the transgenic plant has greater resistance to a plant disease than a control plant.

11. The transgenic plant of claim 10, wherein the plant disease is a fungal disease.

12. The transgenic plant of claim 11, wherein the fungal disease is caused by a member of the genus *Sclerotinia*, *Botrytis* or *Erysiphe*.

13. A transgenic seed produced by the transgenic plant of claim 6.

14. A method for producing a transgenic plant having greater resistance to a pathogen than a control plant, the method steps including:

(a) generating an expression vector comprising a promoter sequence with at least 95% similarity to SEQ ID NO: 22, or a fragment thereof, or a complement thereof, wherein the promoter sequence, or the fragment thereof, or the complement thereof is operably linked to a nucleotide sequence that encodes a polypeptide that regulates a defense response in a plant, and the promoter sequence, or the fragment thereof, or the complement thereof is capable of modulating transcription in a plant in response to a plant disease; and (b) transforming a target plant with the expression vector to produce a transgenic plant;
   wherein the transgenic plant has greater resistance to the pathogen than the control plant.

15. The method of claim 14, the method steps further including:
   (c) crossing the transgenic plant with a plant selected from the group consisting of the transgenic plant itself, a plant from the same line as the transgenic plant, a non-transgenic plant, a wild-type plant, and another transgenic plant from a different transgenic line of plants, to produce a transgenic seed comprising the expression vector.

\* \* \* \* \*